United States Patent
Arya

(10) Patent No.: US 7,226,780 B2
(45) Date of Patent: Jun. 5, 2007

(54) LENTIVIRUS VECTOR SYSTEM

(75) Inventor: Suresh K. Arya, Clarksburg, MD (US)

(73) Assignee: United States of America as Represented by the Secretary of the Department of Health and Human Resources, Washington, DC (US)

( * ) Notice: Subject to any disclaimer, the term of this patent is extended or adjusted under 35 U.S.C. 154(b) by 2 days.

(21) Appl. No.: 10/731,988

(22) Filed: Dec. 9, 2003

(65) Prior Publication Data

US 2004/0147026 A1 Jul. 29, 2004

Related U.S. Application Data

(62) Division of application No. 09/869,588, filed as application No. PCT/US00/00390 on Jan. 6, 2000, now Pat. No. 6,790,657.

(60) Provisional application No. 60/115,247, filed on Jan. 7, 1999.

(51) Int. Cl.
*C12N 15/00* (2006.01)
(52) U.S. Cl. ............... 435/320.1; 435/69.1; 435/235.1
(58) Field of Classification Search ............. 435/235.1, 435/320.1, 69.1
See application file for complete search history.

(56) References Cited

U.S. PATENT DOCUMENTS

| | | | |
|---|---|---|---|
| 5,162,215 A | 11/1992 | Bosselman et al. | |
| 5,656,465 A | 8/1997 | Panicali et al. | |
| 5,658,785 A | 8/1997 | Johnson | |
| 5,665,577 A | 9/1997 | Sodroski et al. | |
| 5,741,486 A | 4/1998 | Pathak et al. | |
| 5,747,307 A | 5/1998 | Lever et al. | |
| 5,747,324 A | 5/1998 | Mazzara et al. | |
| 6,013,516 A * | 1/2000 | Verma et al. | 435/325 |

FOREIGN PATENT DOCUMENTS

| | | |
|---|---|---|
| WO | WO 95/25806 | 9/1995 |
| WO | WO 96/37623 | 11/1996 |
| WO | WO 97/12622 A1 | 4/1997 |
| WO | WO 97/36481 | 10/1997 |
| WO | WO 98/39463 | 9/1998 |
| WO | WO 98/51810 | 11/1998 |
| WO | WO 99/61598 | 12/1999 |

OTHER PUBLICATIONS

McCann, et al., Location of cis-acting signals important for RNA encapsidation in the leader sequence of human immunodeficiency virus type 2. J. Virol. 1997 71: 4133-4137.*
Arya et al. Human Gene Therapy 1998 vol. 9, pp. 1371-1380.*
Arya et al., "Human Immunodeficiency Virus Type 2 Lentivirus Vectors for Gene Transfer: Expression and Potential for Helper Virus-Free Packaging," *Hum. Gene Ther.* 9:1371-1380 (1998).
Blömer et al., "Highly Efficient and Sustained Gene Transfer in Adult Neurons with a Lentivirus Vector," *J. Virol.* 71:6641-6649 (1997).
Borg et al.; "Involvement of Human Immunodeficiency Virus Type-1 Splice Sites in the Cytoplasmic Accumulation of Viral RNA," *Virol.* 236:95-103 (1997).
Buchschacher, et al., "Development of Lentiviral Vectors for Gene Therapy for Human Diseases," *Blood* 8:2499-2504 (2000).
Clavel et al., "Molecular Cloning and Polymorphism of the Human Immune Deficiency Virus Type 2," *Nature* 324:691-695 (1986).
Corbeau et al., "Efficient Gene Transfer by a Human Immunodeficiency Virus Type 1 (HIV-1)-Derived Vector Utilizing a Stable HIV Packaging Cell Line," *Proc. Natl. Acad. Sci. USA* 93:14070-14075 (1996).
Corbeau et al., "Transduction of Human Macrophages Using a Stable HIV-1/HIV-2-Derived Gene Delivery System," *Gene Ther.* 5:99-104 (1998).
Dillon et al., "Function of the Human Immunodeficiency Virus Types 1 and 2 Rev Proteins is Dependent on Their Ability to Interact with a Structured Region Present in env Gene mRNA," *J. Virol.* 64:4428-4437 (1990).

(Continued)

*Primary Examiner*—Bruce R. Campell
*Assistant Examiner*—Myron G. Hill
(74) *Attorney, Agent, or Firm*—Klarquist Sparkman, LLP

(57) ABSTRACT

A method is disclosed for improving encapsidation of transgene RNA using retroviral packaging and transfer vectors. An HIV-2 transfer vector, which includes the transgene, is introduced into a packaging cell that is also transfected with (or stably expresses) an HIV-2 derived packaging vector or a combination of packaging vectors. The packaging vector has mutations in packaging signal sequences that are both upstream and downstream of the 5' splice donor site. The upstream mutation can be a functional deletion of a signal sequence located between the 5' LTR and the 5' splice donor site, while the downstream mutation can be a functional deletion of a signal sequence located between the 5' splice donor site and an initiation codon of the gag gene on the HIV-2 genome. It can also be composed of a combination of two or more partial vectors. A transfer vector, which is introduced into the packaging cell line, has a mutation that renders its splice donor site non-functional. Transgene RNA expression and encapsidation from these cells is markedly increased, but with little or no levels of infectious viral RNA encapsidation. In particular embodiments, the packaging vector is an HIV-2(ROD) clone, such as pROD(SD36) or pROD(SD36/EM) plus pCM-ENV(ROD), the transfer vector is an HIV-2 clone, such as pSGT-5(SDM), and the packaging cell is a 293T cell. The invention also includes vectors used in this method, cells transformed with the vector or vectors, the supernatant of the packaging cells with the encapsidated vector RNA, as well as the encapsidated RNA itself.

20 Claims, 30 Drawing Sheets

OTHER PUBLICATIONS

Garzino-Demo et al., "Human Immunodificiency Virus Type 2 (HIV-2): Packaging Signal and Associated Negative Regulatory Element," *Hum. Gene Ther.* 6:177-184 (1995).

Kafri et al., "Sustained Expression of Genes Delivered Directly into Liver and Muscle by Lentiviral Vectors," *Nature Gen.* 17:314-317 (1997).

Kaye et al., "Human Immunodeficiency Virus Types 1 and 2 Differ in the Predominant Mechanism Used for Selection of Genomic RNA for Encapsidation," *J. Virol.* 73:3023-3031 (1999).

Kumar et al., "Molecular Characterization of an Attenuated Human Immunodeficiency Virus Type 2 Isolate," *J. Virol.* 64:890-901 (1990).

McBride et al., "The Human Immunodeficiency Virus Type 1 Encapsidation Site is a Multipartite RNA Element Composed of Functional Hairpin Structures," *J. Virol.* 70:2963-2973 (1996).

McBride et al., "Efficient Encapsidation of Human Immunodeficiency Virus Type 1 Vectors and Further Characterization of *cis* Elements Required for Encapsidation," *J. Virol.* 71:4544-4554 (1997).

McCann et al., "Location of *cis*-Acting Signals Important for RNA Encapsidation in the Leader Sequence of Human Immunodeficiency Virus Type 2," *J. Virol.* 71:4133-4137 (1997).

Naldini et al., "In Vivo Gene Delivery and Stable Transduction of Nondividing Cells by a Lentiviral Vector," *Science* 272:263-267 (1996).

Parolin et al., "Use of *cis*- and *trans*-Acting Viral Regulatory Sequences to Improve Expression of Human Immunodeficiency Virus Vectors in Human Lymphocytes," *Virol.* 222:415-422 (1996).

Poeschla et al., "Identification of a Human Immunodeficiency Virus Type 2 (HIV-2) Encapsidation Determinant and Transduction of Nondividing Human Cells by HIV-2-Based Lentivirus Vectors," *J. Virol.* 72:6527-6536 (1998).

Poznansky et al., "Gene Transfer into Human Lymphocytes by a Defective Human Immunodeficiency Virus Type 1 Vector," *J. Virol.* 65:532-536 (1991).

Sadaie et al., "Towards Developing HIV-2 Lentivirus-Based Retroviral Vectors for Gene Therapy: Dual Gene Expression in the Context of HIV-2 LTR and Tat," *J. Med. Virol.* 54:118-128 (1998).

Zufferey et al., "Multiply Attenuated Lentiviral Vector Achieves Efficient Gene Delivery In Vivo," *Nature Biotech.* 15:871-875 (1997).

Genbank Accession No. M15390, May 1996.
Genbank Accession No. NM_002985, 1988.
Genbank Accession No. AF105229, Dec. 1998.

* cited by examiner

FIG. 3A
pROD(PK36) Leader Sequence

```
                    310        320         330         340         350
HIV2ROD     GTTGGCGCCT GAACAGGGAC TTGAAGAAGA CTGAGAAGTC TTGGAACACG
ROD(PK36)   GTTGGCGCCT GAACAGGGAC TTGAAGAAGA CTGAGAAGTC TTGGAACACG 360        370         380         390         400
HIV2ROD     GCTGAGTGAA GGCAGTAAGG GCGGCAGGAA CAAACCACGA CGGAGTGCTC
ROD(PK36)   GCTGAGTGAA GGCAGTAAGG GCGGCAGGAA CAAACCACGA CGGAGTGCTC 410        420         430         440         450
HIV2ROD     CTAGAAAGGC GCGGGCCGAG GTACCAAAGG CAGCGTGTGG AGCGGGAGGA
ROD(PK36)   CTAGAAAGGC GCGGGCCGAG GTACCAAAGG GAGCGTGTGG AGCGGGAGGA 460        470         480         490         500
HIV2ROD     GAAGAGGCCT CCGGGTGAAG GTAAGTACCT ACACCAAAAA CTGTAGCCGA
ROD(PK36)   GAAAGAGGCT CCGGGTGAAG GTAAGTACCT ACACC 510        520         530         540         550
HIV2ROD     AAGGGCTTGC TATCCTACCT TTAGACAGGT AGAAGATTGT GGGAGATGGG
ROD(PK36)                                                T GGGAGATGGG
```

FIG. 3B
pROD(SK36) Leader Sequence

```
                    310        320         330         340         350
HIV2ROD     GTTGGCGCCT GAACAGGGAC TTGAAGAAGA CTGAGAAGTC TTGGAACACG
ROD(SK36)   GTTGG 360        370         380         390         400
HIV2ROD     GCTGAGTGAA GGCAGTAAGG GCGGCAGGAA CAAACCACGA CGGAGTGCTC
ROD(SK36)

410        420         430         440         450
HIV2ROD     CTAGAAAGGC GCGGGCCGAG GTACCAAAGG CAGCGTGTGG AGCGGGAGGA
ROD(SK36)

460        470         480         490         500
HIV2ROD     GAAGAGGCCT CCGGGTGAAG GTAAGTACCT ACACCAAAAA CTGTAGCCGA
ROD(SK36)           CT CCGGGTGAAG GTAAGTACCT ACACCAAAAA CTGTAGCCGA 510        520         530         540         550
HIV2ROD     AAGGGCTTGC TATCCTACCT TTAGACAGGT AGAAGATTGT GGGAGATGGG
ROD(SK36)   AAGGGCTTGC TATCCTACCT TTAGACAGGT AGAAGATTGT GGGAGATGGG
```

FIG. 3C
pROD(SD36) Leader Sequence

```
                  310        320        330        340        350
HIV2ROD    GTTGGCGCCT GAACAGGGAC TTGAAGAAGA CTGAGAAGTC TTGGAACACG
ROD(SD36)  GTTGG 360        370        380        390        400
HIV2ROD    GCTGAGTGAA GGCAGTAAGG GCGGCAGGAA CAAACCACGA CGGAGTGCTC
ROD(SD36)

410        420        430        440        450
HIV2ROD    CTAGAAAGGC GCGGGCCGAG GTACCAAAGG CAGCGTGTGG AGCGGGAGGA
ROD(SD36)

460        470        480        490        500
HIV2ROD    GAAGAGGCCT CCGGGTGAAG GTAAGTACCT ACACCAAAAA CTGTAGCCGA
ROD(SD36)            CT CCGGGTGAAG GTAAGTACCT ACACC 510        520        530        540        550
HIV2ROD    AAGGGCTTGC TATCCTACCT TTAGACAGGT AGAAGATTGT GGGAGATGGG
ROD(SD36)                                          GT GGGAGATGGG
```

FIG. 3D
pROD(CG36) Leader Sequence
(Designed and to be created)

```
                  310        320        330        340        350
HIV2ROD    GTTGGCGCCT GAACAGGGAC TTGAAGAAGA CTGAGAAGTC TTGGAACACG
ROD(CG36)  GTTGGCGCCT GAACAGGGAC TTGAAGAAGA CTGAGAAGTC TTGGAACACG 360        370        380        390        400
HIV2ROD    GCTGAGTGAA GGCAGTAAGG GCGGCAGGAA CAAACCACGA CGGAGTGCTC
ROD(CG36)  GCTGAGTGAA GGCAGTAAGG 410        420        430        440        450
HIV2ROD    CTAGAAAGGC GCGGGCCGAG GTACCAAAGG CAGCGTGTGG AGCGGGAGGA
ROD(CG36)

460        470        480        490        500
HIV2ROD    GAAGAGGCCT CCGGGTGAAG GTAAGTACCT ACACCAAAAA CTGTAGCCGA
ROD(CG36)            CT CCGGGTGAAG GTAAGTACCT ACACC 510        520        530        540        550
HIV2ROD    AAGGGCTTGC TATCCTACCT TTAGACAGGT AGAAGATTGT GGGAGATGGG
ROD(CG36)                                          GT GGGAGATGGG
```

FIG. 3E pROD(MR36) Leader Sequence
(Designed and to be created)

```
                    310        320        330        340        350
HIV2ROD      GTTGGCGCCT GAACAGGGAC TTGAAGAAGA CTGAGAAGTC TTGGAACACG
ROD(MR36)    GTTGG 360        370        380        390        400
HIV2ROD      GCTGAGTGAA GGCAGTAAGG GCGGCAGGAA CAAACCACGA CGGAGTGCTC
ROD(MR36)                        GCGGCAGGAA CAAACCACGA CGGAGTGCTC 410        420        430        440        450
HIV2ROD      CTAGAAAGGC GCGGGCCGAG GTACCAAAGG CAGCGTGTGG AGCGGGAGGA
ROD(MR36)    CTAGAAAGGC GCGGGCCGAG GTACCAAAGG GAGCGTGTGG AGCGGGAGGA 460        470        480        490        500
HIV2ROD      GAAGAGGCCT CCGGGTGAAG GTAAGTACCT ACACCAAAAA CTGTAGCCGA
ROD(MR36)    GAAAGAGGCT CCGGGTGAAG GTAAGTACCT ACACC 510        520        530        540        550
HIV2ROD      AAGGGCTTGC TATCCTACCT TTAGACAGGT AGAAGATTGT GGGAGATGGG
ROD(MR36)                                             GT GGGAGATGGG
```

FIG. 4A

HIV-2 pROD(SD36/EM) Sequence of Mutant Region of Envelope
(Insertion mutant)

ROD  (6351) ACAGAGGCTT TTGATGCAT
EM          ACAGAGGCTT TTGATGCATA GGTAGCGTGA GATCTTAGTG CA

ROD                                                  G GAATAATA CA (6380)
EM          TAGGTAGC GTGAGATCTT AGTGCAAAGA TCGAATAATA CA

FIG. 4B pCM-ENV(ROD)(B-14)

```
   1  TCAATATTGG  CCATTAGCCA  TATTATTCAT  TGGTTATATA  GCATAAATCA
  51  ATATTGGCTA  TTGGCCATTG  CATACGTTGT  ATCTATATCA  TAATATGTAC
 101  ATTTATATTG  GCTCATGTCC  AATATGACCG  CCATGTTGGC  ATTGATTATT
 151  GACTAGTTAT  TAATAGTAAT  CAATTACGGG  GTCATTAGTT  CATAGCCCAT
 201  ATATGGAGTT  CCGCGTTACA  TAACTTACGG  TAAATGGCCC  GCCTGGCTGA
 251  CCGCCCAACG  ACCCCCGCCC  ATTGACGTCA  ATAATGACGT  ATGTTCCCAT
 301  AGTAACGCCA  ATAGGGACTT  TCCATTGACG  TCAATGGGTG  GAGTATTTAC
 351  GGTAAACTGC  CCACTTGGCA  GTACATCAAG  TGTATCATAT  GCCAAGTCCG
 401  CCCCCTATTG  ACGTCAATGA  CGGTAAATGG  CCCGCCTGGC  ATTATGCCCA
 451  GTACATGACC  TTACGGGACT  TTCCTACTTG  GCAGTACATC  TACGTATTAG
 501  TCATCGCTAT  TACCATGGTG  ATGCGGTTTT  GGCAGTACAC  CAATGGGCGT
 551  GGATAGCGGT  TTGACTCACG  GGGATTTCCA  AGTCTCCACC  CCATTGACGT
 601  CAATGGGAGT  TTGTTTTGGC  ACCAAAATCA  ACGGGACTTT  CCAAAATGTC
 651  GTAATAACCC  CGCCCCGTTG  ACGCAAATGG  GCGGTAGGCG  TGTACGGTGG
 701  GAGGTCTATA  TAAGCAGAGC  TCGTTTAGTG  AACCGTCAGA  TCACTAGAAG
 751  CTTTATTGCG  GTAGTTTATC  ACAGTTAAAT  TGCTAACGCA  GTCAGTGCTT
 801  CTGACACAAC  GGTCTCGAAC  TTAAGCTGCA  GAAGTTGGTC  GTGAGGCACT
 851  GGGCAGGTAA  GTATCAAGGT  TACAAGACAG  GTTTAAGGAG  ACCAATAGAA
 901  ACTGGGCTTG  TCGAGACAGA  GAAGACTCTT  GCGTTTCTGA  TAGGCACCTA
 951  TTGGTCTTAC  TGACATCCAC  TTTGCCTTTC  TCTCCACAGG  TGTCCACTCC
1001  CAGTTCAATT  ACAGCTCTTA  AGGCTAGAGT  ACTTAATACG  ACTCACTATA
1051  GGCTAGCCTC  GA
```

```
                                               TACACCAGAC AAGTGAGTAT 180
GATGAATCAG CTGCTTATTG CCATTTTATT AGCTAGTGCT TGCTTAGTAT ATTGCACCCA 240
ATATGTAACT GTTTTCTATG GCGTACCCAC GTGGAAAAAT GCAACCATTC CCCTCTTTTG 300
```

```
              310        320        330        340        350        360
               |          |          |          |          |          |
TGCAACCAGA AATAGGGATA CTTGGGGAAC CATACAGTGC TTGCCTGACA ATGATGATTA 360
TCAGGAAATA ACTTTGAATG TAACAGAGGC TTTTGATGCA TGGAATAATA CAGTAACAGA 420
ACAAGCAATG AAAGATGTCT GGCATCTATT CGAGACATCA ATAAAACCAT GTGTCAAACT 480
AACACCTTTA TGTGTAGCAA TGAAATGCAG CAGCACAGAG AGCAGCATAG GAACAACAC  540
AACCTCAAAG AGCACAAGCA CAACCACAAC CACACCCACA GACCAGGAGC AAgagataag 600
```

```
              610        620        630        640        650        660
               |          |          |          |          |          |
tgaggatact ccatgcgcac gcgcagacaa ctgctcagga ttgggagagg aagaaacgat 660
caattgccag ttcaatatga caggattaga aagagataag aaaaaacagt ataatgaaac 720
atggtactca aagatgtgg  tttgtgagac aaataatagc acaaatcaga cccagtgtta 780
catgaaccat tgcaacacat cagtcatcac agaatcatgt gacaagcact attgggatgc 840
tataaggttt agatactgtg caccaccggg ttatgcccta ttaagatgta atgataccaa 900
```

FIG. 4C

```
           910        920        930        940        950        960
            |          |          |          |          |          |
ttattcaggc tttgcaccca actgttctaa agtagtagct tctacatgca ccaggatgat 960
ggaaacgcaa acttccacat ggtttggctt taatggcact agagcagaga atagaacata 1020
tatctattgg catggcagag ataatagaac tatcatcagc ttaaacaaat attataatct 1080
cagtttgcat tgtaagaggc cagggaataa gatagtgaaa caataatgc ttatgtcagg 1140
acatgtgttt cactcccact accagccgat caataaaaga cccagacaag catggtgctg 1200
          1210       1220       1230       1240       1250       1260
            |          |          |          |          |          |
gttcaaaggc aaatggaaag acgccatgca ggaggtgaag gaaacccttg caaaacatcc 1260
caggtataga ggaaccaatg acacaaggaa tattagcttt gcagcgccag gaaaaggctc 1320
agacccagaa gtagcataca tgtggactaa ctgcagagga gagtttctct actgcaacat 1380
gacttggttc ctcaattgga tagagaataa gacacaccgc aattatgcac cgtgccatat 1440
aaagcaaata attaacacat ggcataaggt agggagaaat gtatatttgc ctcccaggga 1500
          1510       1520       1530       1540       1550       1560
            |          |          |          |          |          |
aggggagctg tcctgcaact caacagtaac cagcataatt gctaacattg actggcaaaa 1560
caataatcag acaaacatta cctttagtgc agaggtggca gaactataca gattggagtt 1620
gggagattat aaattggtag aaataacacc aattggcttc gcacctacaa agaaaaaag 1680
atactcctct gctcacggga gacatacaag aggtgtgttc gtgctagggt tcttgggttt 1740
tctcgcaaca gcaggttctg caatgggcgc ggcgtccctg accgtgtcgg ctcagtcccg 1800
          1810       1820       1830       1840       1850       1860
            |          |          |          |          |          |
gactttactg gccgggatag tgcagcaaca gcaacagctg ttggacgtgg tcaagagaca 1860
acaagaactg ttgcgactga ccgtctgggg aacgaaaaac ctccaggcaa gagtcactgc 1920
tatagagaag tacctacagg accaggcgcg gctaaattca tggggatgtg cgtttagaca 1980
agtctgccac actactgtac catgggttaa tgattcctta gcacctgact gggacaatat 2040
gacgtggcag gaatgggaaa aacaagtccg ctacctggag gcaaatatca gtaaaagttt 2100
          2110       2120       2130       2140       2150       2160
            |          |          |          |          |          |
agaacaggca caaattcagc aagagaaaaa tatgtatgaa ctacaaaaat taaatagctg 2160
ggatattttt ggcaattggt ttgacttaac ctcctgggtc aagtatattc aatatggagt 2220
gcttataata gtagcagtaa tagctttaag aatagtgata tatgtagtac aaatgttaag 2280
taggcttaga aagggctata ggcctgtttt ctcttcccc cccggttata tccaacagat 2340
ccatatccac aaggaccggg gacagccagc caacgaagaa acagaagaag acggtggaag 2400
          2410       2420       2430       2440       2450       2460
            |          |          |          |          |          |
caacggtgga gacagatact ggccctggcc gatagcaTAT ATACATTTCC TGATCCGCCA 2460
GCTGATTCGC CTCTTGACCA GACTATACAG CATCTGCAGG GACTTACTAT CCAGGAGCTT 2520
CCTGACCCTC CAACTCATCT ACCAGAATCT CAGAGACTGG CTGAGACTTA GAACAGCCTT 2580
CTTGCAATAT GGGTGCGAGT GGATCCAAGA AGCATTCCAG GCCGCCGCGA GGGCTACAAG 2640
AGAGACTCTT GCGGGCGCGT GCAGGGGCTT GTGGAGGGTA TTGGAACGAA TCGGGAGGGG 2700
          2710       2720       2730       2740       2750       2760
            |          |          |          |          |          |
AATACTCGCG GTTCCAAGAA GGATCAGACA GGGAGCAGAA ATCGCCTCCT GTGAGGGACG 2760
GCAGTATAGC CAGGGAGACT TTATGAATAC TCCATGG
```

FIG. 4D

```
                                                                GGCGG
1101  CCGCTTCGAG  CAGACATGAT  AAGATACATT  GATGAGTTTG  GACAAACCAC
1151  AACTAGAATG  CAGTGAAAAA  AATGCTTTAT  TTGTGAAATT  TGTGATGCTA
1201  TTGCTTTATT  TGTAACCATT  ATAAGCTGCA  ATAAACAAGT  TAACAACAAC
1251  AATTGCATTC  ATTTTATGTT  TCAGGTTCAG  GGGGAGATGT  GGGAGGTTTT
1301  TTAAAGCAAG  TAAAACCTCT  ACAAATGTGG  TAAAATCGAT  AAGGATCCGG
1351  GCTGGCGTAA  TAGCGAAGAG  GCCCGCACCG  ATCGCCCTTC  CCAACAGTTG
1401  CGCAGCCTGA  ATGGCGAATG  GACGCGCCCT  GTAGCGGCGC  ATTAAGCGCG
1451  GCGGGTGTGG  TGGTTACGCG  CAGCGTGACC  GCTACACTTG  CCAGCGCCCT
1501  AGCGCCCGCT  CCTTTCGCTT  TCTTCCCTTC  CTTTCTCGCC  ACGTTCGCCG
1551  GCTTTCCCCG  TCAAGCTCTA  AATCGGGGGC  TCCCTTTAGG  GTTCCGATTT
```

FIG. 5A

SIV 5' LTR Leader Sequence

R→

| | 10 | 20 | 30 | 40 | 50 |
|---|---|---|---|---|---|
| | GCTCTGTATT | CAGTCGCTCT | GCGGAGAGGC | TGGCAGATTG | AGCCCTGGGA |
| | 60 | 70 | 80 | 90 | 100 |
| | GGTTCTCTCC | AGCACTAGCA | GGTAGAGCCT | GGGTGTTCCC | TGCTAGACTC |
| | 110 | 120 | 130 | 140 | 150 |
| | TCACCAGCAC | TTGGCCGGTG | CTGGGCAGAG | TGACTCCACG | CTTGCTTGCT |

← R |U5 →

| | 160 | 170 | 180 | 190 | 200 |
|---|---|---|---|---|---|
| | TAAAGCCCTC | TTCAATAAAG | CTGCCATTTT | AGAAGTAAGC | TAGTGTGTGT |
| | 210 | 220 | 230 | 240 | 250 |
| | TCCCATCTCT | CCTAGCCGCC | GCCTGGTCAA | CTCGGTACTC | AATAATAAGA |
| | 260 | 270 | 280 | 290 | 300 |
| | AGACCCTGGT | CTGTTAGGAC | CCTTTCTGCT | TTGGGAAACC | GAAGCAGGAA |

← U5 |Leader →

| | 310 | 320 | 330 | 340 | 350 |
|---|---|---|---|---|---|
| | AATCCCTAGC | AGATTGGCGC | CTGAACAGGG | ACTTGAAGGA | GAGTGAGAGA |
| | 360 | 370 | 380 | 390 | 400 |
| | CTCCTGAGTA | CGGCTGAGTG | AAGGCAGTAA | GGGCGGCAGG | AACCAACCAC |
| | 410 | 420 | 430 | 440 | 450 |
| | GACGGAGTGC | TCCTATAAAG | GCGCGGGTCG | GTACCAGACG | GCGTGAGGAG |

SD

| | 460 | 470 | 480 | 490 | 500 |
|---|---|---|---|---|---|
| | CGGGAGAGGA | AGAGGCCTCC | GGTTGCAGGT | AAGTGCAACA | CAAAAAAGAA |
| | 510 | 520 | 530 | 540 | 550 |
| | ATAGCTGTCT | TTTATCCAGG | AAGGGGTAAT | AAGATAGAGT | GGGAGATGGG |
| | 560 | | | | |
| | CGTGAGAAAC | | | | |

FIG. 5B pSIV(SD36)

|  | 320 | 330 | 340 | 350 | 360 |
|---|---|---|---|---|---|
| WTL | GATTGGCGC | CTGAACAGGG | ACTTGAAGGA | GAGTGAGAGA | CTCCTGAGTA |
| SD36 | GATTGG | | | | |

|  | 370 | 380 | 390 | 400 | 410 |
|---|---|---|---|---|---|
| WTL | CGGCTGAGTG | AAGGCAGTAA | GGGCGGCAGG | AACCAACCAC | GACGGAGTGC |
| SD36 | | | | | |

|  | 420 | 430 | 440 | 450 | 460 |
|---|---|---|---|---|---|
| WTL | TCCTATAAAG | GCGCGGGTCG | GTACCAGACG | GCGTGAGGAG | CGGGAGAGGA |
| SD36 | | SD | | | |

|  | 470 | 480 | 490 | 500 | 510 |
|---|---|---|---|---|---|
| WTL | AGAGGCCTCC | GGTTGCAGGT | AAGTGCAACA | CAAAAAAGAA | ATAGCTGTCT |
| SD36 | CTCC | GGTTGCAGGT | AAGTGCAACA | CA | |

|  | 520 | 530 | 540 | 550 | 560 |
|---|---|---|---|---|---|
| WTL | TTTATCCAGG | AAGGGGTAAT | AAGATAGAGT | GGGAGATGGG | CGTGAGAAAC |
| SD36 | | | GT | GGGAGATGGG | CGTGAGAAAC |

FIG. 5C pSIV(SDM)

```
              320         330         340         350         360
WTL      GATTGGCGC   CTGAACAGGG  ACTTGAAGGA  GAGTGAGAGA  CTCCTGAGTA
SDM      GATTGGCGC   CTGAACAGGG  ACTTGAAGGA  GAGTGAGAGA  CTCCTGAGTA 370         380         390         400         410
WTL      CGGCTGAGTG  AAGGCAGTAA  GGGCGGCAGG  AACCAACCAC  GACGGAGTGC
SDM      CGGCTGAGTG  AAGGCAGTAA  GGGCGGCAGG  AACCAACCAC  GACGGAGTGC 420         430         440         450         460
WTL      TCCTATAAAG  GCGCGGGTCG  GTACCAGACG  GCGTGAGGAG  CGGGAGAGGA
SDM      TCCTATAAAG  GCGCGGGTCG  GTACCAGACG  GCGTGAGGAG  CGGGAGAGGA
                         SD
              470         480         490         500         510
WTL      AGAGGCCTCC  GGTTGCAGGT  AAGTGCAACA  CAAAAAAGAA  ATAGCTGTCT
SDM      AGAGGCCTCC  GGTTGATATC  GAGTGCAACA  CAAAAAAGAA  ATAGCTGTCT 520         530         540         550         560
WTL      TTTATCCAGG  AAGGGGTAAT  AAGATAGAGT  GGGAGATGGG  CGTGAGAAAC
SDM      TTTATCCAGG  AAGGGGTAAT  AAGATAGAGT  GGGAGATGGG  CGTGAGAAAC
```

FIG. 7A pSGT5(SDM/RR)

```
|U3        -530            -520
    GGAA  GGGCTGTATT  ACAGTGATAG

-530        -520        -510        -500        -490        -480
GAGACGTAGA  GTCCTAGACA  TATACTTAGA  AAAGGAAGAG  GGAATAATTG  GAGACTGGCA

-470        -460        -450        -440        -430        -420
GAACTATACT  CATG GACCAG  GAGTAAGGTA  TCCAAAGTTC  TTTGGGTGGT  TATGGAAGCT

-410        -400        -390        -380        -370        -360
AGTACCAGTA  GATGTCCCAC  AAGA GGGAGA  TGACAGTGAG  ACTCACTGCT  TAGTGCATCC

-350        -340        -330        -320        -310        -300
 AGCA CAAACA  AGCAGGTTTG  ATGACCCGCA  TGGAGAAACA  TTAGTTTGGA  GGTTTGACCC

-290        -280        -270        -260        -250        -240
 CACGCTAGCT  TTTAGCTACG  AGGCCTTTAT  TCGATACCCA  GAGGAGTTTG  GGTACAAGTC

-230        -220        -210        -200        -190        -180
 AGGCCTGCCA  GAGGATGAAT  GGAAGGCAAG  ACTGAAAGCA  AGAGGGATAC  CGTTAGCTA

-170        -160        -150        -140        -130        -120
 AAAACAGGAA  CAGCTATACT  TGGTCAGGGC  AGGAAGTAAC  TAACAGAAAA  CAGCTGAGAC

-110        -100         -90         -80         -70         -60
  TGCAGGGACT  TTCCAGAAGG  GGCTGTTACC  AGGGGAGGGA  CATGGGAGGA  GCCGGTGGGG

-50         -40         -30         -20         -10       U3|
  AACGCCCTCA  TACTTTCTGT  ATAAATGTAC  CCGCTACTCG  CATTGTATTC

|R          10          20          30          40          50          60
 GTTCGCTCTG  CGGAGAGGCT  GGCAGATTGA  GCCCTGGGAG  GTTCTCTCCA  GCACTAGCAG 70          80          90         100         110         120
 TGGTCACCTG  GGTGTTCCCT  GCTAGACTCT  CACCAGTGCT  TGGCCGGCAC  TGGGCAGACG 130         140         150         160         170     R|U5  180
 GCTCCACGCT  TGCTTGCTTA  AAAGACCTCT  TAATAAAGCT  GCCAGTTAGA  AGCAAGTTAA 190         200         210         220         230         240
 GTGTGTGCTC  CCATCTCTCC  TAGTCGCCGC  CTGGTCATTC  GGTGTTCATC  TAAAGTAACA 250         260         270         280         290         300
 AGACCCTGGT  CTGTTAGGAC  CCTTTCTGCT  TTGGGAAACC  AAGGCAGGAA  AATCCCTAGC

U5|Leader  310         320         330         340         350         360
 AGGTTGGCGC  CCGAACAGGG  ACTTGAAGAA  GACTGAGAAG  CCTTGGAACA  CGGCTGAGTG 370         380         390         400         410         420
 AAGGCAGTAA  GGGCGGCAGG  AACAAACCAC  GACGGAGTGC  TCCTAGAAAA  GCGCAGGCCG
```

FIG. 7B

```
              430         440         450         460       470|---SDM---|  480
         AGGTACCAAG GGCGGCGTGT GGAGCGGGAG TGAAAGAGGC CTCCGGGTGA TATCAGTGCC 490         500         510         520         530         540
         TACACCAAAT ACAGTAGCCA GAAGGGCTTG TTATCCTACC TTTAGACGGG TAGAAGATTG

Leader |gag     560         570         580         590         600
         TGGGAGATGC CATGGTAGGG CGCGAGAAAC TCCGTCTTGA GAGGGAAAAA AGCAGACGAA 610         620         630         640         650         660
         TTAGAAAAGA TTAGGTTACG GCCCGGCGGA AAGAAAAAAT ATAGGCTAAA ACATATTGTG 670         680         690         700         710         720
         TGGGCAGCGA ATGAATTGGA CAGATTCGGA TTGGCAGAGA GCCTGTTGGA GTCAAAAGAG 730         740         750         760         770         780
         GGTTGCCAAAA AAATTCTTAC AGTTTTAGAT CCATTAGTAC CGACAGGGTC AGAAAATTTA 790         800         810         820         830         840
         AAAAGCCTTT TTAATACTGT CTGCGTCATT TGGTGTATAC ACGCAGAAGA GAAAGCGAAA 850         860         870         880         890         900
         GATACTGAAG AAGCAAAACA AAAGGTACAG AGACATCTAG TGGCAGAAAC AAAAACTACA 910         920         930         940      950gag(955) |poly(L)
         GAAAAAATGC CAAGTACAAG TAGACCAACA GCACCACCTA GCGGGAACGG AGGAACTCGA 970         980   | RRE(7661) 990       1000        1010        1020
         ATGCATGGTG ACCGCGGCCG CAGAGGTGTA TTCGTGCTAG GGTTCTTAGG TTTTCTCACA 1030        1040        1050        1060        1070        1080
         GCAGGAGCTG CAATGGGCGC GGCGTCCTTG ACGCTGTCGG CTCAGTCTCG GACTTTATTG 1090        1100        1110        1120        1130        1140
         GCCGGGATAG TGCAGCAACA GCAACAGCTG TTGGACGTGG TCAAGAGACA ACAAGAAATG 1150        1160        1170        1180        1190        1200
         TTGCGACTGA CCGTCTGGGG AACAAAAAAT CTCCAGGCAA GAGTCACTGC TATCGAGAAA 1210        1220        1230        1240        1250        1260
         TACTTAAAGG ACCAGGCGC AACTAAATTCA TGGGGATGTG CGTCTAGACA AGTCTGCCAC 1270   RRE(7960)| poly(L)   1290      |(8770)     1310        1320
         ACTACTGTAC CATGGGTAGC GGCCGCTCGC GAGTAGACCA TGGAGAGCCC CAGCAGAAGG 1330        1340        1350        1360        1370        1380
         GGAGAAAGGC TCGTACAAGC AACAAAATAT GGATGATGTA GATTCAGATG ATGATGACCT 1390        1400        1410        1420        1430        1440
         AGTAGGGGTC CCTGTCACAC CAAGAGTACC ATTAAGAGAA ATGACATATA GGTTGGCAAG 1450        1460        1470   (8944)|U3 1480     1490        1500
         AGAT ATGTCA CATTTGATAA AAGAAAAGGG GGGACTGGAA GGGCTGTATT ACAGTGATAG
```

FIG. 7C

```
         1510         1520         1530         1540         1550         1560
GAGACGTAGA GTCCTAGACA TATACTTAGA AAAGGAAGAG GGAATAATTG GAGACTGGCA 1570         1580         1590         1600         1610         1620
GAACTATACT CATG GACCAG GAGTAAGGTA TCCAAAGTTC TTTGGGTGGT TATGGAAGCT 1630         1640         1650         1660         1670         1680
AGTACCAGTA GATGTCCCAC AAGA GGGAGA TGACAGTGAG ACTCACTGCT TAGTGCATCC 1690         1700         1710         1720         1730         1740
AGCA CAAACA AGCAGGTTTG ATGACCCGCA TGGAGAAACA TTAGTTTGGA GGTTTGACCC 1750         1760         1770         1780         1790         1800
CACGCTAGCT TTTAGCTACG AGGCCTTTAT TCGATACCCA GAGGAGTTTG GGTACAAGTC 1810         1820         1830         1840         1850         1860
AGGCCTGCCA GAGGATGAAT GGAAGGCAAG ACTGAAAGCA AGAGGGATAC CGTTAGCTA 1870         1880         1890         1900         1910         1920
AAAACAGGAA CAGCTATACT TGGTCAGGGC AGGAAGTAAC TAACAGAAAA CAGCTGAGAC 1930         1940         1950         1960         1970         1980
TGCAGGGACT TTCCAGAAGG GGCTGTTACC AGGGGAGGGA CATGGGAGGA GCCGGTGGGG 1990         2000         2010         2020         U3|R         2040
AACGCCCTCA TACTTTCTGT ATAAATGTAC CCGCTACTCG CATTGTATTC AGTCGCTCTG 2050         2060         2070         2080         2090         2100
CGGAGAGGCT GGCAGATTGA GCCC TGGGAG GTTCTCTCCA GCACTAGCAG GTAGGCCTG 2110         2120         2130         2140         2150         2160
GGTGTTCCCT GCTAGACTCT CACCAGTGCT TGGCCGGCAC TGGGCAGACG GCTCCACGCT 2170         2180         2190         R|
TGCTTGCTTA AAAGACCTCT TAATAAAGC TGCCA
```

FIG. 7D

```
        10         20         30         40         50         60
TCTAGAGGAA TTCCGCCCCT CTCCCTCCCC CCCCCCTAAC GTTACTGGCC GAAGCCGCTT
        70         80         90        100        110        120
GGAATAAGGC CGGTGTGCGT TTGTCTATAT GTTATTTTCC ACCATATTGC CGTCTTTTGG
       130        140        150        160        170        180
CAATGTGAGG GCCCGGAAAC CTGGCCCTGT CTTCTTGACG AGCATTCCTA GGGGTCTTTC
       190        200        210        220        230        240
CCCTCTCGCC AAAGGAATGC AAGGTCTGTT GAATGTCGTG AAGGAAGCAG TTCCTCTGGA
       250        260        270        280        290        300
AGCTTCTTGA AGACAAACAA CGTCTGTAGC GACCCTTTGC AGGCAGCGGA ACCCCCCACC
       310        320        330        340        350        360
TGGCGACAGG TGCCTCTGCG GCCAAAAGCC ACGTGTATAA GATACACCTG CAAAGGCGGC
       370        380        390        400        410        420
ACAACCCCAG TGCCACGTTG TGAGTTGGAT AGTTGTGGAA AGAGTCAAAT GGCTCTCCTC
       430        440        450        460        470        480
AAGCGTATTC AACAAGGGGC TGAAGGATGC CCAGAAGGTA CCCCATTGTA TGGGATCTGA
       490        500        510        520        530        540
TCTGGGGCCT CGGTGCACAT GCTTTACATG TGTTTAGTCG AGGTTAAAAA ACGTCTAGGC
       550        560        570        580        590        600
CCCCCGAACC ACGGGGACGT GGTTTTCCTT TGAAAAACAC GATGATAAGC TTGCCACAAC
       610        620        630        640        650        660
CATGGCTGAA CAAGATGGAT TGCACGCAGG TTCTCCGGCC GCTTGGGTGG AGAGGCTATT
       670        680        690        700        710        720
CGGCTATGAC TGGGCACAAC AGACAATCGG CTGCTCTGAT GCCGCCGTGT TCCGGCTGTC
       730        740        750        760        770        780
AGCGCAGGGG CGCCCGGTTC TTTTTGTCAA GACCGACCTG TCCGGTGCCC TGAATGAACT
       790        800        810        820        830        840
GCAGGACGAG GCAGCGCGGC TATCGTGGCT GGCCACGACG GGCGTTCCTT GCGCAGCTGT
       850        860        870        880        890        900
GCTCGACGTT GTCACTGAAG CGGGAAGGGA CTGGCTGCTA TTGGGCGAAG TGCCGGGGCA
       910        920        930        940        950        960
GGATCTCCTG TCATCTCACC TTGCTCCTGC CGAGAAAGTA TCCATCATGG CTGATGCAAT
       970        980        990       1000       1010       1020
GCGGCGGCTG CATACGCTTG ATCCGGCTAC CTGCCCATTC GACCACCAAG CGAAACATCG
      1030       1040       1050       1060       1070       1080
CATCGAGCGA GCACGTACTC GGATGGAAGC CGGTCTTGTC GATCAGGATG ATCTGGACGA
      1090       1100       1110       1120       1130       1140
AGAGCATCAG GGGCTCGCGC CAGCCGAACT GTTCGCCAGG CTCAAGGCGC GCATGCCCGA
      1150       1160       1170       1180       1190       1200
CGGCGAGGAT CTCGTCGTGA CCCATGGCGA TGCCTGCTTG CCGAATATCA TGGTGGAAAA
      1210       1220       1230       1240       1250       1260
TGGCCGCTTT TCTGGATTCA TCGACTGTGG CCGGCTGGGT GTGGCGGACC GCTATCAGGA
      1270       1280       1290       1300       1310       1320
CATAGCGTTG GCTACCCGTG ATATTGCTGA AGAGCTTGGC GGCGAATGGG CTGACCGCTT
      1330       1340       1350       1360       1370       1380
CCTCGTGCTT TACGGTATCG CCGCTCCCGA TTCGCAGCGC ATCGCCTTCT ATCGCCTTCT
      1390       1400       1410
TGACGAGTTC TTCTGAGCGG GATCGGCTAG C
```

FIG. 7E pSGT-5(SDM) 5'LTR-Leader Sequence

```
                       10         20         30         40         50
HIV2ST           GTTCGCTCTG CGGAGAGGCT GGCAGATTGA GCCCTGGGAG GTTCTCTCCA
pSGT5(SDM)       GTTCGCTCTG CGGAGAGGCT GGCAGATTGA GCCCTGGGAG GTTCTCTCCA 60         70         80         90        100
HIV2ST           GCACTAGCAG TGGTCACCTG GGTGTTCCCT GCTAGACTCT CACCAGTGCT
pSGT5(SDM)       GCACTAGCAG TGGTCACCTG GGTGTTCCCT GCTAGACTCT CACCAGTGCT 110        120        130        140        150
HIV2ST           TGGCCGGCAC TGGGCAGACG GCTCCACGCT TGCTTGCTTA AAAGACCTCT
pSGT5(SDM)       TGGGCGGCAC TGGGCAGACG GCTCCACGCT TGCTTGCTTA AAAGACCTCT 160        170        180        190        200
HIV2ST           TAATAAAGCT GCCAGTTAGA AGCAAGTTAA GTGTGTGCTC CCATCTCTCC
pSGT5(SDM)       TAATAAAGCT GCCAGTTAGA AGCAAGTTAA GTGTGTGCTC CCATCTCTCC 210        220        230        240        250
HIV2ST           TAGTCGCCGC CTGGTCATTC GGTGTTCATC TAAAGTAACA AGACCCTGGT
pSGT5(SDM)       TAGTCGCCGC CTGGTCATTC GGTGTTCATC TAAAGTAACA AGACCCTGGT 260        270        280        290        300
HIV2ST           CTGTTAGGAC CCTTTCTGCT TTGGGAAACC AAGGCAGGAA AATCCCTAGC
pSGT5(SDM)       CTGTTAGGAC CCTTTCTGCT TTGGGAAACC AAGGCAGGAA AATCCCTAGC 310        320        330        340        350
HIV2ST           AGGTTGGCGC CCGAACAGGG ACTTGAAGAA GACTGAGAAG CCTTGGAACA
pSGT5(SDM)       AGGTTGGCGC CCGAACAGGG ACTTGAAGAA GACTGAGAAG CCTTGGAACA 360        370        380        390        400
HIV2ST           CGGCTGAGTG AAGGCAGTAA GGGCGGCAGG AACAAACCAC GACGGAGTGC
pSGT5(SDM)       CGGCTGAGTG AAGGCAGTAA GGGCGGCAGG AACAAACCAC GACGGAGTGC 410        420        430        440        450
HIV2ST           TCCTAGAAAA GCGCAGGCCG AGGTACCAAG GGCGGCGTGT GGAGCGGGAG
pSGT5(SDM)       TCCTAGAAAA GCGCAGGCCG AGGTACCAAG GGCGGCGTGT GGAGCGGGAG 460        470        480        490        500
HIV2ST           TGAAAGAGGC CTCCGGGTGA AGGTAAGTGC CTACACCAAA TACAGTAGCC
pSGT5(SDM)       TGAAAGAGGC CTCCGGGTGA TATC AGTGC CTACACCAAA TACAGTAGCC 510        520        530        540        550
HIV2ST           AGAAGGGCTT GTTATCCTAC CTTTAGACGG GTAGAAGATT GTGGGAGATG
pSGT5(SDM)       AGAAGGGCTT GTTATCCTAC CTTTAGACGG GTAGAAGATT GTGG AGATG
```

FIG. 7F pSGT-5(SDM) Leader Sequence

```
                310        320        330        340        350
HIV2ST      AGGTTGGCGC CCGAACAGGG ACTTGAAGAA GACTGAGAAG CCTTGGAACA
pSGT5(SDM)  AGGTTGGCGC CCGAACAGGG ACTTGAAGAA GACTGAGAAG CCTTGGAACA 360        370        380        390        400
HIV2ST      CGGCTGAGTG AAGGCAGTAA GGGCGGCAGG AACAAACCAC GACGGAGTGC
pSGT5(SDM)  CGGCTGAGTG AAGGCAGTAA GGGCGGCAGG AACAAACCAC GACGGAGTGC 410        420        430        440        450
HIV2ST      TCCTAGAAAA GCGCAGGCCG AGGTACCAAG GCGGCGTGT GGAGCGGGAG
pSGT5(SDM)  TCCTAGAAAA GCGCAGGCCG AGGTACCAAG GCGGCGTGT GGAGCGGGAG

SD
                460        470        480        490        500
HIV2ST      TGAAAGAGGC CTCCGGGTGA AGGTAAGTGC CTACACCAAA TACAGTAGCC
pSGT5(SDM)  TGAAAGAGGC CTCCGGGTGA TATC AGTGC CTACACCAAA TACAGTAGCC 510        520        530        540        550
HIV2ST      AGAAGGGCTT GTTATCCTAC CTTTAGACGG GTAGAAGATT GTGGGAGATG
pSGT5(SDM)  AGAAGGGCTT GTTATCCTAC CTTTAGACGG GTAGAAGATT GTGG AGATG
```

FIG. 7G pSGT-5(SDX) Leader Sequence

```
                    310         320         330         340         350
HIV2ST       AGGTTGGCGC  CCGAACAGGG  ACTTGAAGAA  GACTGAGAAG  CCTTGGAACA
pSGT5(SDX)   AGGTTGGCGC  CCGAACAGGG  ACTTGAAGAA  GACTGAGAAG  CCTTGGAACA 360         370         380         390         400
HIV2ST       CGGCTGAGTG  AAGGCAGTAA  GGGCGGCAGG  AACAAACCAC  GACGGAGTGC
pSGT5(SDX)   CGGCTGAGTG  AAGGCAGTAA  GGGCGGCAGG  AACAAACCAC  GACGGAGTGC 410         420         430         440         450
HIV2ST       TCCTAGAAAA  GCGCAGGCCG  AGGTACCAAG  GGCGGCGTGT  GGAGCGGGAG
pSGT5(SDX)   TCCTAGAAAA  GCGCAGGCCG  AGGTACCAAG  GGCGGCGTGT  GGAGCGGGAG

SD
                    460         470         480         490         500
HIV2ST       TGAAAGAGGC  CTCCGGGTGA  AGGTAAGTGC  CTACACCAAA  TACAGTAGCC
pSGT5(SDX)   TGAAAGAGGC  CTCCGG              GC  CTACACCAAA  TACAGTAGCC 510         520         530         540         550
HIV2ST       AGAAGGGCTT  GTTATCCTAC  CTTTAGACGG  GTAGAAGATT  GTGGGAGATG
pSGT5(SDX)   AGAAGGGCTT  GTTATCCTAC  CTTTAGACGG  GTAGAAGATT  GTGG  AGATG
```

LENTIVIRUS VECTOR SYSTEM

CROSS REFERENCE TO RELATED APPLICATIONS

This application is divisional of U.S. application Ser. No. 09/869,588, filed Jun. 28, 2001, now U.S. Pat. No. 6,790,657, which is a U.S. national stage of PCT/US00/00390 filed Jan. 6, 2000, which was published in English under PCT Article 21(2), which in turn claims the benefit of U.S. Provisional Application No. 60/115,247, filed Jan. 7, 1999.

FIELD

The invention relates to retroviral vectors, and their use in gene transfer.

BACKGROUND

The human immunodeficiency virus (HIV) is the etiological agent of the acquired immunodeficiency syndrome (AIDS) and related disorders. The expression of the virus in infected persons is regulated to enable the virus to evade the host's immune response. The HIV viruses (e.g. HIV-1 and HIV-2), as well as the simian immunodeficiency virus (SIV), share many structural and regulatory genes such as gag, pol, env, tat, rev and nef. See Guyader et al., Nature 328: 662–669, 1987, which is incorporated by reference. HIV has been classified as a lentivirus because it causes slow infection, and has structural properties in common with such viruses (Haase, Nature 322:130–136, 1986).

All known retroviruses share features of the replicative cycle, including packaging of viral RNA into virions, entry into target cells, reverse transcription of viral RNA to form the DNA provirus, and stable integration of the provirus into the target cell genome. Replication competent proviruses contain, at a minimum, regulatory long terminal repeats (LTRs) and the gag, pro, pol and env genes which encode core proteins, a protease, reverse transcriptase/RNAse H/integrase and envelope glycoproteins, respectively.

HIV shares the gag, pro, pol and env genes with other retroviruses. HIV-1 also possesses additional genes modulating viral replication, such as the vif, vpr, tat, rev, vpu and nef genes. HIV-2 contains a vpx gene which is not present in HIV-1, but lacks the HIV-1 vpu gene. Additionally the long terminal repeats (LTR) of both HIV-1 and HIV-2 contain cis-acting sequences that are important for integration, transcription and polyadenylation.

HIV, like other retroviruses, are RNA viruses that replicate through a DNA proviral intermediate which is integrated into the genome of the infected host cell. The virion particle contains a dimer of positive strand genomic RNA molecules, which is transcribed from the proviral DNA by the host RNA polymerase II. A portion of these full length RNAs which encode the gag and pol genes of the virus are translated by the host cell ribosomes to produce the structural and enzymatic proteins required for production of virion particles. The provirus also gives rise to a variety of smaller singly and multiply spliced mRNAs coding for the envelope proteins and regulatory proteins.

Wild type retroviruses have been modified to become vehicles for the delivery, stable integration, and expression of cloned genes into a wide variety of cells for experimental and therapeutic purposes. To achieve the aims of transfer and expression of nonviral genes, the vector behaves as a retroviral genome and passes as a virus from a producer cell line. Hence its DNA contains the regions of the wild-type retroviral genome required in cis for incorporation into a retroviral particle. In addition the vector also contains regulatory signals that lead to the optimization of the expression of the cloned gene once the vector is integrated in the target cell as a provirus.

All viral structural genes can be discarded and replaced by heterologous coding sequences, but certain essential sequence elements are retained within the vector. These sequence elements include the packaging sequence, a tRNA binding site, sequences in the LTR that permit "jumping" of the reverse transcriptase between RNA strands during DNA synthesis, sequences near the ends of the LTRs that are necessary for the integration of the vector DNA into the host cell chromosome, and sequences adjoining the 3' LTR that serve as the priming site for synthesis of the plus strand DNA molecules. See Rapley and Walker, Molecular Biomethods Handbook, 1998, chapter 18 for a discussion of principles of retroviral vector construction, and Lewin, Genes V, 1995, chapter 35, for a discussion of the function of retroviral genes. Since vector genomes do not require that the viral structural genes gag, pol and env be retained, nonviral genes can be cloned into the space vacated by their removal.

A significant advance in the use of retroviral vectors has been the use of packaging cells that stably or constitutively express the viral gag, pol and env genes (for example from plasmids) that cannot themselves be packaged by their own encoded proteins, because they lack the essential packaging sequences. However, when a retroviral transfer vector genome is transfected into such a packaging cell, the viral proteins recognize and package the vector RNA genome into viral particles that are released into the culture supernatant. In such a vector system, the transfer vector (which includes the packaging sequence) shuttles the transgene with the potential for regulation and high titer encapsidation, while the packaging cell line encapsidates the transfer vector RNA but not the viral RNA, so that the packaging cell line does not act as a helper virus. The viral particles produced in this manner can be used to deliver the encapsidated retroviral vector to a target cell with high efficiency.

For HIV-2, it has previously been reported that the leader sequence of this lentivirus contains a packaging signal downstream of the splice donor site (Garzino-Demo et al., Hum. Gene Ther. 6:177–184, 1995). Another report suggested that the downstream sequence elements made only a minor or no contribution to RNA encapsidation, and that the major element was located upstream of the splice donor site (McCann and Lever, J. Virol. 71:4133–4137, 1997). Since a knowledge of the packaging signals of HIV-2 is important to the optimal construction of packaging deficient vectors, this uncertainty about the location of the packaging signals has impeded the use of HIV-2 retroviral vector systems.

Moreover, it would be advantageous to express a transgene using an HIV-2 retroviral vector, in such a manner that packaging of the vector RNA is maximized, without an increase in the packaging of viral RNA.

SUMMARY

The invention derives from the discoveries that:

1) deletion of sequences both upstream and downstream of the 5' splice donor (SD) region of the HIV-2 provirus (packaging vector) results in suppressed encapsidation of packaging vector genomes without critical loss of gene expression, thus the production of "helper virus" is suppressed while making adequate structural viral protein available for encapsidation of foreign nucleotides; and 2) that functional deletion of the SD site of the HIV-2 provirus (transfer vector) results in enhanced encapsidation of the transfer vector's own genome, especially when the host cell has been co-transfected with the packaging vector as described under (1) above; and 3) that the HIV-2, but not HIV-1, packaging vector specifically and faithfully packages its own optimally constructed transfer vector as described under (2) above; and 4) that HIV-2 packaging vector gives both better quality and titer of vector.

Transfer and packaging vectors incorporating one or a combination of these features are useful as gene delivery agents, for example gene therapeutic agents, and provide an improved HIV-2 viral vector system that allows transfer of a transgene into the genome of non-dividing cells. The vectors of the invention also may be used to create a high-efficiency packaging cell line that provides greatly enhanced packaging of foreign DNA, especially when such DNA is carried within the SD deleted transfer vector of the invention. Additionally, it has been discovered that, for the transfer vector of the invention, deletion of the 3' LTR and its replacement with a puromycin-poly(A) cassette results in still further suppression of encapsidation of packaging virus genomes, without substantial loss of viral particle expression.

The invention includes the transfer vector derived from an HIV lentivirus, such as HIV-2/ST, wherein the vector is functionally deleted for the splice donor site (SD), and contains a functional packaging signal and a transgene operably linked to a promoter. When susceptible cells (such as 293 cells) are co-transfected with the transfer vector and a packaging-defective HIV-2 having a functional deletion of its packaging signal, production of progeny virions is enhanced by deletion of the SD. Alternatively, the transfer vector can be introduced into a packaging cell stably transfected with the packaging vector. In particular embodiments, the lentivirus is HIV-2, the functional deletion of SD comprises nucleotide changes and/or deletions in the SD nucleotide sequence, and the transgene is a neo gene.

In other embodiments, the invention includes a packaging vector derived from HIV-2, such as HIV-2(ROD), comprising a 5' splice donor site, and an upstream and a downstream packaging signal sequence in the leader sequence, wherein both the upstream and downstream packaging signal sequences are functionally deleted to substantially eliminate packaging of progeny viral RNA, but the splice donor site is functionally intact. In particular examples, the deletions in the packaging sequence comprise no more than 164 nucleotides upstream of the SD and no more than 62 nucleotides downstream of the SD, for example 153 nucleotides (nt 306–458) upstream of the SD, and 52 nucleotides (nt 486–538) downstream of the SD. In particular examples, each deletion is at least 5, 10, 20, 50 or 100 nucleotides in length.

In other examples, the upstream packaging signal is contained in nucleotides downstream from nucleotide 300 and upstream from the SD, and the downstream packaging signal corresponds to nucleotides downstream from the SD and upstream from nucleotide 539. The packaging vector may also include a 3' LTR that is functionally deleted, for example by replacement of the 3' LTR with a heterologous transcriptional termination sequence.

In an alternative embodiment, the HIV packaging vector (or stably transfected cell) includes a polynucleotide sequence which encodes HIV proteins (such as HIV-2 proteins), wherein the polynucleotide sequence includes a mutation in a leader sequence upstream from a 5' splice donor site, and a mutation between the 5' splice donor site and an initiation codon of a gag gene, which results in HIV RNA (such as HIV-2 RNA) transcribed from the vector being substantially packaging defective. The polynucleotide sequence may include (a) a DNA segment from an HIV-2 genome, wherein the DNA segment comprises the HIV gag, pol, rev and env genes, and the vector lacks the bipartite HIV-2 packaging sequence necessary to package HIV-2 RNA into virions; (b) an intact 5' splice donor site; and (c) a promoter operably linked to the DNA segment of (a), wherein the vector, when introduced into or expressed in a eukaryotic host cell, expresses HIV-2 Gag, Pol, Rev, and Env proteins, as well as the Tat protein (if the linked promotor is 5' LTR), to form HIV-2 virions that are not packaged.

In some embodiments, the transfer vector includes a polynucleotide sequence which encodes a transgene, and an HIV (such as an HIV-2) packaging signal and promoter, but which does not encode one or more of a complete gag, pol, or env gene, and in which the splice donor site is mutated to render it non-functional, which increases encapsidation of the transgene vector RNA, compared to encapsidation of the transgene RNA in the absence of the mutation in the splice donor site. The splice donor site may be mutated to functionally delete it by substantially deleting the site, changing its nucleotides, or deleting a sufficient portion of it to increase encapsidation of the transgene RNA.

The invention also includes a cell that expresses or has been transfected with the transfer vector and/or the packaging vector, or which stably expresses the genome of the packaging vector. In particular examples, the cell is a 293T or SupT cell, the transfer vector is pSGT-5(SDM) and the packaging vector is pROD(SD36). When the cell is transfected with or stably expresses both the transfer and packaging vectors, transgene RNA encapsidation is substantially increased in the presence of the transfer vector with the mutated splice donor site, as compared to transgene encapsidation in the presence of the transfer vector in which the splice donor site is not mutated. In particular examples, the packaging vector is an HIV-2(ROD) clone, such as pROD (SD36) or a combination of envelope defective pROD (SD36/EM) and envelope expression plasmid pCON-ENV (ROD). In addition to parental HIV-2(ROD), HIV-2 envelope is derived from mutant HIV-2 and it can fuse with a broad variety of cells whether they contain CD4 markers or not.

Other embodiments include dividing the packaging vector functionally and structurally into two. The first vector contains all of the necessary elements of a packaging vector, except that its envelope is defective. In particular embodiments, this vector is pROD(SD36/EM) or pCM-ROD(SD36/EM). The second vector provides the envelope in trans, to complement the defect. In particular embodiments, this vector is pCM-VSV-G or pCM-ENV(ROD).

The invention also includes a method for improving encapsidation of transgene RNA using retroviral packaging and transfer vectors by (in any order) introducing into the target cell the transfer vector and packaging vector. Alternatively, the transfer vector can be introduced into a cell that stably expresses an HIV-2 packaging genome that has been rendered packaging deficient by the mutation of both the upstream and downstream packaging signals.

Also included in the invention are functionally equivalent transfer and packaging vectors generated using the SIV genome.

Also included in the invention are the supernatant of the packaging cell that includes the encapsidated vector RNA, and the encapsidated vector RNA itself.

The foregoing and other objects, features, and advantages of the invention will become more apparent from the following detailed description of several embodiments which proceeds with reference to the accompanying figures.

BRIEF DESCRIPTION OF THE FIGURES

FIGS. 3A–E shows the upstream and/or downstream sequence deletions from HIV-2(ROD) that generate the following packaging vectors: (A) pROD(PK36) (SEQ ID NO 2); (B) pROD(SK36) (SEQ ID NO 3); (C) pROD(SD36) (SEQ ID NO 4); (D) pROD(CG36) (SEQ ID NO 5); and (E) pROD(MR36) (SEQ ID NO 6). Wild-type HIV-2(ROD) (Leader sequence, SEQ ID NO 1) is shown on top with the corresponding deletions for the packaging vectors below.

FIGS. 4A–E shows dividing the packaging vector into two parts. (A) The sequence of SD36/EM, which is identical to SD36 (see FIG. 3C), except that sequences (SEQ ID NO 7) have been added to the envelope region (nt 6351–6380), generating an envelope insertion mutant. Wild-type HIV2 (ROD) sequence (SEQ ID NO 8) is shown on top with the corresponding insertion shown on the bottom for SD36/EM. (B–D) Sequence of the complementing vector, pCM-ENV (ROD), which contains a functional envelope (SEQ ID NO 9). (E) Combinations of transfer vector [pSGT-5(SDM)] with packaging vectors (either in one or two parts) that can be used.

FIGS. 5A–C shows the sequences for an SIV vector system. (A) The SIV 5' LTR leader sequence (SEQ ID NO 10). (B) The packaging vector pSIV(SD36) with deletions upstream and downstream from the SD (SEQ ID NO 11). (C) The transfer vector pSIV (SDM) with a mutated SD (SEQ ID NO 12). For (B) and (C), the wild-type SIV sequence is shown on top with the deletions and/or mutations shown below.

FIGS. 7A–G shows the sequences of the HIV-2(ST) derived transfer vectors. Wild-type HIV-2(ST) (SEQ ID NO 13) is shown on top with the corresponding deletions in the transfer vectors below. (A–C) Transfer vector pSGT-5 (SDM/RRE1) (SEQ ID NO 14). Nucleotides −534–0 correspond to the upstream U3 region of pSGT-5(SDM). Nucleotides 1–2195 correspond to the HIV-2 part of the pSGT-5 (SDM) sequence. To these sequences, (D) full-length IRES and neo sequences (SEQ ID NO 15) are attached as shown schematically in FIG. 6E. The 5'LTR sequence of pSGT-5 (SDM/RRE1) (SEQ ID NO 16). (F) Nucleotides 300–550 of pSGT-5(SDM) (SEQ ID NO 17) showing the substitution mutation of the SD. Wild-type SD is in italics. (G) Nucleotides 300–550 of pSGT-5(SDX) (SEQ ID NO 18) showing the deletion mutation of the SD.

SEQUENCE LISTING

Figure 1A:
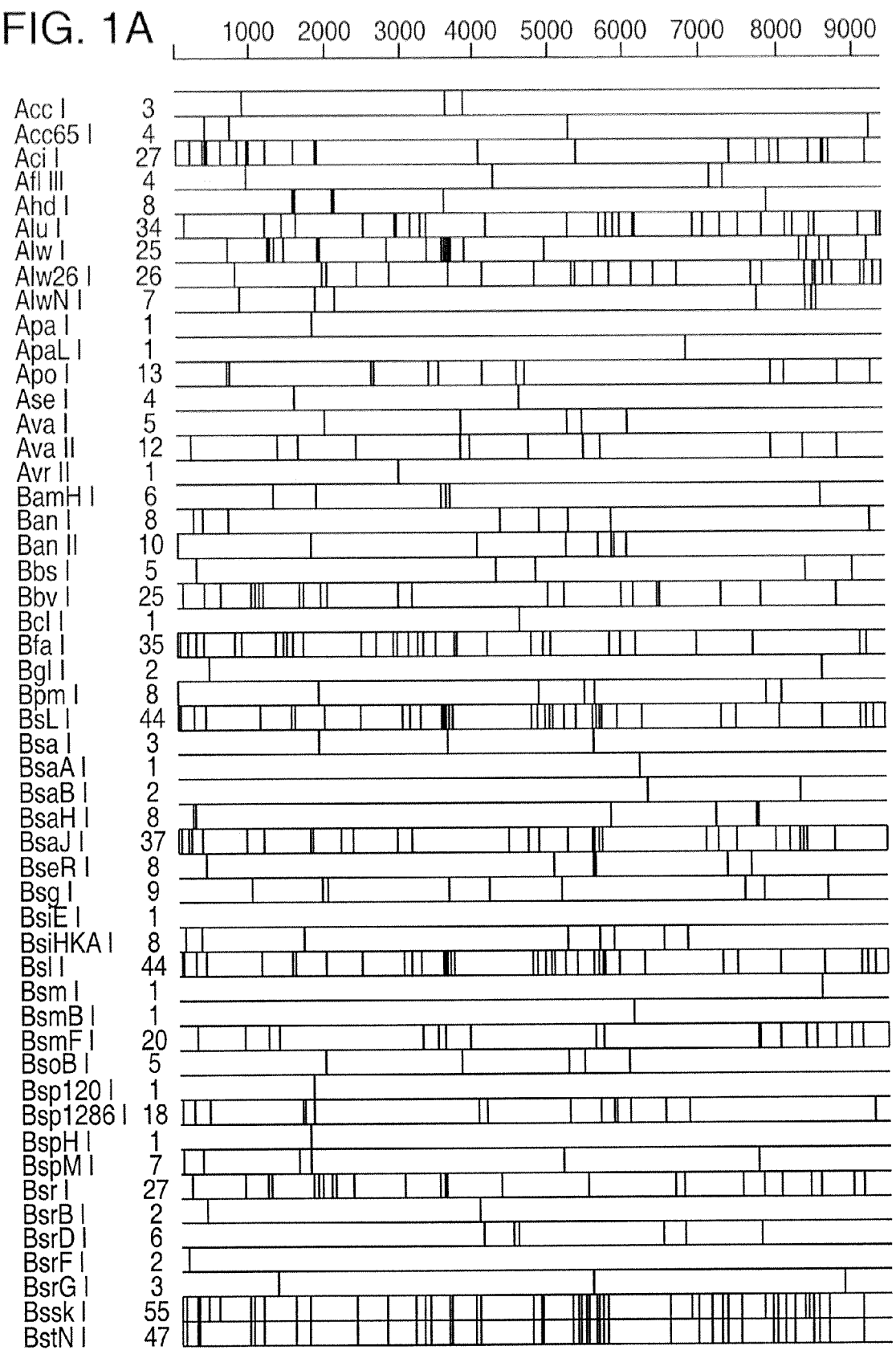
FIGS. 1A–1C show the restriction map of HIV-2 ROD.

The nucleic and amino acid sequences listed in the accompanying sequence listing are shown using standard letter abbreviations for nucleotide bases, and three letter code for amino acids. Only one strand of each nucleic acid sequence is shown, but the complementary strand is understood as included by any reference to the displayed strand.

SEQ ID NO 1 shows the nucleic acid sequence for the HIV-2(ROD) leader sequence.

SEQ ID NO 2 shows the nucleic acid sequence for the pROD(PK36) leader sequence.

SEQ ID NO 3 shows the nucleic acid sequence for the pROD(SK36) leader sequence.

SEQ ID NO 4 shows the nucleic acid sequence for the pROD(SD36) leader sequence.

SEQ ID NO 5 shows the nucleic acid sequence for the pROD(CG36) leader sequence.

SEQ ID NO 6 shows the nucleic acid sequence for the pROD(MR36) leader sequence.

SEQ ID NO 7 shows the nucleic acid sequence for the pROD(SD36/EM) envelope region.

SEQ ID NO 8 shows the nucleic acid sequence for the HIV-2(ROD) envelope region.

SEQ ID NO 9 shows the nucleic acid sequence for the pCM-ENV(ROD) vector.

SEQ ID NO 10 shows the nucleic acid sequence for the SIV 5' LTR leader sequence.

SEQ ID NO 11 shows the nucleic acid sequence for the pSIV(SD36) leader sequence.

SEQ ID NO 12 shows the nucleic acid sequence for the pSIV(SDM) leader sequence.

SEQ ID NO 13 shows the nucleic acid sequence for the HIV-2(ST) 5' LTR.

SEQ ID NO 14 shows the nucleic acid sequence for the transfer vector pSGT-5(SDM/RRE1).

SEQ ID NO 15 shows the nucleic acid sequence for the IRES and neo sequences within pSGT-5(SDM/RRE1).

SEQ ID NO 16 shows the nucleic acid sequence for the pSGT-5(SDM/RRE1) 5' LTR.

SEQ ID NO 17 shows nucleotides 300–550 of the pSGT-5(SDM/RRE1) region containing the substitution mutation of the SD.

SEQ ID NO 18 shows the nucleic acid sequence for pSGT-5(SDX/RRE1) leader region.

SEQ ID NO 19 shows the nucleic acid sequence for 300-nucle tide fragment of HIV-2(ST) RRE1 (nucleotides 7661–7960 of Genbank Accession No. M31113).

SEQ ID NO 20 shows the nucleic acid sequence for the transfer vector pSGT-5(RRE1), which contains a wild-type SD at nt 1023–1028.

SEQ ID NO 21 shows the nucleic acid sequence for the pROD(SD36/EM) packaging vector.

SEQ ID NO 22 shows the nucleic acid sequence for the pCM-ROD(SD36/EM) packaging vector.

SEQ ID NO 23 shows the nucleic acid sequence for the pCM-ENV(ROD) envelope vector.

SEQ ID NO 24 shows the nucleic acid sequence for RRE2, a 530-nucleotide fragment of HIV-2(ROD) (nucleotides 7617–8146 of Genbank Accession No. X05291).

SEQ ID NO 25 shows the nucleic acid sequence for the GFP (Genbank Accession No U55762).

SEQ ID NO 26 shows the nucleic acid sequence for 792-nucleotide fragment of HIV-2(ST) RRE1 (nucleotides 7462–8254 of Genbank Accession No. M31113).

SEQ ID NO 27 shows the nucleic acid sequence for the murine α-GAL-A.

SEQ ID NO 28 shows the nucleic acid sequence for the human AADC.

SEQ ID NO 29 shows the nucleic acid sequence for the human RANTES gene (nt 1–466 of Genbank Accession Number NM_002985).

SEQ ID NO 30 shows the nucleic acid sequence for human BAX (Genbank Accession No. L22474).

SEQ ID NO 31 shows the nucleic acid sequence for the backbone transfer vector, pSGT5(SDM/RRE1/CM).

SEQ ID NO 32 shows the nucleic acid sequence for the IRES and puromycin sequences

DETAILED DESCRIPTION OF SEVERAL EMBODIMENTS

Abbreviations and Definitions

The following definitions and methods are provided to better define the present invention and to guide those of ordinary skill in the art in the practice of the present invention. It must be noted that as used herein and in the appended claims, the singular forms "a" or "an" or "the" include plural referents unless the context clearly dictates otherwise. Thus, for example, reference to "a protein" includes a plurality of such proteins and reference to "the antibody" includes reference to one or more antibodies and equivalents thereof known to those skilled in the art, and so forth.

Unless defined otherwise, all technical and scientific terms used herein have the same meaning as commonly understood to one of ordinary skill in the art to which this invention belongs.

AADC: aromatic amino acid decarboxylase

α-GAL-A: α-galactosidase

CMV: Cytomegalovirus promotor

GFP: Green fluorescent Protein

PCR: polymerase chain reaction

PMSF: Phenylmethylsulfonyl fluoride. An inhibitor of serine proteases.

RT: Room temperature

TU: Transduction units

Animal: Living multicellular vertebrate organisms, a category which includes, for example, mammals and birds.

Cancer: malignant neoplasm that has undergone characteristic anaplasia with loss of differentiation, increased rate of growth, invasion of surrounding tissue, and is capable of metastasis.

cDNA (complementary DNA): A piece of DNA lacking internal, non-coding segments (introns) and regulatory sequences which determine transcription. cDNA may be synthesized in the laboratory by reverse transcription from messenger RNA extracted from cells.

Cell lysate: A mixture resulting from the decomposition, breakdown or lysis of cells or tissue.

Deletion: The removal of a sequence of DNA. The regions on either side may be joined together, or another sequence inserted between them.

DNA: Deoxyribonucleic acid: DNA is a long chain polymer which comprises the genetic material of most living organisms (some viruses have genes comprising ribonucleic acid, RNA). The repeating units in DNA polymers are four different nucleotides, each of which comprises one of the four bases, adenine, guanine, cytosine and thymine bound to a deoxyribose sugar to which a phosphate group is attached. Triplets of nucleotides, referred to as codons, in DNA molecules code for amino acid in a polypeptide. The term codon is also used for the corresponding (and complementary) sequences of three nucleotides in the mRNA into which the DNA sequence is transcribed.

ELISA: Enzyme-linked immunosorbent assay. A form of quantitative immunoassay based on the use of antibodies (or antigens) that are linked to an insoluuble carrier surface, which is then used to capture the relevant antigen (or antibody) in the test solution. The antigen-antibody complex is then detected by measuring the activity of an appropriate enzyme that had previously been covalently attached to the antigen (or antibody).

Functional Deletion: A mutation in a sequence that has an effect equivalent to deletion of the sequence, for example eliminating the function of a packaging signal or splice donor site by a deletion, insertion, or substitution.

Functionally Equivalent: Sequence alterations, in either the transfer or packaging vector sequences, that yield the same results as described herein. Such sequence alterations can include, but are not limited to, conservative substitutions, deletions, mutations, frameshifts, and insertions. In the packaging vector, deletions upstream and downstream from the SD which allow expression, but not encapsidation of the viral RNA as described in EXAMPLES 1 and 2, are functionally equivalent to the packaging vector of the invention. Furthermore, these deletions will not allow for the production of helper virus. In the transfer vector, alterations of the SD sequence which yield enhanced encapsidation of the transfer vector genome, especially when the transfected cell is co-transfected with a packaging vector of the invention (as described in EXAMPLE 5), are functionally equivalent to the transfer vector of the invention.

Infective: A virus or vector is "infective" when it transduces a cell, replicates, and (without the benefit of any complementary virus or vector) spreads progeny vectors or viruses of the same type as the original transducing virus or vector to other cells in an organism or cell culture, where the progeny vectors or viruses have the same ability to reproduce and spread throughout the organism or cell culture. Thus, for example, a nucleic acid encoding an HIV particle is not infective if the nucleic acid cannot be packaged by the HIV particle (e.g. if the HIV particle lacks an HIV packaging site), even though the nucleic acid can be used to transfect and transform a cell. Similarly, an HIV nucleic acid packaged by an HIV particle is not infective if it does not encode the HIV particle that it is packaged in.

Isolated: An "isolated" biological component (such as a nucleic acid, peptide or protein) has been substantially separated, produced apart from, or purified away from other biological components in the cell of the organism in which the component naturally occurs, i.e., other chromosomal and extrachromosomal DNA and RNA, and proteins. Nucleic acids, peptides and proteins which have been "isolated" thus include nucleic acids and proteins purified by standard purification methods. The term also embraces nucleic acids, peptides and proteins prepared by recombinant expression in a host cell as well as chemically synthesized nucleic acids.

Lentivirus: Lentiviruses are characterized by long incubation periods between infection of the host and the manifestation of clinical disease. Lentiviruses infect a wide variety of mammals, including humans, monkeys, sheep, goats, and horses. Includes for example retroviruses, such as immunodeficiency viruses, such as HIV-1, HIV-2, FIV, and SIV.

Malignant: cells which have the properties of anaplasia invasion and metastasis.

Mammal: This term includes both human and non-human mammals. Similarly, the terms "subject," "patient," and "individual" includes human and veterinary subjects.

Neoplasm: abnormal growth of cells

Normal cells: Non-tumor, non-malignant cells.

Nucleic acid: A deoxyribonucleotide or ribonucleotide polymer in either single or double stranded form, and unless otherwise limited, encompasses known analogues of natural nucleotides that hybridize to nucleic acids in a manner similar to naturally occurring nucleotides.

Olig nucleotide: A linear polynucleotide sequence of up to about 200 nucleotide bases in length, for example a polynucleotide (such as DNA or RNA) which is at least 6 nucleotides, for example at least 15, 50, 100 or even 200 nucleotides long.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

ORF (open reading frame): A series of nucleotide triplets (codons) coding for amino acids without any termination codons. These sequences are usually translatable into a peptide.

Ortholog: two nucleotide sequences are orthologs of each other if they share a common ancestral sequence, and diverged when a species carrying that ancestral sequence split into two species. Orthologous sequences are also homologous sequences.

Packaging cell: A cell that provides packaging functions in trans for a transgene introduced into a cell with a transfer vector, but which does not encapsidate its own viral RNA.

Packaging defective: A packaging vector which lacks the nucleic acids necessary for packaging of an RNA corresponding to the packaging vector nucleic acid into a retroviral (e.g. HIV, SIV) capsid. That is, packaging vector nucleic acids are not themselves encapsidated in the HIV or SIV particles which they encode, i.e. they are not infective.

Packaging signal: Nucleic acid sequences upstream and downstream from the SD which are necessary for the efficient packaging of the vector RNA genome.

Packaging vector: Packaging vector nucleic acids lack the nucleic acids necessary for packaging of an RNA corresponding to the packaging vector nucleic acid into a retroviral (e.g. HIV, SIV) capsid. That is, packaging vector nucleic acids are not themselves encapsidated in the HIV or SIV particles which they encode, i.e. they are not infective. The packaging vector optionally includes all of the components necessary for production of HIV or SIV particles, or optionally includes a subset of the components necessary for HIV or SIV packaging. For instance, a packaging cell may be transformed with more than one packaging vector, each of which has a complementary role in the production of an HIV or SIV particle.

Two (or more) HIV- or SIV-based packaging vectors are "complementary" when they together encode all of the functions necessary for HIV or SIV packaging, and when each individually does not encode all of the functions necessary for packaging. For example, when two vectors transduce a single cell and together they encode the information for production of HIV or SIV packaging particles, the two vectors are "complementary." The use of complementary vectors increases the safety of any packaging cell made by transformation with a packaging vector by reducing the possibility that a recombination event will produce an infective virus.

Packaging vectors encode HIV or SIV particles. The HIV particles are competent to package target RNA which has an HIV packaging site. The SIV particles are competent to package target RNA which has an SIV packaging site.

PCR: polymerase chain reaction. Describes a technique in which cycles of denaturation, annealing with primer, and then extension with DNA polymerase are used to amplify the number of copies of a target DNA sequence.

Pharmaceutically acceptable carriers: The pharmaceutically acceptable carriers useful in this invention are conventional. *Remington's Pharmaceutical Sciences*, by E. W. Martin, Mack Publishing Co., Easton, Pa., 15th Edition (1975), describes compositions and formulations suitable for pharmaceutical delivery of the lentiviral vectors herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol, ethanol, sesame oil, combinations thereof, or the like, as a vehicle. The carrier and composition can be sterile, and the formulation suits the mode of administration. For solid compositions (e.g., powder, pill, tablet, or capsule forms), conventional non-toxic solid carriers can include, for example, pharmaceutical grades of mannitol, lactose, starch, sodium saccharine, cellulose, magnesium carbonate, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

The composition can be a liquid solution, suspension, emulsion, tablet, pill, capsule, sustained release formulation, or powder. The composition can be formulated as a suppository, with traditional binders and carriers such as triglycerides.

Probes and primers: Nucleic acid probes and primers may readily be prepared based on the nucleic acid sequences provided by this invention. A probe is an isolated nucleic acid attached to a detectable label or reporter molecule. Typical labels include radioactive isotopes, ligands, chemiluminescent agents, and enzymes. Methods for labeling and guidance in the choice of labels appropriate for various purposes are discussed, e.g., in Sambrook et al., in *Molecular Cloning: A Laboratory Manual*, Cold Spring Harbor Laboratory Press (1989) and Ausubel et al., in *Current Protocols in Molecular Biology*, Greene Publishing Associates and Wiley-Intersciences (1987).

Primers are short nucleic acids, such as DNA oligonucleotides 15 nucleotides or more in length. Primers may be annealed to a complementary target DNA strand by nucleic acid hybridization to form a hybrid between the primer and the target DNA strand, and then extended along the target DNA strand by a DNA polymerase enzyme. Primer pairs can be used for amplification of a nucleic acid sequence, e.g., by the polymerase chain reaction (PCR) or other nucleic-acid amplification methods known in the art.

Methods for preparing and using probes and primers are described, for example, in Sambrook et al. (*Molecular Cloning: A Laboratory Manual*, Cold Spring Harbor Laboratory Press, 1989), Ausubel et al., 1987, and Innis et al., *PCR Protocols, A Guide to Methods and Applications*, 1990, Innis et al. (eds.), 21–27, Academic Press, Inc., San Diego, Calif. PCR primer pairs can be derived from a known sequence, for example, by using computer programs intended for that purpose such as Primer (Version 0.5, © 1991, Whitehead Institute for Biomedical Research, Cambridge, Mass.). One of skill in the art will appreciate that the specificity of a particular probe or primer increases with its length. Thus, for example, a primer comprising 20 consecutive nucleotides of the human AADC cDNA or gene will anneal to a target sequence such as an AADC gene homolog (such as the mouse AADC gene) contained within a cDNA or genomic DNA library with a higher specificity than a corresponding primer of only 15 nucleotides. Thus, in order to obtain greater specificity, probes and primers may be selected that comprise 20, 25, 30, 35, 40, 50 or more consecutive nucleotides of the AADC cDNA or gene sequences.

The invention thus includes isolated nucleic acid molecules that comprise specified lengths of the disclosed gene sequences. Such molecules may comprise at least 20, 21, 25, 30, 35, 40, 50 or 100 or more consecutive nucleotides of these sequences and may be obtained from any region of the disclosed sequences. By way of example, the cDNA and gene sequences may be apportioned into halves or quarters based on sequence length, and the isolated nucleic acid molecules may be derived from the first or second halves of the molecules, or any of the four quarters. In particular, the DNA sequences may code for a unique portion of the protein, which has not been previously disclosed.

pROD or pSGT clone: A clone derived from a publicly available HIV-2 ROD or HIV-2 ST genomic clone, respectively, by standard recombinant techniques such as subcloning, site-directed mutagenesis and the like, or alternatively an artificial nucleic acid synthesized based upon the genomic sequence.

Promoter: A promoter is an array of nucleic acid control sequences which direct transcription of a nucleic acid. A promoter includes necessary nucleic acid sequences near the start site of transcription, such as, in the case of a polymerase II type promoter, a TATA element. A promoter also optionally includes distal enhancer or repressor elements which can be located as much as several thousand base pairs from the start site of transcription. Examples of promotors includes, but is not limited to: the internal promotor CMV; LTR (long terminal repeat); inducible promoters such as the MMTV promoter and the metallothionein promoter; heat shock promoters; the albumin promoter; the histone promoter; TK promoters; B19 parvovirus promoters; and the ApoAI promoter.

Purified: the term purified does not require absolute purity; rather, it is intended as a relative term. Thus, for example, a purified AADC protein preparation is one in which the protein is more pure than the protein in its natural environment within a cell. In one embodiment, a preparation of an AADC protein is purified such that the protein represents at least 50% of the total protein content of the preparation.

Recombinant: A recombinant nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques.

Sequence identity: The similarity between two nucleic acid sequences, or two amino acid sequences, is expressed in terms of the similarity between the sequences, otherwise referred to as sequence identity. Sequence identity is frequently measured in terms of percentage identity (or similarity or homology); the higher the percentage, the more similar the two sequences are. Homologs or orthologs of proteins and corresponding cDNA sequences, for example of the AADC gene, will possess a relatively high degree of sequence identity when aligned using standard methods. This homology will be more significant when the orthologous proteins or cDNAs are derived from species which are more closely related (e.g., human and chimpanzee sequences), compared to species more distantly related (e.g., human and *C. elegans* sequences).

Typically, orthologs are at least 50% identical at the nucleotide level and at least 50% identical at the amino acid level when comparing human sequences, for example when comparing the AADC or RANTES sequences to orthologous AADC and/or RANTES sequences. The orthologs may be at least 60%, 70%, 80%, 90%, 95% or 98% identical at the nucleotide level.

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.*

48:443, 1970; Pearson & Lipman, *Proc. Natl. Acad. Sci. USA* 85:2444, 1988; Higgins & Sharp, *Gene,* 73:237–44, 1988; Higgins & Sharp, *CABIOS* 5:151–3, 1989; Corpet et al., *Nuc. Acids Res.* 16:10881–90, 1988; Huang et al. *Computer Appls. in the Biosciences* 8, 155–65, 1992; and Pearson et al., *Meth. Mol. Bio.* 24:307–31, 1994. Altschul et al,. *J. Mol. Biol.* 215:403–10, 1990, presents a detailed consideration of sequence alignment methods and homology calculations.

The NCBI Basic Local Alignment Search Tool (BLAST) (Altschul et al. *J Mol. Biol.* 215:403–10, 1990) is available from several sources, including the National Center for Biotechnology Information (NCBI, Bethesda, Md.) and on the Internet, for use in connection with the sequence analysis programs blastp, blastn, blastx, tblastn and tblastx. A description of how to determine sequence identity using this program is also available on the Internet.

Homologs of the disclosed HIV and/or transgene proteins typically possess at least 60%, 70%, 75%, 80%, 90%, 95%, 98% or at least 99% sequence identity counted over full-length alignment with the amino acid sequence of the HIV and/or transgene protein using the NCBI Blast 2.0, gapped blastp set to default parameters. For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequence will show increasing percentage identities when assessed by this method, such as at least 70%, 75%, 80%, 90%, 95%, 98%, or 99% sequence identity. When less than the entire sequence is being compared for sequence identity, homologs will typically possess at least 75% sequence identity over short windows of 10–20 amino acids, and may possess sequence identities of at least 85% or at least 90% or 95% depending on their similarity to the reference sequence. Methods for determining sequence identity over such short windows are described on the Internet.

Alternatively, one may manually align the sequences and count the number of identical amino acids in the original sequence and a reference sequence that is compared to the original sequence. This number of identical amino acids is divided by the total number of amino acids in the reference sequence and multiplied by 100 to result in the percent identity.

One of ordinary skill in the art will appreciate that these sequence identity ranges are provided for guidance only; it is entirely possible that strongly significant homologs could be obtained that fall outside of the ranges provided. The present invention provides not only the peptide homologs that are described above, but also nucleic acid molecules that encode such homologs.

One indication that two nucleic acid sequences are substantially identical is that the polypeptide which the first nucleic acid encodes is immunologically cross reactive with the polypeptide encoded by the second nucleic acid.

Nucleic acid sequences that do not show a high degree of identity may nevertheless encode similar amino acid sequences, due to the degeneracy of the genetic code. It is understood that changes in nucleic acid sequence can be made using this degeneracy to produce multiple nucleic acid sequences that all encode substantially the same protein.

An alternative indication that two nucleic acid molecules are closely related is that the two molecules hybridize to each other under stringent conditions, as described in EXAMPLE 21.

The present invention provides not only the peptide homologs that are described above, but also nucleic acid molecules that encode such homologs.

Sample: Includes biological samples containing genomic DNA, RNA, or protein obtained from cells, such as those present in peripheral blood, urine, saliva, tissue biopsy, surgical specimen, amniocentesis samples and autopsy material.

Specifically hybridizable and specifically complementary: Terms which indicate a sufficient degree of complementarity such that stable and specific binding occurs between the oligonucleotide (or its analog) and the DNA or RNA target. The oligonucleotide or oligonucleotide analog need not be 100% complementary to its target sequence to be specifically hybridizable. An oligonucleotide or analog is specifically hybridizable when binding of the oligonucleotide or analog to the target DNA or RNA molecule interferes with the normal function of the target DNA or RNA, and there is a sufficient degree of complementarity to avoid non-specific binding of the oligonucleotide or analog to non-target sequences under conditions in which specific binding is desired, for example under physiological conditions in the case of in vivo assays. Such binding is referred to as "specific hybridization." See EXAMPLE 21 for hybridization conditions.

Splice Donor Site (SD): A site in the nucleic acid sequence which is used in conjunction with a splice acceptor site elsewhere in the genome to eliminate (splice out) a segment of RNA which is not a part of the mature, functional RNA. As used herein, the splice donor site is the major splice donor used to produce all viral messages (functional RNAs coding for the proteins) except the gag-pol precursor. In the infectious full length HIV-2, this site is essential for RNA processing which is quite complex in lenitviruses and without it, virus is not replicative or infectious.

The sequence of the SD is conserved in HIV-2's and differs slightly from HIV-1. Generally, these sequence elements form a consensus set:

```
Consensus:      Donor Exon-AG|GT

AAGT--------CAG|N-Exon Acceptor

HIV-2 (ST)      GTGAAG|GTAAGT

HIV-2 (ROD)     GTGAAG|GTAAGT

HIV-1 (HXb)     CGACTG|GTGAGT

HIV-1 (89.6)    CGACTG|GTGAGT
```

Subject: Living multicellular vertebrate organisms, a category which includes, both human and veterinary subjects for example, mammals, birds and primates.

Sufficient complementarity: When used, indicates that a sufficient number of base pairs exist between the oligonucleotide and the target sequence to achieve detectable binding, and disrupt expression of gene products (for example the transgenes described herein). When expressed or measured by percentage of base pairs formed, the percentage complementarity that fulfills this goal can range from as little as about 50% complementarity to full, (100%) complementary. In general, sufficient complementarity is at least about 50%.

However, sufficient complementarity can be least about 75%, 90%, 95%. 98% or 100% complementarity.

A thorough treatment of the qualitative and quantitative considerations involved in establishing binding conditions that allow one skilled in the art to design appropriate oligonucleotides for use under the desired conditions is provided by Beltz et al. *Methods Enzymol* 100:266–285, 1983, and by Sambrook et al. (ed.), *Molecular Cloning: A Laboratory Manual,* 2nd ed., vol. 1–3, Cold Spring Harbor Laboratory Press, Cold Spring Harbor, N.Y., 1989.

Supernatant: The culture medium in which a cell is grown. The culture medium includes material from the cell, including HIV viral particles which bud off from the cell membrane and enter the culture medium.

Therapeutically active molecule: A molecule that has a biological effect in the treatment of a pathological condition. An example of such a molecule is one which induces Fabry cells to clear excess glycolipd. Another example of such a molecule is one which induces neural cells, such as those of a Parkinson's patient, to convert L-dopa to L-dopamine. Examples of nucleic acid-based therapeutically active molecules are, but are not limited to, lentiviral vectors which express functional α-GAL-A, AADC, BAX, or chemokine proteins or fragments thereof. Therapeutically active molecules also include gene therapy vectors, such as lentiviral vectors containing therapeutic transgene nucleic acid sequences.

Transduced and Transformed: A virus or vector "transduces" a cell when it transfers nucleic acid into the cell. A cell is "transformed" by a nucleic acid transduced into the cell when the DNA becomes stably replicated by the cell, either by incorporation of the nucleic acid into the cellular genome, or by episomal replication. As used herein, the term transformation encompasses all techniques by which a nucleic acid molecule might be introduced into such a cell, including transfection with viral vectors, transformation with plasmid vectors, and introduction of naked DNA by electroporation, lipofection, calcium-DNA precipitates, and particle gun acceleration.

Transfer/Transducing vector: A vector which shuttles a transgene.

Transformed: A transformed cell is a cell into which has been introduced a nucleic acid molecule by molecular biology techniques. As used herein, the term transformation encompasses all techniques by which a nucleic acid molecule might be introduced into such a cell, including transfection with viral vectors, transformation with plasmid vectors, and introduction of naked DNA by electroporation, lipofection, and particle gun acceleration.

Transgene: An exogenous gene supplied by a vector. Examples of such genes include, but are not limited to: neo, GFP, AADC, α-gal, BAX or a chemokine.

Transgenic Cell: Transformed cells which contain foreign, non-native DNA.

Tumor: a neoplasm

Upstream and Downstream Sequences: Upstream sequences are those 5' to the sequence of interest and downstream sequences are 3' to the sequence of interest.

Variants of Amino Acid and Nucleic Acid Sequences: The production of proteins can be accomplished in a variety of ways. DNA sequences which encode for the protein, or a fragment or variant of the protein, can be engineered such that they allow the protein to be expressed in eukaryotic cells, bacteria, insects, and/or plants. In order to accomplish this expression, the DNA sequence can be altered and operably linked to other regulatory sequences. The final product, which contains the regulatory sequences and the therapeutic protein, is referred to as a vector. This vector can then be introduced into the eukaryotic cells, bacteria, insect, and/or plant. Once inside the cell the vector allows the protein to be produced.

One of ordinary skill in the art will appreciate that the DNA can be altered in numerous ways without affecting the biological activity of the encoded protein. For example, PCR may be used to produce variations in the DNA sequence which encodes AADC. Such variants may be variants that are optimized for codon preference in a host cell that is to be used to express the protein, or other sequence changes that facilitate expression.

Two types of cDNA sequence variant may be produced. In the first type, the variation in the cDNA sequence is not manifested as a change in the amino acid sequence of the encoded polypeptide. These silent variations are simply a reflection of the degeneracy of the genetic code. In the second type, the cDNA sequence variation does result in a change in the amino acid sequence of the encoded protein. In such cases, the variant cDNA sequence produces a variant polypeptide sequence. In order to optimize preservation of the functional and immunologic identity of the encoded polypeptide, any such amino acid substitutions may be conservative. Conservative substitutions replace one amino acid with another amino acid that is similar in size, hydrophobicity, etc. Such substitutions generally are conservative when it is desired to finely modulate the characteristics of the protein. Examples of amino acids which may be substituted for an original amino acid in a protein and which are regarded as conservative substitutions include: Ser for Ala; Lys for Arg; Gln or His for Asn; Glu for Asp; Ser for Cys; Asn for Gln; Asp for Glu; Pro for Gly; Asn or Gln for His; Leu or Val for Ile; Ile or Val for Leu; Arg or Gln for Lys; Leu or Ile for Met; Met, Leu or Tyr for Phe; Thr for Ser; Ser for Thr; Tyr for Trp; Trp or Phe for Tyr; and Ile or Leu for Val.

Variations in the cDNA sequence that result in amino acid changes, whether conservative or not, are minimized to enhance preservation of the functional and immunologic identity of the encoded protein. The immunologic identity of the protein may be assessed by determining whether it is recognized by an antibody to AADC (or other protein of interest); a variant that is recognized by such an antibody is immunologically conserved. In particular embodiments, any cDNA sequence variant will introduce no more than 20, for example fewer than 10 amino acid substitutions into the encoded polypeptide. Variant amino acid sequences can, for example, be 80%, 90% or even 95% identical to the native amino acid sequence.

Conserved residues in the same or similar proteins from different species can also provide guidance about possible locations for making substitutions in the sequence. A residue which is highly conserved across several species is more likely to be important to the function of the protein than a residue that is less conserved across several species.

Vector: A nucleic acid molecule as introduced into a host cell, thereby producing a transformed host cell. A vector may include nucleic acid sequences that permit it to replicate in the host cell, such as an origin of replication. A vector may also include one or more selectable marker genes and other genetic elements known in the art. A vector can transduce, transform or infect a cell, thereby causing the cell to express nucleic acids and/or proteins other than those native to the cell. A vector optionally includes materials to aid in achieving entry of the nucleic acid into the cell, such as a viral particle, liposome, protein coating or the like.

Variant Lentiviral or Transgene peptides: Lentiviral or transgene peptides having one or more amino acid substitutions, one or more amino acid deletions, and/or one or more amino acid insertions, so long as the peptide retains the properties of the wild-type protein. Conservative amino acid substitutions may be made in at least 1 position, for example 2, 3, 4, 5 or even 10 or more positions, as long as the peptide retains the ability to function as a lentiviral or transgene protein disclosed in the present specification. For example, variants of the transgene α-GAL-A can be expressed by the lentiviral system of the present invention. Variant α-GAL-A molecules will retain the ability to be expressed by the lentiviral system at levels above that observed in Fabry fibroblasts using methods described in EXAMPLE 11. In addition, the variant α-GAL-A molecules will retain the ability clear excess lipid deposited in Fabry fibroblasts at a better rate than observed for untransduced Fabry fibroblasts, using the methods described in EXAMPLE 11.

Additional definitions of terms commonly used in molecular genetics can be found in Benjamin Lewin, *Genes V* published by Oxford University Press, 1994 (ISBN 0-19-854287-9); Kendrew et al (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

General Methods

The methods of the invention are generally directed to the production of HIV derived transfer and packaging vectors which can be used (either together or in conjunction with other transfer and packaging vectors) to produce packaged transfer vectors that can be used to transfer a transgene into a target cell substantially without the production of competent pathogenic or infectious viral particles.

The present invention utilizes standard laboratory practices for the cloning, manipulation and sequencing of nucleic acids, purification and analysis of proteins and other molecular biological and biochemical techniques, unless otherwise stipulated. Such techniques are explained in detail in standard laboratory manuals such as Sambrook et al., *Molecular Cloning: A Laboratory Manual*, Cold Spring Harbor, N.Y., 1989, and Ausubel et al., in *Current Protocols in Molecular Biology*, Greene Publishing Associates and Wiley-Intersciences (1987). Although the virus from which the transfer and packaging vectors are derived is an RNA virus (HIV-2 or SIV), the molecular cloning may be done using proviral DNA clones, thus allowing the use of standard cloning techniques.

Vector Construction

The packaging and transfer vectors of the invention may be derived, using standard genetic engineering techniques, from a provirus clone of a retrovirus, such as an immunodeficiency virus, for example the Human Immunodeficiency Virus, including HIV-1 or HIV-2, or the Simian Immunodeficiency Virus, SIV.

The Packaging Vector

In this example with HIV-2, it is shown that nucleotide sequences upstream and downstream of the 5' splice donor (SD) site are necessary for the efficient packaging of the vector RNA genome. Selective deletion of these essential packaging sites (packaging sequences) renders the vector incapable of packaging its own RNA (so that it is a "packaging vector"). The packaging vector in this example is made by deleting the HIV-2 packaging site both upstream and downstream of SD in HIV-2, and may be derived by genetic engineering of a provirus. The resulting deletion clones can be used to make viral particles, by transducing the deletion clone into a packaging cell and expressing the clone. Because the clones lack the HIV-2 packaging site, they are not packaged into the viral particles. To increase safety of the transduced packaging cells, the deletion clone (or homologous clones) may be cut (e.g. by subcloning) into multiple expression clones with complementary functions. This decreases the chances that a recombinant event will result in an infectious particle.

Figure 2A:
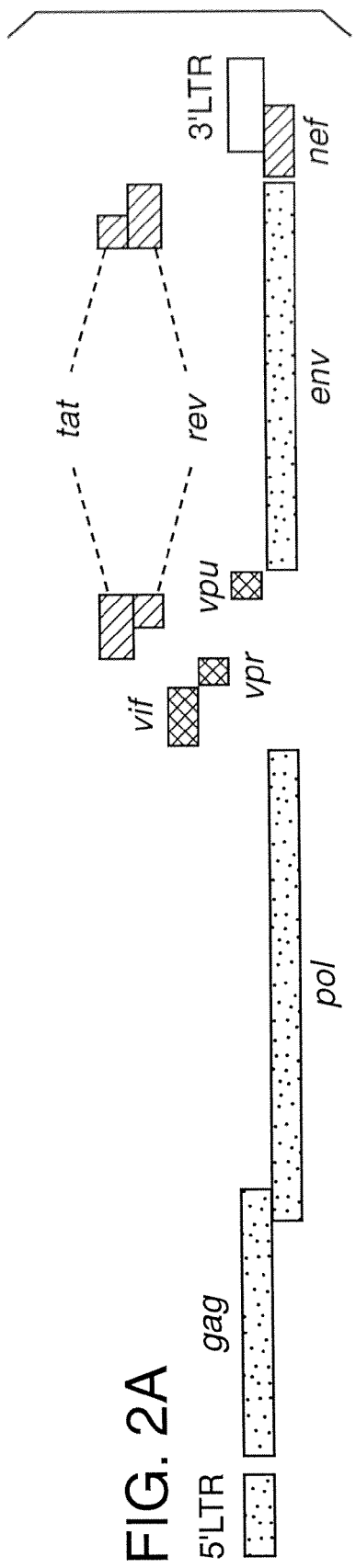
FIG. 2 is a schematic comparison of the genomes of (a) HIV-1 and (b) HIV-2, showing the genomic locations of the genes in each retrovirus.
Figure 2B:
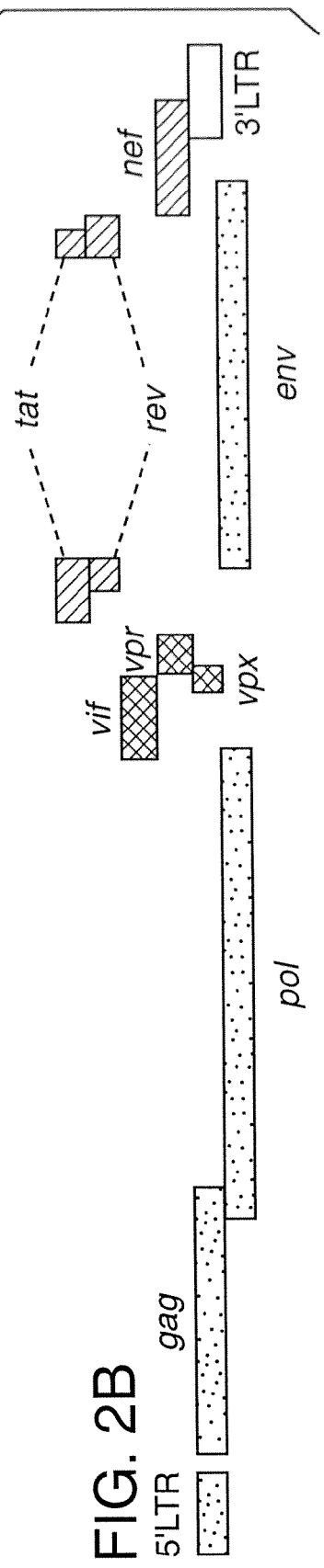

A convenient and well-defined provirus that may be used for this purpose is the provirus molecular clone (pROD1), from HIV-2 ROD (the sequence of which is available under Genbank accession no. M15390, and is further described in Arya et al., *J. Acquir. Immune. Defic. Syndr.* 6:1205–1211, 1993; Arya et al., *J. Gen. Virol.* 75:2253–2260, 1994; and Arya et al., *Hum. Gene Ther.* 9:1371–1380, 1998). Other retroviral provirus constructs may also be used, for instance an HIV-1 or SIV provirus. The sequences for these proviruses are available on Genebank. Examples include, but are not limited to: Genbank Accession Nos. AF075702 (HIV-1 isolate SE8603 from Uganda), M17449 (HIV-1 isolate MN) and AF131870 (SIV). Such a provirus (or combination of complementary viruses), used to produce the packaging vector, should contain a substantially complete retroviral genome including the gag, pol, and env genes, a leader sequence and the 3' and 5' LTRs, and may contain the other HIV-2 structural genes shown in FIG. 2.

Figure 1B:
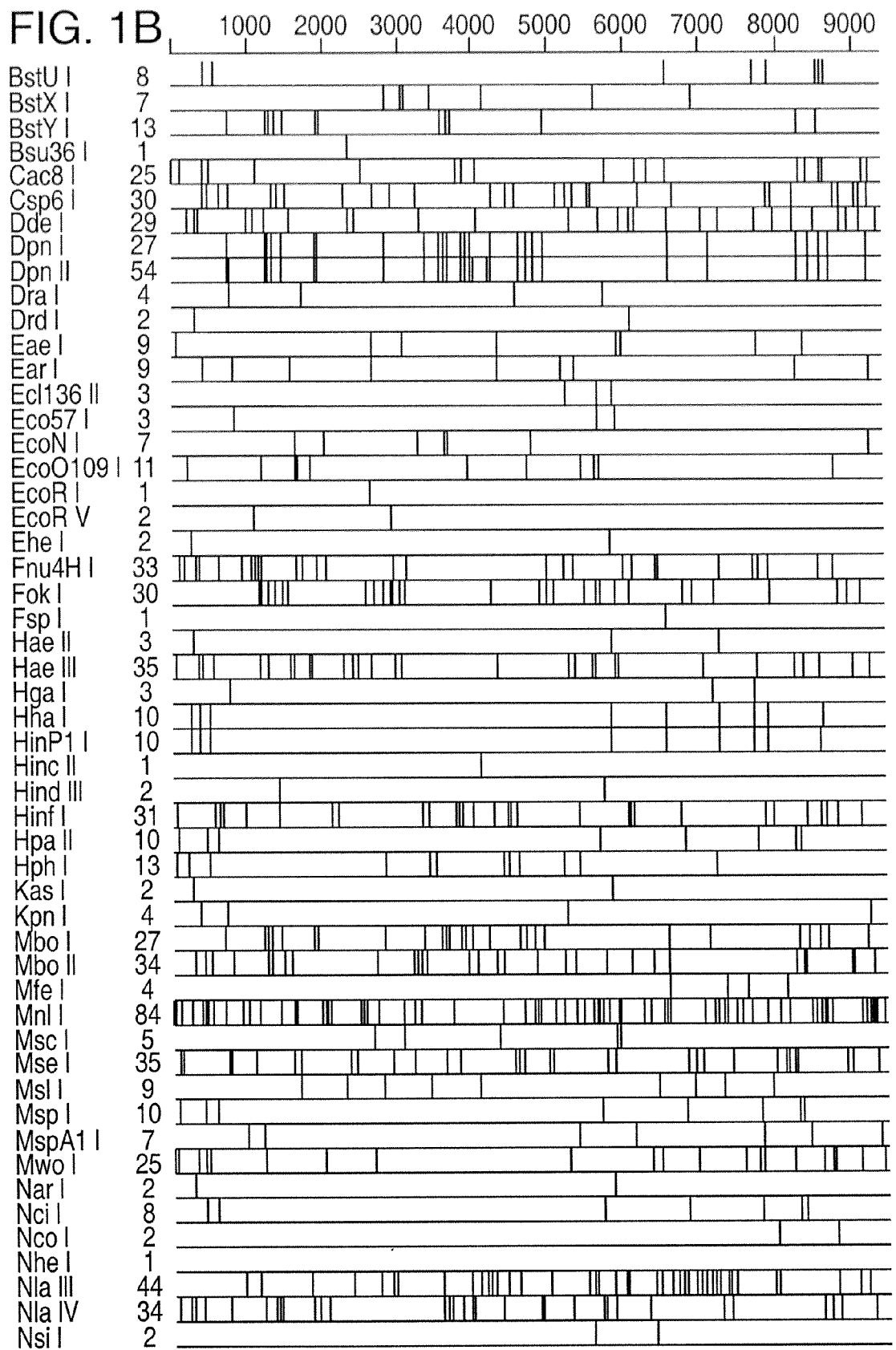
Figure 1C:
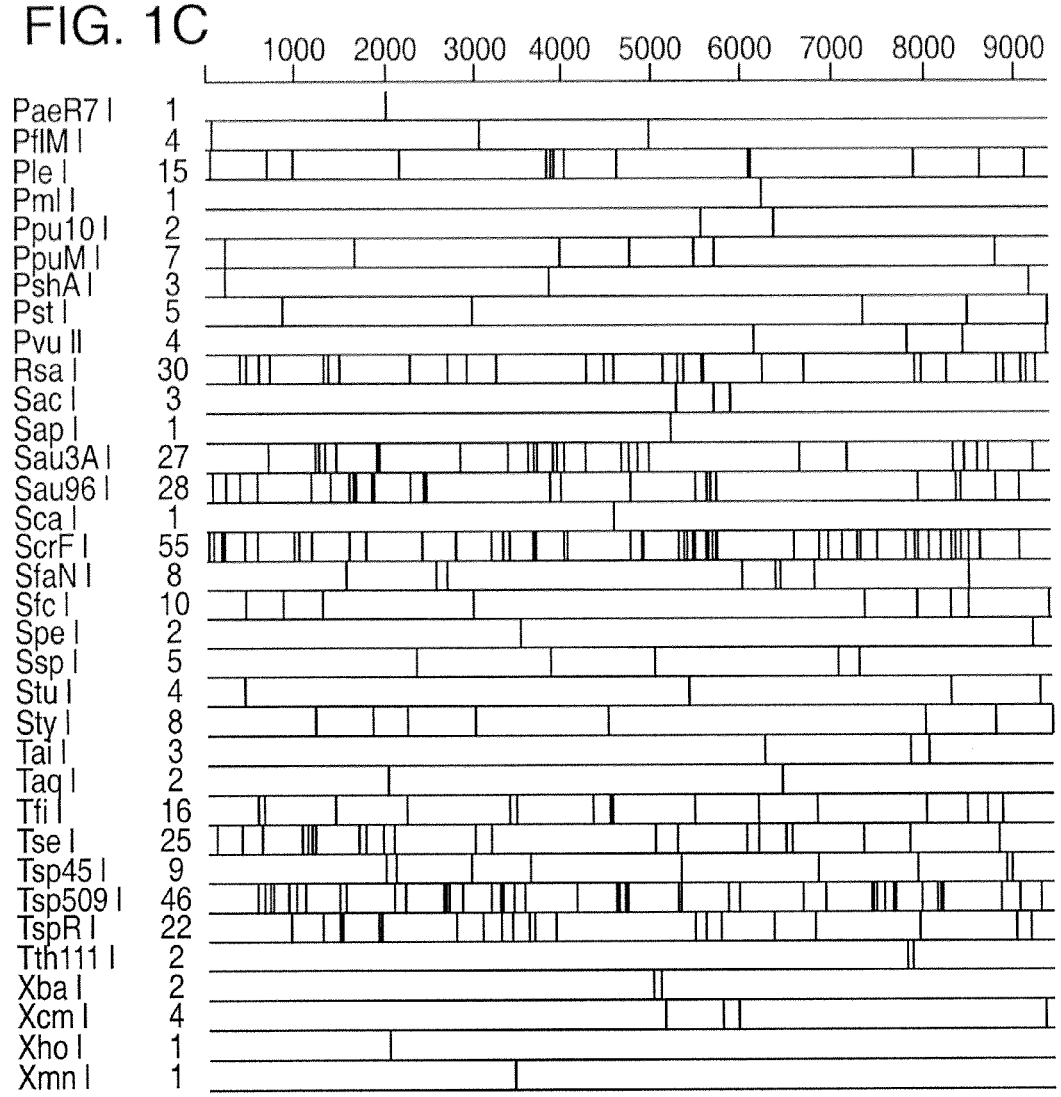

Deletions may be introduced using standard restriction vectors at appropriate sites. Sites may be selected using a restriction map of the pROD sequence (FIG. 1). Restriction may be done upon the provirus in situ, or for convenience, fragments of the pROD proviral vector that contain the SD and surrounding sequence, may be subcloned into a plasmid vector. The inserted nucleotides in such a subclone may be restricted or altered as desired, and then reinserted into an appropriately modified pROD clone. Clones thus constructed may then be confirmed by DNA sequencing.

The packaging vector thus produced will not be able to package its own genome, and is therefore not infective, but it will be able to package the genome of another virus that possesses the wild-type packaging sequence(s), for example, the transfer vector of the invention. The packaging vector may optionally be surrounded by a capsid to comprise a viral particle. The engineered proviral DNA packaging vector can be used to co-transfect cultured mammalian (e.g., human) cells in vitro or to produce a packaging cell line, as discussed below.

In another example, the packaging vector can be functionally and structurally divided into two parts. One part will be as described above, that is it will contain deletions upstream and downstream of the SD. In addition, it will also contain mutations or deletions which prevent the production of an envelope. The second part will provide the envelope only, thereby complementing the first.

The Transfer Vector

A transfer vector in this example is a nucleotide construct that delivers a transgene (for example a non-native gene) into a target cell. The transgene is then generally integrated into the genome of the target cell where it is expressed. The transfer vector contains the nucleotide sequences required for efficient packaging of its RNA genome (including the transgene) and can be made from an HIV-2 proviral clone, such as, for example, HIV-2/ST (Genbank Accession no.

M31113, Kumar et al., *J. Virol.* 64:890–901, 1990, which discloses the complete sequence of HIV-2/ST; Arya et al., *J. Acquir. Immune. Defic. Syndr.* 6:1205–1211, 1993; Arya et al., *AIDS Res. Human. Retroviruses.* 9:839–48, 1993). Alternatively, the transfer vector of the invention can be derived from the provirus of another retrovirus such as HIV-1 or SIV. Standard genetic engineering techniques can be used to manipulate the proviral genome.

In this example, it is illustrated that functional deletion of the SD site in the proviral genome of HIV-2 dramatically increases the encapsidation of the transfer vector genome, especially when the transfected cell is co-transfected with a packaging vector of the invention. This discovery is significant because it provides a retroviral packaging system with significantly enhanced packaging of transfer vector RNA and significantly reduced packaging of packaging vector RNA. These are important features for any retroviral gene therapy vector to have, particularly if the retroviral vector is derived from a pathogenic virus.

The SD portion of the genome can be functionally deleted in many ways. For example, the SD can be functionally deleted by changing the nucleotide sequence, by physical excision of all or part of the SD sequence, by a frameshift mutation, or by introduction of a foreign gene sequence within the SD sequence, for instance, a foreign gene sequence carrying a reporter molecule. Functional deletion also includes use of substitution mutants which disrupt the function of the SD, or any other mutation that disrupts the SD and enhances packaging of progeny transfer vector genomes. This effect is enhanced when the transfected cell is co-transfected with a packaging-defective packaging vector such as described herein. For instance, when human 293 cells are transfected with the transfer vector functionally deleted for SD and co-transfected with a packaging-defective HIV-2 genome, packaging of progeny transfer genomes is enhanced (for example by a factor of at least 2, 5, 10, 20 or even 30) in comparison to a co-transfection wherein the transfer vector is not deleted for SD.

A transfer vector can generally further possess a packaging signal and a transgene operably linked to a promoter. The transgene can be any gene that would provide an advantage if delivered to a target cell. Examples of transgene include, but are not limited to: cytosine deaminase in a subject suffering from SCID (severe combined immunodeficiency syndrome); HSV-TK in a subject having a tumor that is to be treated by the administration of ganciclovir; AADC in a subject suffering from Parkinson's disease; α-GAL-A in a subject suffering from Fabry disease; or a cytokine to a patient suffering from an infectious disease such as AIDS. The promoter for such a transgene can include promoters that can be regulated by an inducer or repressor, promoters that are constitutive, or promoters that show cell-type specificity. For example, the 5' HIV LTR promoter can be used that is induced in response to HIV infection. Such a promoter would be particularly useful if the transgene encoded a product that provided a treatment against HIV infection. Cell-type specific promoters can be advantageous for the treatment of various cancers, linked to an anti-tumor agent such as the herpes simplex virus thymidine kinase gene (HSV-TK). For example, the albumin and alpha-fetoprotein promoters tend to be liver-specific; the carbonic anhydrase I promoter is specific for colon cells; the prostate-specific antigen promoter is specific for prostate cells, and the villin, glucagon and insulin promoters are specific for pancreatic cells. Thus, linking an HSV-TK gene to a cell-type specific promoter would encourage expression of HSV-TK in the specific tissue targeted. In addition, the heterologous cytomegalovirus (CMV) promotor can also be used to allow the system to be used in a wide variety of cell types.

A transfer vector so constructed can be used to transfect cultured mammalian cells or producer cells co-transfected with a packaging vector, thus producing encapsidated transfer vector genomes that could be used to transfer a transgene into a target cell. The type of target cell susceptible to infection with such progeny virus will be dependent on the type of virus from which the packaging vector is derived, because infectivity is determined by the envelope proteins of the virus.

Cell Transfection to Produce Packaged Transfer Virus

The transfer and packaging vectors constructed as described herein can be used to transfect mammalian cells. Examples of cells that can be transfected include, but are not limited to: human epitheloid 293 or 293T cells, human lymphoid CEM cells, human SupT cells, human HeLa cells (ovarian epitheloid ATCC #CCL-2) human fresh PBMC cells (lymphocytes), human monocytic cells, such as U937 cells, human fibroblasts (such as HS27, ATCC # CRL-1634), normal human skin fibroblasts CD27sk (ATCC # CRL-1475), fetal brain cells (such as SVG (ATCC #CRL-8621), HFGC cells, and SVG-neural differentiated cells), glimoa cells (such as U281 and U373, ATCC # HTB-17) and human neuroblastoma cells (such as SKN-MC, ATCC # HTB-10 and SKN-SH). Such transfection will result in the production of a packaged transfer vector that can be used to transduce a target cell and thereby transfer a transgene into the genome of the target cell.

Transfection can be performed by routine methods whereby naked nucleic acids are transferred across the cell membrane thereby entering the interior of the cell where the proviral DNA can be subject to transcription and translation using the host's cellular machinery. For example, the naked proviral DNA can be transfected into the cell using the well-known calcium phosphate transfection method (see for example, EXAMPLE 9 and Arya et al., *AIDS Res. Hum. Retrovirus.* 9:839–48, 1993; Arya et al., *J. Acquir. Immune. Defic. Syndr.* 6:1205–1211, 1993). The conditions for transfection can be varied widely, for instance with regard to the amount of DNA applied and the components used in the medium to make the host cell membrane permeable to the naked DNA. The cells and supernatant from such a transfected cell culture can be harvested after a few days, for example 3–5 days. Such transfected cell cultures can be examined visually for syncytial formation, indicative of cytopathy. The number of virus particles in the supernatant can be estimated by the standard antigen capture assay scoring for the p27 core protein. Such methods are discussed, for example in EXAMPLES 1 and 2, and Arya et al., *Proc. Natl. Acad. Sci. USA.* 93:4486–4491, 1996 and in Al-Harthi et al., *AIDS Res. Hum. Retroviruses* 14:59–64, 1998.

Cells can also be transfected using DEAE-dextran (Arya, *New Bio.* 2:57–65, 1990; Arya and Sethi, *AIDS Res. Hum. Retroviruses.* 6:649–658, 1990), lipofectamine (as per the manufacture's instructions, GIBCO-BRL, Gaithersburg, Md.) or any other method used by those skilled in the art.

Production of Packaging Cell Lines

The packaging vector(s) of the invention can be used to produce a high efficiency packaging cell line. The packaging vector lacks nucleic acids required to package its own genome, but when introduced into a cell co-transfected with a transfer vector (or any virus that carries the wild-type packaging sequence), the transfer vector RNA genome will be packaged, resulting in virus particles capable of infecting target cells and transferring a transgene into such target cells. Such packaging cell lines can be derived from many cell types including, but not limited to, the HeLa cell line, human lymphoid cell lines (e.g., CEM cells), human embryonic kidney (HEK) cells such as 293 cells, or for example the cell lines listed above and described in EXAMPLE 10. Other techniques for making packaging cell lines are disclosed in PCT/US97/05272. Once stable transformed cell lines are made which express the lentiviral particles (for example HIV-1, HIV-2 or SIV), the transformed cell lines are transfected with the transfer vectors, which encode transgenes.

Infection of Target Cells By Progeny Virus

Target cells can be infected under standard culture conditions by the progeny virus of the invention. Target cells can be any cell type susceptible to infection by the virus from which the packaging vector was derived. For example, if the packaging vector is derived from HIV-2, the target cells can be lymphocyte cells such as $CD4^+$ T cells or macrophages. Progeny virus will be present in cell-free supernatants of infected producer cell cultures. This supernatant can be used as a source of progeny virus, and when target cells, for instance a monolayer of $CD4^+$ cells, are exposed to this supernatant, infection will occur within a few hours, for example 24 hours. After about five days, infected cells will display syncytia formation. The supernatant from these infected cells can be harvested for analysis and secondary virus production can be evaluated by p27 core antigen capture assays as described herein.

Analysis of Transgene Expression

Expression of the transgene in transfected cells can be evaluated by a variety of techniques including ELISA, Northern blot and other standard protein assays which allow one to determine that the transgene is being expressed (for example assaying for the conversion of L-dopa to L-dopamine after transfecting cells with the AADC gene). Transfected cells can be analyzed for cellular RNA by extraction of the RNA by standard methods, and by measurement of absorbance of light at set wavelengths. Northern blot and slot-blot hybridization can be used to quantify RNA.

Clones with Equivalent Nucleic Acids

Given the strategy for making the packaging and target packageable nucleic acids of the present invention, one of skill can construct a variety of clones containing functionally equivalent nucleic acids. Cloning methodologies to accomplish these ends, and sequencing methods to verify the sequence of nucleic acids are well known in the art. Examples of appropriate cloning and sequencing techniques, and instructions sufficient to direct persons of skill through many cloning exercises, are found in Berger and Kimmel, *Methods Enzymol* 152:307–16 (1987); Sambrook et al., *Molecular Cloning: A Laboratory Manual*, Cold Spring Harbor, N.Y., 1989, and Ausubel et al., in *Current Protocols in Molecular Biology*, Greene Publishing Associates and Wiley-Intersciences (1987).

The nucleic acid compositions of this invention, whether RNA, cDNA, genomic DNA, or a hybrid of the various combinations, are isolated from biological sources or synthesized in vitro. The nucleic acids of the invention are present in transformed or transfected whole cells, in transformed or transfected cell lysates, or in a partially purified or substantially pure form.

One skilled in the art will appreciate that many conservative variations of the nucleic acid constructs disclosed yield a functionally identical construct. For example, due to the degeneracy of the genetic code, silent variations (substitutions of a nucleic acid sequence which do not result in an alteration in an encoded polypeptide) are an implied feature of every nucleic acid sequence which encodes an amino acid. Similarly, conservative amino acid substitutions in one or a few amino acids in an amino acid sequence of a packaging or packageable construct are sequences substituted with different amino acids with highly similar properties.

It is also possible to generate other alterations in a given nucleic acid construct. Such well-known methods include site-directed mutagenesis, PCR amplification using degenerate oligonucleotides, exposure of cells containing the nucleic acid to mutagenic agents or radiation, chemical synthesis of a desired oligonucleotide, and other well known techniques. See Gilman and Smith, *Gene* 8:81–97, 1979; Roberts et al., *Nature* 328:731–734, 1987; Sambrook et al., *Molecular Cloning: A Laboratory Manual*, Cold Spring Harbor, N.Y., 1989; Innis et al., *PCR Protocols, A Guide to Methods and Applications*, 1990, Innis et al. (eds.), 21–27, Academic Press, Inc., San Diego, Calif.; and Ausubel et al., in *Current Protocols in Molecular Biology*, Greene Publishing Associates and Wiley-Intersciences (1987).

One of skill in the art can select a desired nucleic acid of the invention based upon the sequence provided and upon knowledge in the art regarding HIV generally. The life cycle, genomic organization (FIG. 2), developmental regulation and associated molecular biology of HIV viruses have been the focus of almost two decades of intense research. The specific effects of many mutations in the HIV genome are known. Moreover, general knowledge regarding the nature of proteins and nucleic acids allows one to select appropriate sequences with activity similar or equivalent to the nucleic acid sequences disclosed herein.

Finally, most modifications to nucleic acids are evaluated by routine screening techniques in suitable assays for the desired characteristics. For instance, changes in the immunological character of encoded polypeptides can be detected by an appropriate immunological assay. Modifications of other properties such as nucleic acid hybridization to a complementary nucleic acid, redox or thermal stability of encoded proteins, hydrophobicity, susceptibility to proteolysis, or the tendency to aggregate are all assayed according to standard techniques.

Packaging Vector Deletions

Specific examples, described below, will further illustrate the foregoing general teachings. In these examples, a vector system consisting of lentivirus genetic elements includes (i) a transfer vector that shuttles a transgene with the potential for regulation and for high-titer encapsidation and (ii) creation of a packaging cell line that encapsidates vector RNA but not the viral RNA encoding the packaging components and thus be substantially helper virus free. These examples characterize the packaging signal to permit the design of packaging vectors that express components needed for packaging, but without encapsidating the coding RNA (that is, without producing helper virus). These examples also illustrate the effect of additional leader sequence mutations, as well as the effect of the replacement of the 3'-LTR on expression and packaging. These examples further demonstrate that the packaging vector can be functionally and structurally divided into two vectors. The first vector is unable to produce a functional envelope, while the second vector complements the envelope defect.

Materials and Methods for Packaging Vector Construction

Proviral DNA Clones

Parental biologically active provirus molecular clone pROD-1 of HIV-2 (ROD) virus was first modified to obtain the clone termed pROD-3. This clone was obtained by inserting a synthetic linker with a multiple cloning site and a stop codon in the nef gene at a site 69 amino acids downstream of the nef initiator codon, thus truncating it and providing new cloning sites. The pROD-3 clone was phenotypically equivalent to the parental pROD-1 clone (Arya and Sadaie, *J. Acquir. Immune. Defic. Syndr.* 6:1205–1211, 1993; Arya and Mohr, *J. Gen. Virol.* 75:2253–2260, 1994). For introducing mutations in the leader sequence, a 5'-EcoR1- EcoR1 (nt 2658) fragment of pROD-3 was subcloned into a plasmid vector. The Bgl1 site (nt 502) of this subclone was used to create endonuclease Bal31 deletion mutants and an insertion of a synthetic BssH2 site, thus providing subclones with deletions downstream of the splice donor site (nt 470). The BssH site was then used to create upstream deletion mutants employing synthetic linkers with an additional Eag1 site at nt 305. The viral fragment from the selected subclones was reinserted into an appropriately modified pROD-3 clone. For molecular clones containing a puromycin resistance gene, the gene with or without a transcriptional termination (poly A) signal, was inserted at the engineered multiple cloning site in the truncated nef gene of pROD-3 clone. All mutant clones were confirmed by DNA sequencing.

Figure 4E:
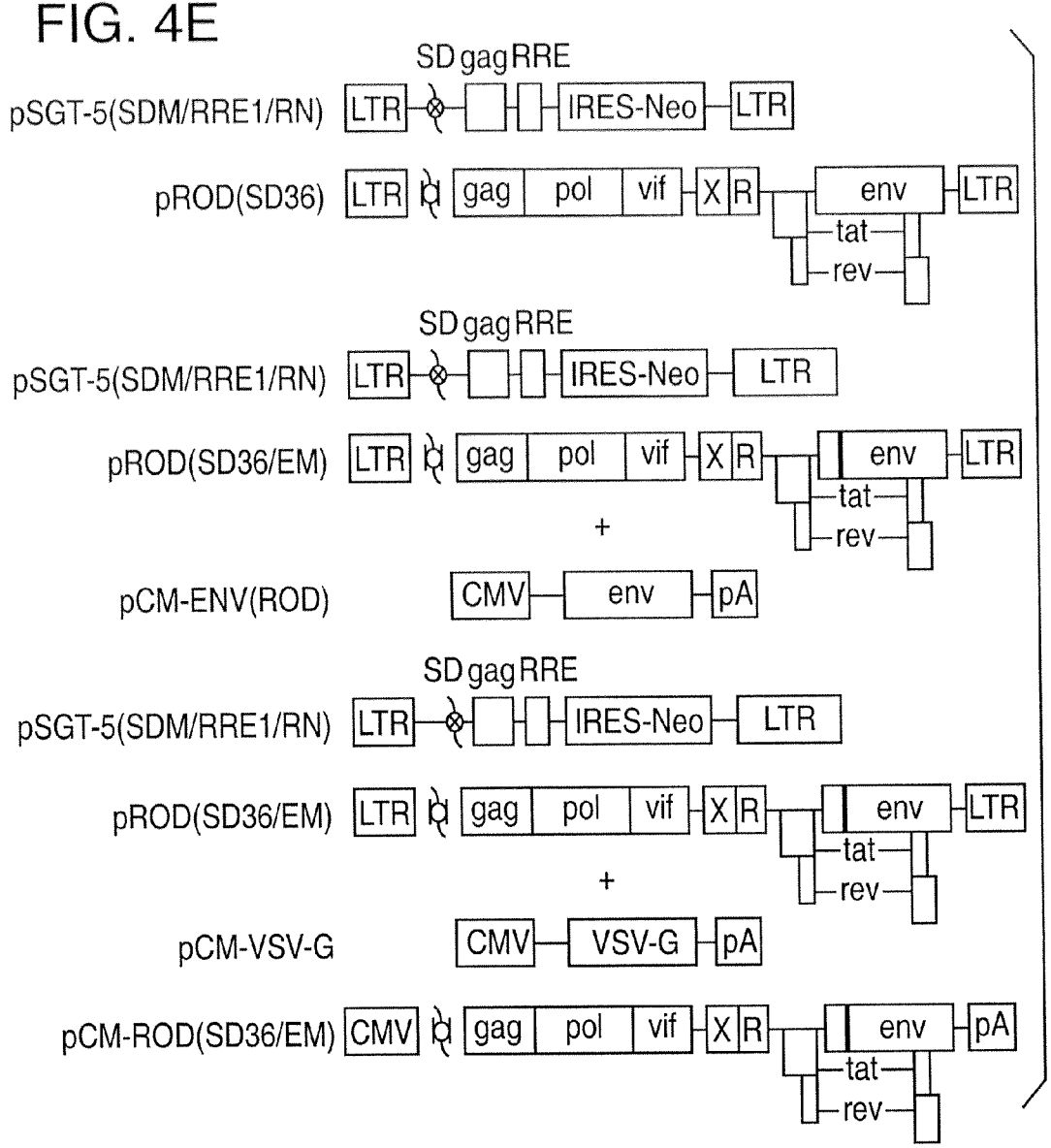

Examples of various deletions are shown in FIG. 3. pROD(PK36) shown in FIG. 3A (SEQ ID NO 2) contains a 54 nucleotide downstream deletion; pROD(SK36) shown in FIG. 3B contains a 153 nucleotide upstream deletion (SEQ ID NO 3); pROD(SD36) shown in FIG. 3C contains both a 153 nucleotide upstream deletion and a 53 nucleotide downstream deletion (SEQ ID NO 4); pROD(CG36) shown in FIG. 3D (SEQ ID NO 5) contains both a 88 nucleotide upstream deletion and a 53 nucleotide downstream deletion; pROD(MR36) shown in FIG. 3E (SEQ ID NO 6) contains both a 65 nucleotide upstream deletion and a 53 nucleotide downstream deletion.

pROD(SD36/EM) (SEQ ID NO 7) is identical to pROD (SD36) (SEQ ID NO 4); however, it also contains an insertion mutation in the envelope region as shown in FIG. 4A. To make this a vector with broader utility, other promotors, such as foreign internal promotors, can be used. For example, a CMV promotor can be used, such as pCM-ROD (SD36/EM) (SEQ ID NO 22) as shown in FIG. 4E. To be effective as a packaging vector, a vector which complements the envelope defect needs to be supplied. This complementing vector can include pCM-ENV(ROD) (SEQ ID NO 9) or pCM-VSV-G (Naldini et al., *Science.* 272:263–267, 1996) as shown in FIGS. 4B–D and 4E.

Similar packaging vectors can be generated using SIV using standard molecular biology methods. For example, an SIV equivalent of the HIV-2-based pROD(SD36), pSIV (SD36) (SEQ ID NO 11) is shown in FIG. 5B. This construct contains the functionally equivalent deletions upstream and downstream of the SD.

DNA Transfection and Antigen Capture Assays

For monolayers of epithelioid human embryonic kidney 293 or 293T cells (293 cells stably transformed with the T antigen) which were used interchangeably, $0.5$–$1.0 \times 10^6$ cells were transfected with 8–12 µg of proviral DNA using calcium phosphate transfection (see EXAMPLE 9 and Arya, *AIDS Res. Hum. Retroviruses* 9:839–848, 1993; Sadaie et al., *J. Med. Virol.* 54:118–128, 1998) and cells and culture supernatants were harvested 3 days later. Similar methods were used to transfect cell lines from several different origins (see EXAMPLE 10).

For suspension culture of human lymphoid CEM cells, $4$–$8 \times 10^6$ cells were transfected with 4–8 µg of proviral DNA by the DEAE-dextran protocol (Arya, *New Bio.* 2:57–65, 1990; Arya and Sethi, *AIDS Res. Hum. Retroviruses.* 6:649–658, 1990) and cells and culture supernatants harvested five days later. The CEM cultures were visually examined for syncytia formation before harvests. Virus particles in the supernatant were estimated by the standard antigen capture assay scoring for the p27 core protein (see EXAMPLES 1 and 2; Arya and Gallo, *Proc. Natl. Acad. Sci., USA* 93:4486–4491, 1996; Al-Harthi et al., *AIDS Res. Hum. Retroviruses* 14:59–64, 1998).

Infectivity Assays

To determine the infectivity of the progeny virus, aliquots of cell-free culture supernatants from transfected cultures were incubated with CEM cells for 2–4 hours, washed twice with PBS and once with complete culture medium, and incubated for five days. Cultures were visually examined for syncytia formation and supernatant harvested for analysis. Secondary virus production was evaluated by p27 core antigen capture assays (see EXAMPLES 1 and 2).

RNA Analysis

Cellular RNA was extracted by lysing cells with RNAzole (Tel-Test, Friendswood, Tex.) and RNA precipitated with isopropanol. The precipitate was dissolved, extracted with phenol-chloroform and re-ethanol precipitated. The precipitate was redissolved, treated with RNase-free DNase, extracted with phenol-chloroform and ethanol precipitated. For virus particle-associated RNA, clarified culture supernatant was pelleted through a column of 20% glycerol in TNE (10 mM Tris-HCl, pH 7.0; 0.15 M NaCl; 1 mM EDTA) by high speed centrifugation (Beckman SW41 rotor at 33,000 rpm for 1 hour). The pellet was lysed with RNAzole and viral RNA extracted and DNase-treated as described above.

The abundance of viral RNA was estimated by slot-blot hybridization (see for example, EXAMPLE 5). Aliquots of cellular RNA (usually, 10–20 µg) or viral RNA (usually half the initial amount) were denatured by heating RNA in 12×SSC—12% formaldehyde at 65° C. for 5 minutes followed by quick cooling. Denatured RNAs were further diluted with 15×SSC and two dilutions. (1:1 and 1:5) were slot-blotted onto nitrocellulose membranes and hybridized with [$^{32}$P] labeled virus probe. Virus-specific RNA was quantitated by integrating the intensity of the bands with a Phosphor-Imager (Molecular Dynamics, Sunnyvale, Calif.) and intensity expressed in arbitrary units.

Transfer Vector Deletions

The encapsidation of the transgene in the lentiviral vector, such as HIV-1 or HIV-2, is determined by the leader sequence based bipartite packaging signal. This encapsidation is thought to be enhanced by the gag sequence, provided the negative effect of the gag inhibitory sequence is overcome by the transregulatory RRE-Rev axis. Embedded in the packaging signal is a major splice donor site that the following examples show is not by itself essential for transgene encapsidation. Redesign of the transgene vector to contain a modified splice donor site, and the upstream and downstream packaging signal, resulted in efficient transgene encapsidation by an HIV-2 packaging vector. The modified transgene vector was also encapsidated by an HIV-1 vector pseudotyped with VSV-G protein. This modification did not adversely affect transgene expression.

The packaging signal of HIV-1 and HIV-2 is multipartite with sub-elements located upstream (exonic) and downstream (intronic) of the splice donor site in the leader sequence. Inclusion of the 5' end of the gag gene is thought to enhance RNA encapsidation (Luban and Goff, *J. Virol.* 68:3784–3793, 1994; Miller, *Retroviruses* 437–473, 1997; Parolin et al., *J. Virol.* 68:3888–3895, 1994; Schwartz et al., *J. Viral.* 66:151–159, 1992). However, the gag of HIV-1 contains inhibitory/instability or cis-acting repressive (INS/CRS) sequences. These sequences downregulate expression post-transcriptionally, in part by causing nuclear retention of the transcripts and promoting their splicing and/or degradation. This negative effect on expression can be overcome by providing RRE in cis and Rev in trans. EXAMPLES 5–9 and 17 report the unexpected finding that the splice donor of HIV-2 located in the leader sequence can use cryptic splice acceptors downstream in the vector to obtain high titer vector virus with lentiviral vectors.

Functionally equivalent transfer vectors can be generated with SIV using standard molecular biology methods. For example, an SIV equivalent of the HIV-2-based pSGT5 (SDM/RRE1) (SEQ ID NO 14), pSIV(SDM) is shown in FIG. 5C (SEQ ID NO 12). pSIV(SDM) contains the functionally equivalent mutation in the SD as generated in pSGT5(SDM/RRE1).

Materials And Methods for Transfer Vector Construction

Molecular Cloning

Figure 6A:
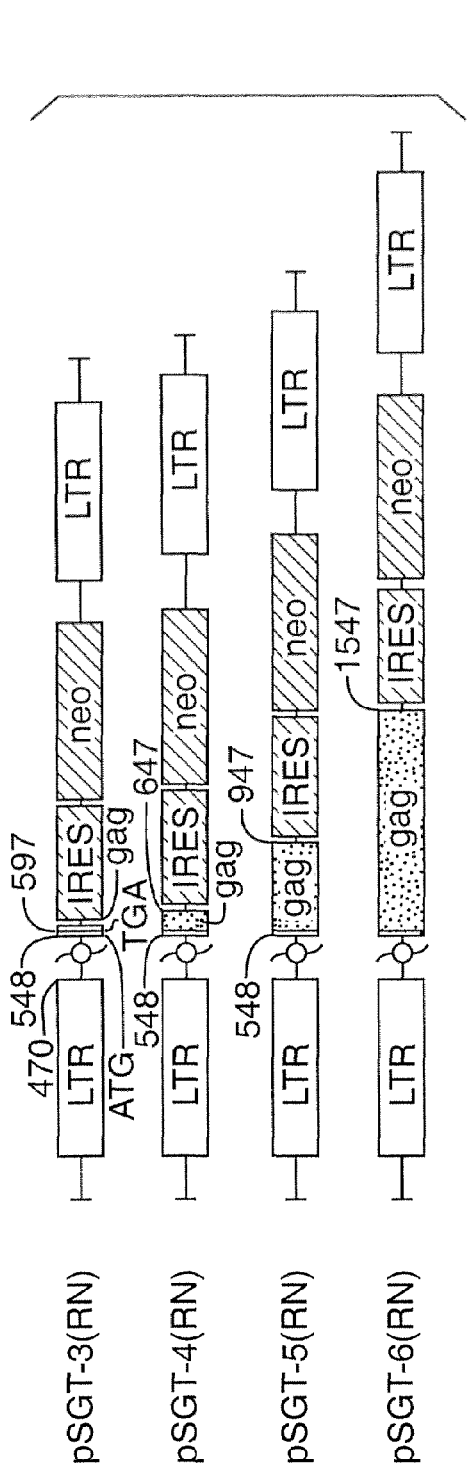
FIGS. 6A and B show the genetic structure of several HIV-2 transfer vectors (A) without or (B) with RRE sequences. The abbreviations represent the following: LTR, long terminal repeat; SD, splice donor; IRES, independent ribosomal entry site; neo, neomycin-resistance gene; and RRE, Rev response element. Clone pSGT(SDM) differs from clone pSGT-5(RRE) in having a modified splice donor site, denoted by a cross in the figure, which indicates a mutated or deleted SD that increases epcapsidation of the vector RNA.
Figure 6B:
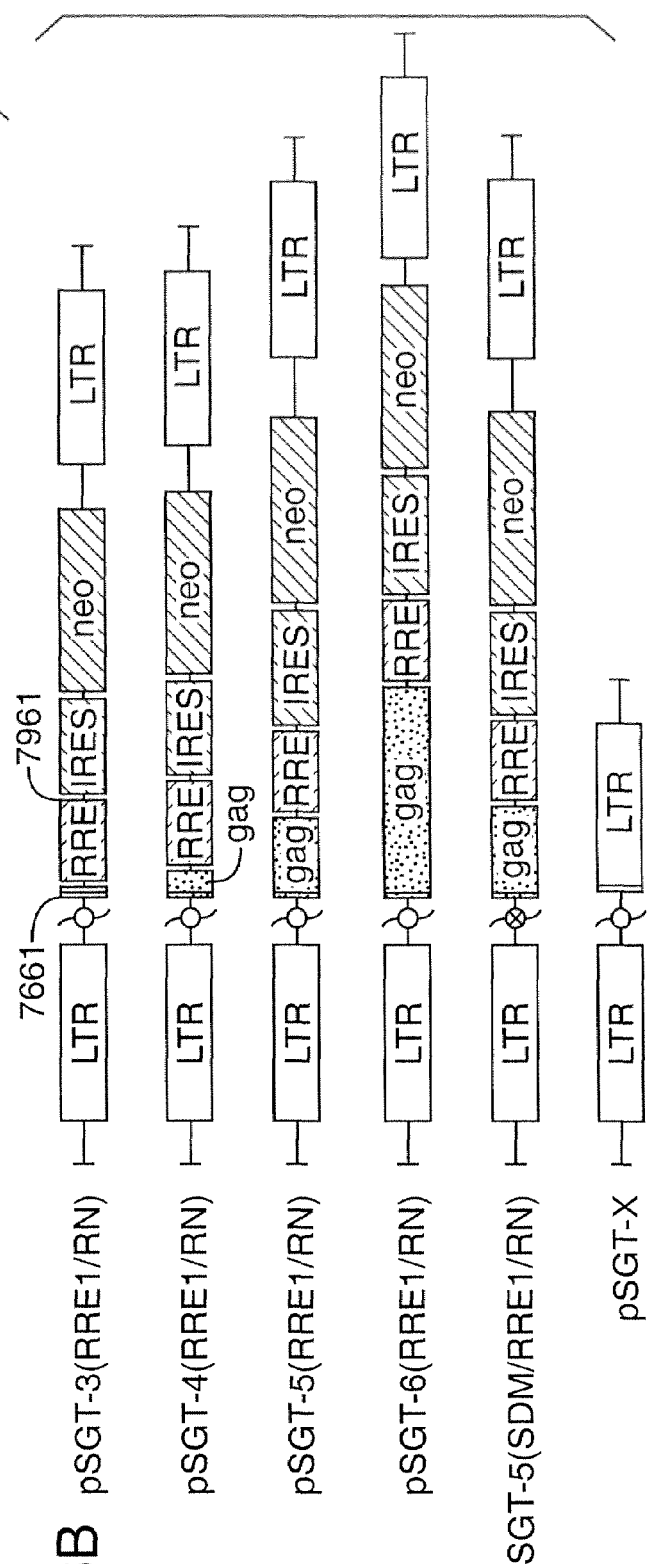

Basic vector (clone pSGT-1) was created by deleting the central portion (nt 505 to nt 8766) of a biologically active proviral clone of HIV-2(ST) (Genbank Accesion No. M31113; Arya, *J AIDS Res. Hum. Retroviruses.* 9:839–848, 1993; Arya et al., *Human Gene Ther.* 9:1371–1380, 1998; Kumar et al., *J. Virol.* 64:890–901, 1990) and insertion of a synthetic linker to reconstitute the leader sequence up to the gag ATG at nt 548 (clone pSGT-2). As shown in FIGS. 6A and 6B, this clone was used to create clones pSGT-3, pSGT-4, pSGT-5 and pSGT-6, which respectively contain an insertion of the first 50, 100, 400 and 1000 nucleotides of the gag along with a synthetic stop placed in frame immediately after the gag ATG initiation codon. To these clones, a synthetic linker (SL) with multiple cloning sites was added downstream of the gag sequence to obtain corresponding clones termed pSGT-X(SL).

As also shown in FIGS. 6A and 6B, a cassette of a picornavirus independent ribosomal entry site (IRES) linked to the marker neo gene (SEQ ID NO 15) was then inserted to create clones pSGT-X(RN) (FIG. 6A), which were further modified by the addition of a 300-nucleotide fragment of HIV-2(ST) RRE1 (SEQ ID NO 19; nucleotides 7661–7960 of Genbank Accession No. M31113) (FIG. 6B) (Dillon et al., *J. Virol.* 64:4428–4437, 1990) to create clones pSGT-X (RRE1/RN). RRE1 is also referred to herein as RR or RRE. Clone pSGT-5(SDM/RRE1/RN) (SEQ ID NO 14 with the neo gene inserted into the multiple coning site between nt 1835–1870), abbreviated as pSGT-5(SDM), was a substitution mutant of clone pSGT-5(RRE1) (SEQ ID NO 20 with the neo gene inserted into the multiple coning site between nt 1835–1870) where the splice donor site was mutated from GAAGTA (nt 1023–1028 of SEQ ID NO 20) to GATATC (nt 1023–1028 of SEQ ID NO 14) to make it diverge from the consensus (see FIGS. 7A–7F). The corresponding clones containing chemokine genes were similarly created by inserting the open reading frames and associated sequences of RANTES (C—C chemokine) or SDF-1 (C—X—C chemokine) cDNA clones. Clone pSGT-5(SDX/RRE1) (FIG. 7G) (SEQ ID NO 18) is identical to pSGT-5(SDM/RRE1/RN) except that the SD mutation is a deletion mutant instead of a substitution mutant. This clone can be created using standard cloning methods.

The wild type HIV-2 (ROD) proviral clone (pROD or pROD-3) and its truncated version pROD(SD36) has been previously described herein. Clone pROD(SD36) (SEQ ID NO 4) is a deletion mutant of clone pROD-3 where the subelements of the packaging signal located upstream and downstream of the splice donor have been deleted but the splice donor site itself is preserved. The HIV-1 and VSV-G vectors (Naldini et al., *Science.* 272:263–267, 1996; Zufferey et al., *Nature Biotech.* 15:871–875, 1997) were provided by the Salk Institute.

DNA Mediated Transfection

Cells, for example 293T cells and those shown in EXAMPLE 10, were transfected using calcium phosphate (see EXAMPLE 9 and Arya and Gallo, *Proc. Natl. Acad. Sci., USA* 93:4486–4491, 1996; Arya and Mohr, *J. Gen. Virol.* 75:2253–2260, 1994). Typically, 1×10⁶ cells from a subconfluent monolayer culture were transfected with 10 µg of vector DNA and 5–10 µg of cotransfecting DNA. Cultures were incubated with calcium-DNA aggregates overnight. Cells and culture supernatant were harvested at three days after transfection.

Protein and RNA Analysis

Transgene expression was measured as described in the Examples below. For example, neo gene expression in transfected cells was evaluated by ELISA assays. Cellular extracts were prepared, their protein content determined, and aliquots used to measure neomycin phosphotransferase activity with biotinylated neomycin phosphotransferase antibody and avidin-horseradish peroxidase conjugate (Sadie et al., *J. Med. Virol.* 54:118–128, 1998).

For cellular RNA analysis, transfected cells were lysed with the Trizol reagent (Life Biotechnologies, Gaithersburg, Md.) and RNA recovered by isopropanol precipitation. RNA was further purified by extraction with phenol-chloroform and re-ethanol precipitated. It was then digested with DNase in excess and re-extracted and ethanol precipitated. Cytoplasmic RNA was isolated by lysing cells in a hypotonic buffer and Trizol extraction. Recovery of RNA was quantitated by absorbance measurements. Viral RNA was prepared from partially purified virus particles which were pelleted through a column of 20% (v/v) glycerol by high speed centrifugation. The pellet was lysed with the Trizol reagent and viral RNA extracted and DNase treated as described above.

Abundance of vector RNA was estimated by slot-blot hybridization. Aliquots of cellular RNA (usually, 20 µg based on absorbance) or viral RNA (usually, half the amount of the total virus preparation) were denatured and two dilutions (1:1 and 1:5) were slot-blotted and hybridized with [$^{32}$P] labeled neo probe. For Northern blot analysis, about 20 µg of cellular RNA was electrophoresed in denaturing formamide-agarose gels. It was transferred to a nylon membrane by electroblotting and blot-hybridized with neo (or chemokine) probe. Abundance of RNA was quantitated by integrating the intensity of the bands with a Phosphor-Imager (Molecular dynamics, Sunnyvale, Calif.). Where applicable, membrane was subsequently probed with a virus specific probe. Filters containing cellular RNA were also sometimes reprobed with β-actin probe. Most results reported here represent multiple independent transfections done with cells at different passages.

EXAMPLE 1

Expression of Packaging Vectors in Human Epithelioid 293 Cells

Using the techniques described in the Materials and Methods for Packaging Vector Construction section above, two human cell lines, one epithelioid (293) and the other lymphoid (CEM), were tested. The cell lines were transfected with the molecular clones, and intracellular viral RNA and protein synthesis was measured to evaluate gene expression. To estimate helper virus production, extracellular release of particles containing viral RNA and proteins and their transmissibility was determined.

Expression

Figure 8:
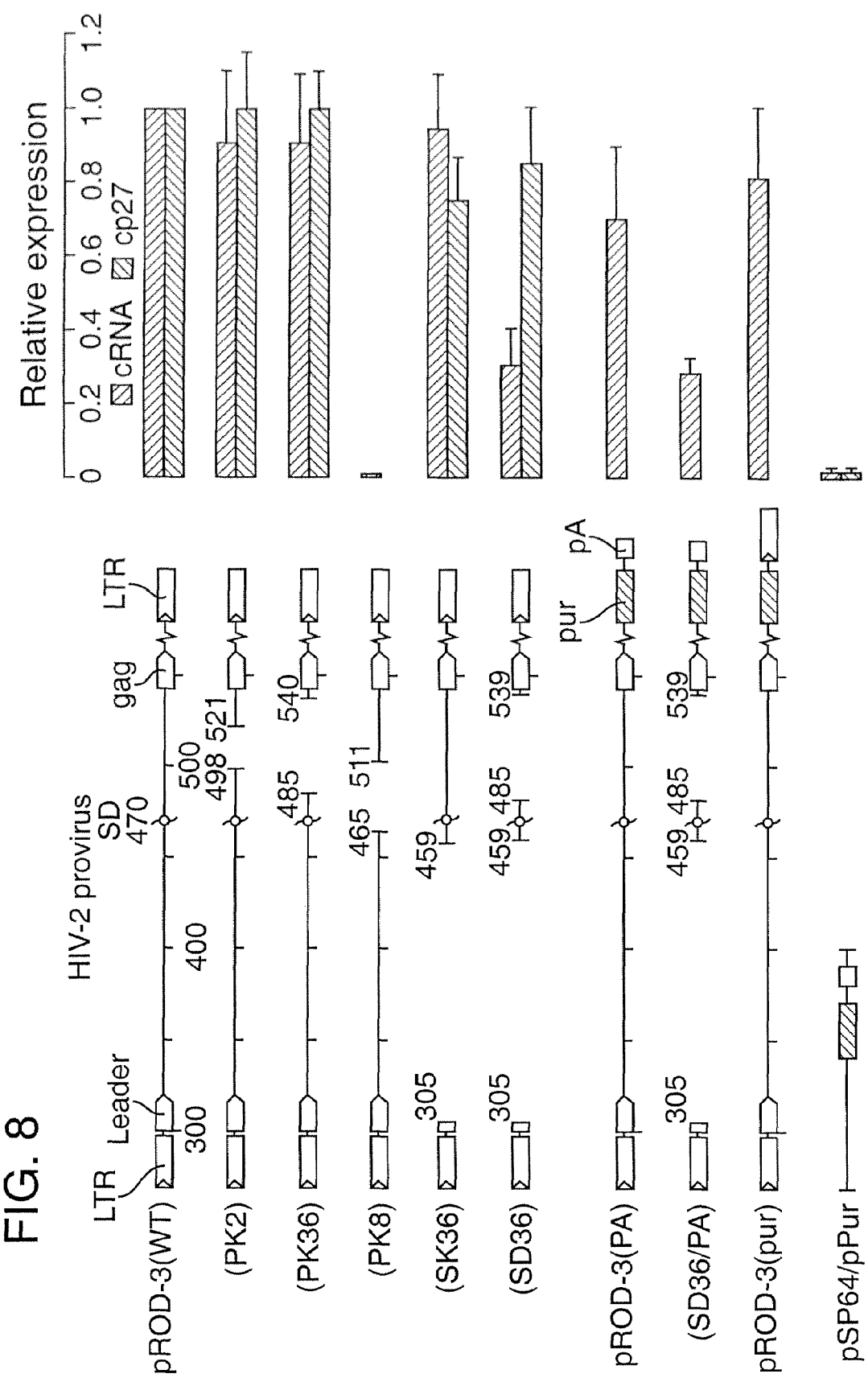
FIG. 8 illustrates the effect of leader sequence deletions on the expression of HIV-2(ROD) cellular RNA (cRNA) and intracellular p27 protein (cp27) in human epitheloid 293 cells.

FIG. 8 shows the measurement of intracellular viral RNA (cRNA) and protein expression (cp27) in cells transfected with the wild type and mutant HIV-2(ROD) clones containing deletions in the 5'-leader sequence.

Samples of RNA were slot-blotted onto a nitrocellulose membrane and hybridized with [$^{32}$P]labeled HIV-2 specific probe. Hybridization signals reflecting viral RNA abundance were quantitated using a Phosphor-Image analyzer (Molecular Dynamics, Sunnyvale, Calif.). The p27 levels were measured by an antigen capture (ELISA) assay. The intracellular levels of HIV-2 p27 antigen and RNA synthesized by mutant clones are expressed relative to the wild type clone. The p27 antigen level observed for wild type clone ranged from 30 to 50 ng/ml corresponding to about 0.1–0.5× 10$^6$ cells. In some cases the relative abundance of intracellular viral RNA was further confirmed by Northern blot hybridization and the results were similar to those obtained by slot-blot hybridization.

Expression of the mutant clone with a short deletion of 22 nucleotides (nt 499–520) located downstream of the major splice donor site at nt 470 and upstream of the gag ATG at nt 546 (clone PK2) was not much different than the expression of the wild type clone WT. No difference was observed either for viral RNA or viral protein synthesis (where protein synthesis was measured by the estimation of the p27 core antigen in the cellular extracts). Extension of the deletion to 54 nucleotides (nt 486–539) in this downstream region also did not affect the expression of vector RNA and proteins (clone PK36, FIG. 3A, SEQ ID NO 2). Similar results were obtained for the mutant clone with deletion (nt 306–458) upstream of the splice donor site (clone SK36, FIG. 3B, SEQ ID NO 3).

FIG. 8 shows that a deletion in the downstream region of HIV-2(ROD) of the size similar to that of the clone PK36, but extending into the splice donor site (clone PK8), had a detrimental effect on virus expression. Little or no viral RNA was detected in cells transfected with this clone. This is evidence for the importance of splicing in viral RNA processing and expression, and hence in its replication.

The clone containing deletions both downstream (nt 486–538) and upstream (nt 306–458) of the splice donor site in the leader sequence (clone SD36 in FIG. 8, also see FIG. 3C and SEQ ID NO 4) displayed diminished RNA expression relative to the wild type provirus (about one-half to one-third). This decrease was not exactly paralleled by the decline in intracellular core antigen accumulation. This can be related to the differences in the relative rates of synthesis and of half-lives of viral RNA and proteins.

The 3'-LTR provides signals for virus replication in addition to those for transcriptional termination. Thus, to minimize helper virus production, the 3'-LTR was replaced with a heterologous poly(A) signal sequence. Also, a drug resistance marker gene was included for cell selection (see SEQ ID NO 32). Thus, the 3'-LTR of selected clones was substituted with a puromycin-poly(A) cassette. Analysis showed that both the wild type and double deletion mutant could tolerate this substitution without a marked adverse effect on RNA expression relative to the parental unsubstituted clone. Similarly, the insertion of the puromycin gene at the nef site of the clone with an intact 3'-LTR was not detrimental for RNA expression.

In particular embodiments, it is desired that the deletion mutants decrease intracellular RNA expression by no more than 80%, and decrease intracellular p27 expression by no more than 20%.

Packaging

Figure 9:
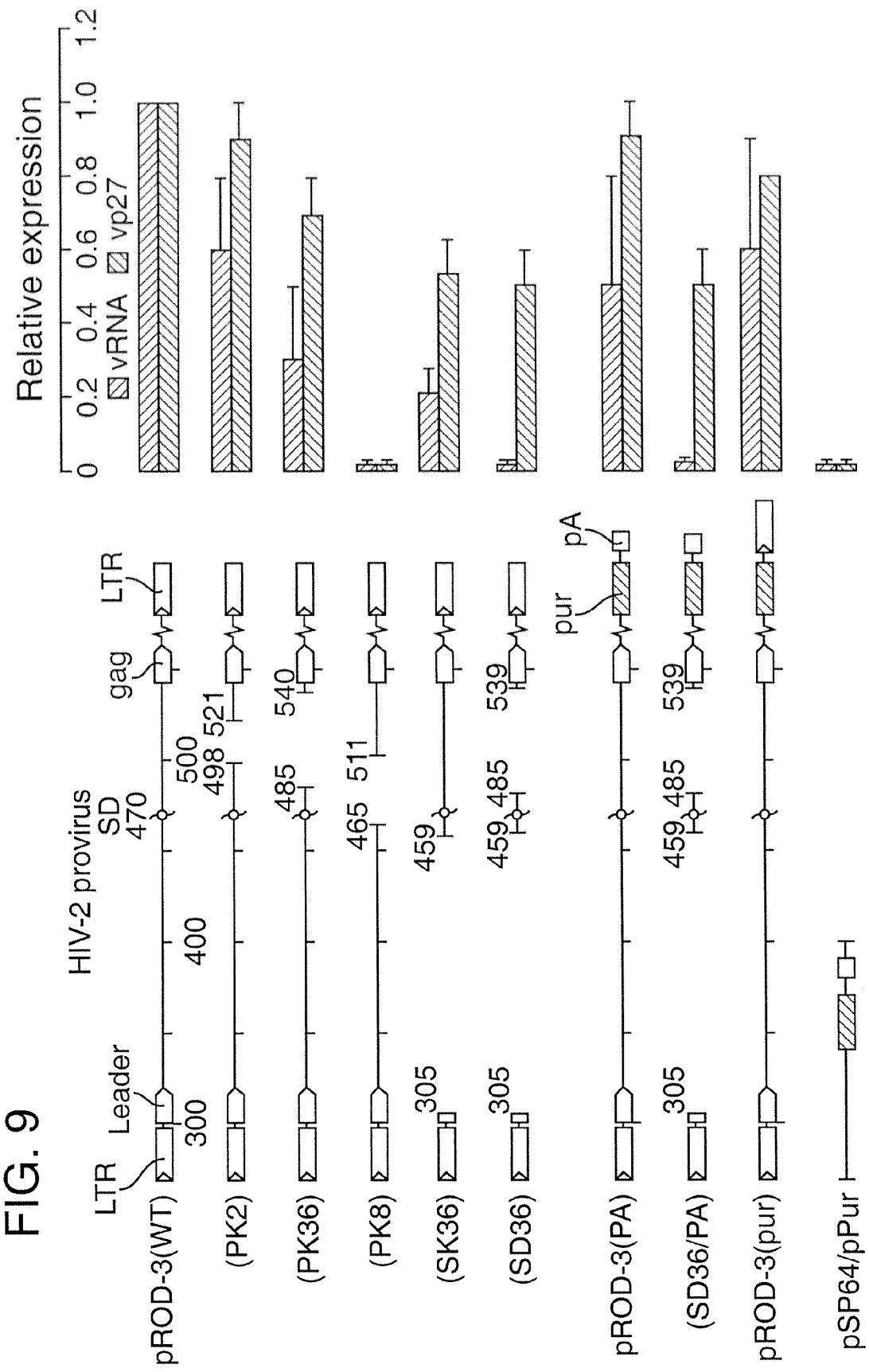
FIG. 9 illustrates the effect of leader sequence deletions in HIV-2(ROD) on the packaging of viral RNA (vRNA) and viral p27 protein (vp27) in human epithelioid 293 cells.

The effect of the same deletions and substitutions of the provirus on RNA encapsidation was measured. FIG. 9 shows a graph of the data for relative levels of viral RNA and core antigen in virus particles, which have not been normalized with respect to either the level of the intracellular viral RNA or the extracellular virus particles.

Cells were transfected with the DNA, culture supernatants were collected, an aliquot was used for p27 antigen determination, and the remaining supernatant was used for isolation of particle-associated viral RNA. Virus particles in the supernatants were collected by centrifugation through a column of glycerol. The pellets were lysed with RNAzole and RNA purified, including digestion with DNase. RNA was slot-blotted, hybridized with [$^{32}$P]labeled HIV-2 specific probe and quantitated. The data for mutant clones are expressed relative to the wild type clone. The level of supernatant p27 antigen ranged from 10 to 50 ng/ml. The amount of particle-associated RNA relative to that present in the cell for the wild type clone was roughly estimated to be 10% of the wild type.

The smaller deletion downstream of the splice donor site (clone PK2) did not affect virus particle production nor did it significantly affect RNA encapsidation. The larger deletion in this region (clone PK36, SEQ ID NO 2) reduced RNA encapsidation without significantly affecting virus particle production. The deletion of the upstream region (clone SK36, SEQ ID NO 3) seems to have a slightly greater effect on RNA encapsidation than the downstream deletion (clone PK36, SEQ ID NO 2). The deletion encompassing the splice donor site (clone PK8) reduced both virus particle production and viral RNA encapsidation. This was expected as this clone did not generate appreciable steady state levels of vector RNA inside the cell (FIG. 8). The clone with deletion of the leader sequence region both upstream and downstream (clone SD36, SEQ ID NO 4) displayed lowered virus particle production, but this reduction was only 30–50% of the wild type. In contrast, this clone was severely attenuated in its ability to encapsidate viral RNA, with a reduction of more than 80%, for example 90–95%.

Replacement of the 3'-LTR of this clone with the puromycin-poly(A) cassette did not further change its phenotype, it continued to produce appreciable levels of virus particles (greater than 40 or 50% of wild type) that were deficient in viral RNA (for example, less than 10% of wild type). Replacement of the 3'-LTR of the wild type clone with the puromycin poly(A) cassette (clone PA) resulted in about 50% reduction in the observed viral RNA encapsidation. A smaller degree of reduction in RNA encapsidation was also observed for the insertion of puromycin gene alone in the wild type provirus (clone PUR).

Helper Virus Production

To evaluate the presence of replication competent virus particles in supernatants of transfected cultures, the supernatants were used to infect $CD4^+$ CEM cells as targets and cultures monitored visually for syncytia formation and for progeny p27 core production (Table 1).

TABLE 1

Infectivity in CEM cells of progeny virus produced by Transfected 293 cells

| Clone | Syncytia Induction | Progeny p27 |
|---|---|---|
| pROD-3(WT) | +++ | 1.0 |
| (PK2) | +++ | 1.0 ± 0.0 |
| (PK36) | +++ | 0.6 ± 0.2 |
| (PK8) | (−) | 0.01 |
| (SK36) | + | 0.15 ± 0.05 |
| (SD36) | | 0.01 |
| pROD-3(PA) | + | 0.03 ± 0.02 |
| (SD36/PA) | | 0.01 |
| pROD-3(PUR) | ++ | 0.2 |
| pSP64/pPUR | (−) | (−) |

The supernatants from cultures transfected with clones PK2 and PK36 (SEQ ID NO 2) contained replication competent, syncytia inducing virus particles approaching the levels of cultures transfected with the wild type clone. The supernatants from clone SK36 (SEQ ID NO 3) transfected cultures were also positive for syncytia induction. Thus, neither upstream nor downstream deletion alone resulted in helper virus free phenotype. In contrast, supernatants from cultures transfected with clone SD36 were essentially negative for replication competent virus particles. However, the cultures secondarily infected with this supernatant sometimes presented evidence for visually observable but minimal syncytia formation. Syncytia formation was likely due to the infecting virus or to envelope protein, but not due to the production of infectious progeny virus. The phenotype of the particles contained in the supernatant of clone SD36/PA transfected cultures was similar to those from clone SD36 transfected cultures with rare, if any, syncytia induction. The insertion of the puromycin gene into the wild type (clone PUR) appeared to attenuate its ability to produce infectious transmissible virus particles. While RNA encapsidation phenotype of the clone PUR was about 70% of the wild type clone (FIG. 9), the transmissible infectivity of the particles produced by this clone appeared to be no more than about 20% of the wild type.

EXAMPLE 2

Expression of Packaging Vectors in Human Lymphoid CEM Cells

The effect of the leader sequence deletions was also determined as in EXAMPLE 1, but using human lymphoid CEM cells instead of 293 cells.

Expression

Cells were transfected with ROD leader sequence deletion mutant DNA using DEAE-dextran. Five days later, cultures were examined for the presence of syncytia and these were visually estimated in cultures transfected with mutant relative to those in cultures transfected with the wild type clone. Cells were harvested and processed for RNA isolation by the RNAzole procedure, including DNase digestion, and the abundance of virus-specific RNA determined by slot-blot hybridization.

Figure 10:
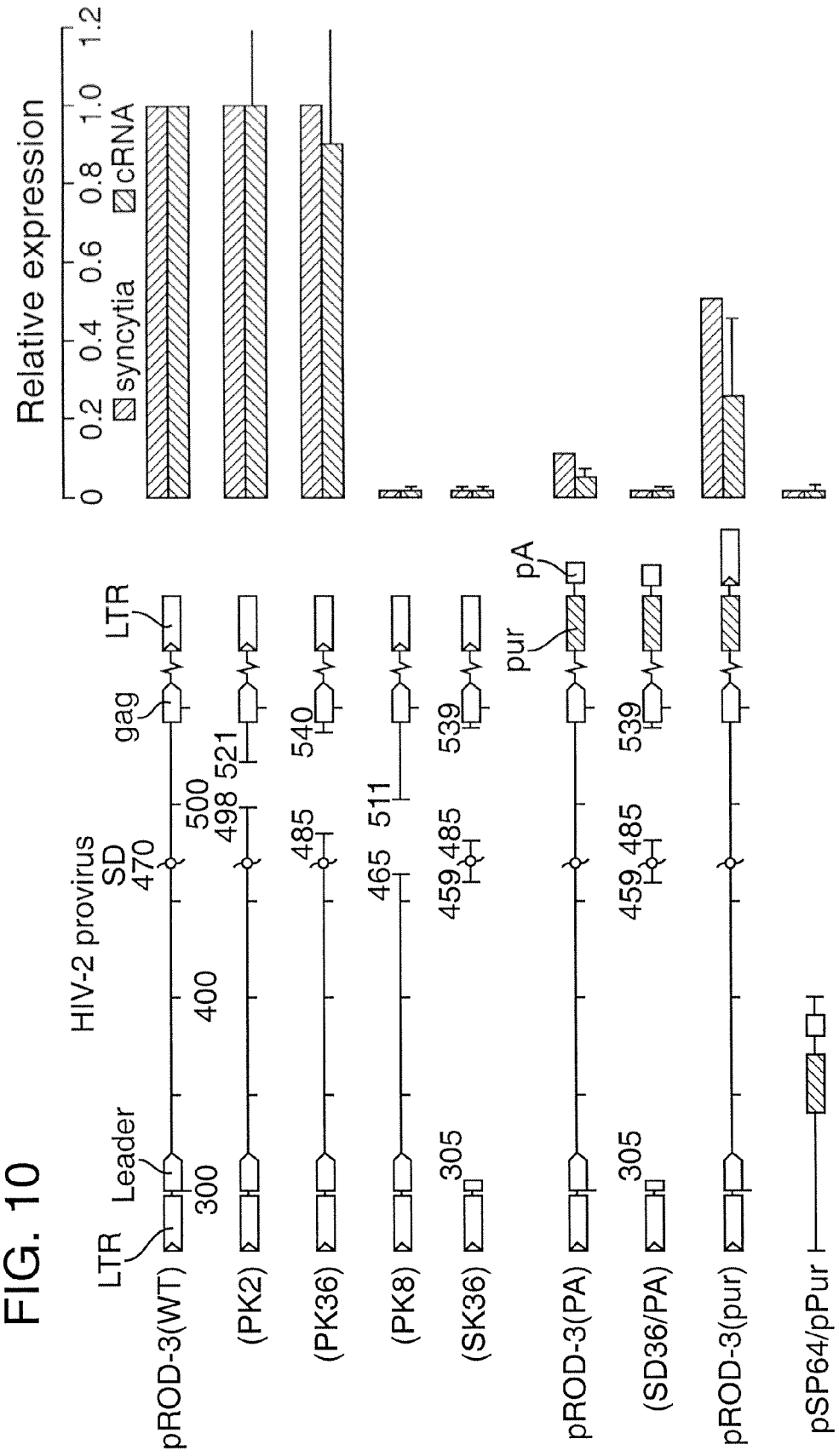
FIG. 10 illustrates the effect of leader sequence deletions on the expression of HIV-2(ROD) in human lymphoid CEM cells.

As shown in FIG. 10, the viral RNA expression and syncytia induction phenotype of mutant clone PK2 and PK36 (SEQ ID NO 2), with deletions downstream of the splice donor site, was only modestly different from that of the wild type clone in CEM cells. In some experiments, these mutant clones synthesized viral RNA which exceeded by 20–40% the level of viral RNA synthesized by the wild type clone. Clone PK8 with deletion of the splice donor site was inactive both transcriptionally and in syncytia induction. Clone SD36 (SEQ ID NO 4) with deletions both upstream and downstream of the splice donor site was severely attenuated in viral RNA synthesis but appeared not to be as severely attenuated in syncytium induction. The fact that this clone induced observable syncytia despite reduction in viral RNA abundance suggests that syncytium induction is not directly proportional to viral RNA synthesis. Substitution of the 3'-LTR with the puromycin-poly(A) cassette can have further attenuated the phenotype of this clone as clone SD36/PA was even less effective in syncytia induction than clone SD36. Insertion of the puromycin gene in the 3'-region at the nef site was also detrimental for the ability of the clone to synthesize or accumulate viral RNA and induce syncytium.

Packaging

Cells were transfected and extracellular particle-associated viral RNA (vRNA) and p27 antigen (vp27) was analyzed. The results for mutant clones are expressed relative to the wild type clone. The level of the supernatant p27 for the wild type clone was about 10 to 40 ng/ml. The estimated level of packaging of viral RNA relative to the intracellular viral RNA for the wild type clone was about 10%, a level similar to that observed with 293 cells.

Figure 11:
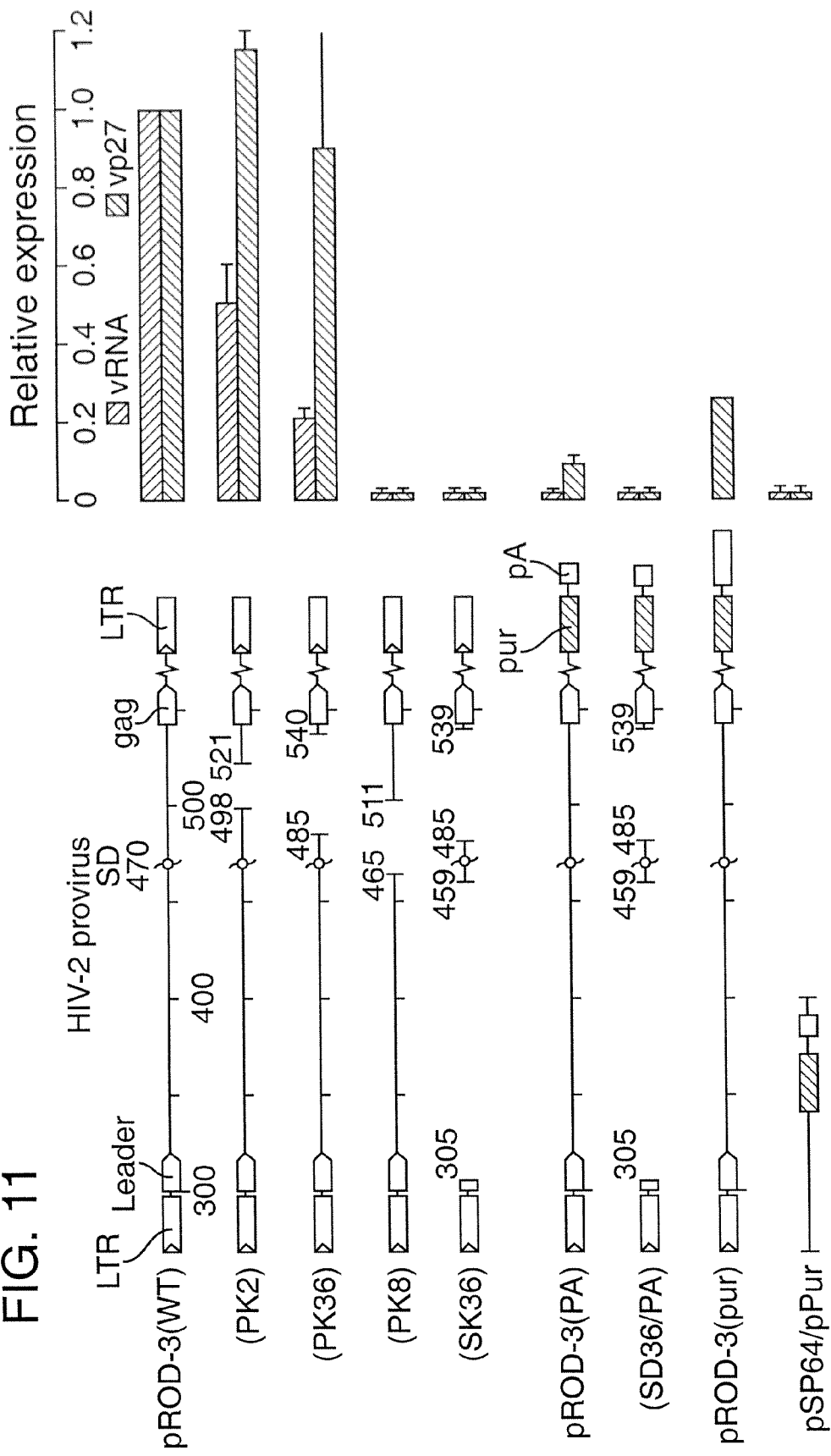
FIG. 11 illustrates the effect of leader sequence deletions on the packaging of viral RNA (vRNA) and proteins (vp27) of HIV-2(ROD) in human lymphoid CEM cells.

As shown in FIG. 11, while the deletion of the downstream region (clones PK2 and PK36) did not remarkably affect virus particle production, it had a noticeable effect on viral RNA packaging (Table 2).

TABLE 2

Infectivity in CEM cells of progeny virus produced by Transfected CEM cells

| Clone | Syncytia Induction | Progeny p27 |
|---|---|---|
| pROD-3(WT) | +++ | 1.0 |
| (PK2) | +++ | 0.4 0.2 |
| (PK36) | +++ | 0.2 0.1 |
| (PK8) | (−) | 0.01 |
| (SD36) | (−) | 0.03 |
| pROD-3(PA) | (−) | 0.7 |
| (SD36/PA) | (−) | 0.01 |
| pROD-3(PUR) | ND | ND |
| pSP64/pPUR | (−) | (−) |

For example, clone PK36 (SEQ ID NO 2) produced particles whose over-all viral RNA content was about one-third of those produced by the wild type provirus clones, suggesting that the mutant was producing more empty or RNA-deficient particles than the wild type clone. As expected, a mutant clone with the deletion of the splice donor site (clone PK8)

neither produced particles nor encapsidated viral RNA. Mutant clone SD36 (SEQ ID NO 4), with deletions upstream and downstream of the splice donor site, also did not produce virus particles or encapsidate viral RNA. Replacement of 3'-LTR with puromycin-poly(A) cassette (clone PA) had a marked detrimental effect on virus production and viral RNA encapsidation. Though this clone produced detectable level of virus particles, their RNA content was too low to be reliably measured by the assay used, which was not based on the PCR-amplification of the RNA. The clone with the upstream and downstream deletion as the well as replacement of the 3'-LTR with the puromycin-poly(A) cassette (clone SD36/PA) was essentially negative in its ability to produce viral particles or RNA. The insertion of the puromycin gene in the 3'-region of the wild type clone at the nef site (clone PUR) appeared to attenuate viral particle production. The phenotype of this provirus in CEM cells was not extensively investigated.

In summary, a specific deletion within the downstream elements but at a distance from the splice donor site did not significantly affect the expression of viral RNA or proteins either in human epithelioid or lymphoid cells. However, these downstream deletions did affect packaging, the magnitude of effect depended on the extent of deletion, with the larger deletion causing 40 to 80% defect in encapsidation relative to the wild type. Nonetheless, these mutant proviruses with the downstream deletions continued to produce unacceptable level of infectious virus particles. The fact that CEM cultures transfected with these mutants had a lower helper virus titer than transfected 293 cultures can be related to the amplification of the primary defect by further transmission of the wild-type but not the mutant clone, in $CD4^+$ CEM but not in $CD4^-$ 293 cells. Similarly, a deletion located exclusively upstream of the splice donor site had a detrimental effect on encapsidation (60–80% reduction) but was not helper virus free in its phenotype. Thus, sequence elements located both upstream and downstream of the splice donor site in the leader sequence contribute to RNA encapsidation, and neither one can be ignored in designing helper virus free packaging vectors and transfer vectors.

The effect of the combined upstream and downstream deletion on expression was more marked and appeared to depend on the cell type. In 293 cells, the combined deletions did not significantly affect the level of viral proteins, but caused a readily observed reduction in the steady-state level of viral RNA. The reason for the discrepancy is not clear, however, the combined deletions had the desired effect on packaging. Though the deletion was accompanied by some loss of virus particle production (up to 50% relative to the wild type), the particle thus produced contained little, if any, viral RNA. Hence, this mutant provirus produced RNA deficient helper virus particles with little or no infectivity. In contrast to 293 cells, the combined deletion was accompanied by an apparent attenuation of expression and consequently also of packaging in CEM cells. This could be due to poor transfection efficiency of the CEM cells and lack of amplification of mutant as compared to wild type clone. However, the CEM cells could be transduced along with a drug resistance selection gene, and selected from drug resistance. This technique will select cells that are also enriched for expression.

Notably, deletion of the splice donor site itself resulted in the dramatic reduction in the expression of viral RNA, independent of the cell type. The observation is consistent with the idea that RNA species destined for splicing, if not spliced, are degraded and not just restricted to the nuclear compartment (Schwartz et al., *J. Virol.* 66:150–159, 1992; Malim and Cullen, *Mol. Cell. Biol.* 13:6180–6189, 1993).

EXAMPLE 3

Heter 1 g us Transcriptional Termination Signal

To ensure that a packaging vector could be designed that was helper-virus free but maintained the capacity to express viral genes needed for in trans packaging, the requirement of the 3'-LTR for second strand synthesis, reverse transcription and virus transmission was exploited (FIGS. 8 and 9). Thus, the double deletion mutant provirus was further modified by the replacement of its 3'-LTR with a heterologous transcriptional termination signal. A puromycin resistance gene for eventual drug selection of the transduced cells was also included. This modification, pSP64/pPur, did not affect the expression capability of the vector, but further curtailed helper virus production. The replacement of the 3'-LTR with the puromycin-poly(A) cassette in wild type provirus, pROD-3(pur) was accompanied by a noticeable decline in viral RNA encapsidation.

EXAMPLE 4

Identification of Packaging Signal Sequences which are Necessary and Sufficient

To further define the sequences upstream and downstream of the SD that are necessary for packaging, other packaging vectors can be constructed. To identify the minimal amount of packaging sequence upstream from the SD that needs to be deleted to generate a functional packaging vector, vectors containing different lengths of upstream sequences can be generated. Shown in FIGS. 3D and 3E, pROD(CG36) (SEQ ID NO 5) and pROD(MR36) (SEQ ID NO 6) are packaging sequences which can be generated using standard cloning methods, which would help identify which sequences are necessary and sufficient for packaging. These two vectors contain more of the upstream SD sequences than pROD (SD36) (SEQ ID NO 4), while the downstream sequences are identical to pROD(SD36). Similar deletions can also be made downstream of the SD to identify the nucleotides necessary and sufficient for packaging. Furthermore, combinations of upstream and downstream deletions can be generated. The ability of these new packaging vectors to be expressed and packaged, for example in 293, CEM, or other cell line, is then tested as described in EXAMPLES 1 and 2. Clones containing the maximum number of nucleotides upstream and downstream of the SD, which express viral RNA but curtail RNA encapsidation and helper virus production, contain the minimal nucleotide deletions necessary for a functional packaging vector.

EXAMPLE 5

Expression or Transfer Vectors in Human Cells

Constitutive Expression

Human lymphocytic SupT cells were transfected with transfer vector clones (FIGS. 6A and 6B) and cellular extracts prepared to determine protein expression of the transgene neomycin (neo). Transfected cultures synthesized low but detectable levels of neo protein and RNA (data not shown). In addition, there was no marked difference in neo protein r RNA synthesis in cultures transfected with different vector clones.

The ability of the vector clones to program Neo protein and RNA synthesis in stably transfected cultures was also examined. The vectors were introduced into human lymphocytic SupT cells and selected for G418 (neo) resistance for several generations. Analysis of cells transduced with different vector clones again showed that they synthesized roughly equivalent amounts of Neo protein and Neo RNA (data not shown).

Induced Expression

The expression of Neo protein and RNA directed by the vector clones in the presence of transactivation provided by the HIV-2 provirus was also examined. For these studies, the replication competent HIV-2 provirus pROD-3, with functional regulatory and accessory genes (including rev) were used. The vector clones and provirus were co-transfected into 293T cells. Cotransfected cultures synthesized abundant quantities of Neo protein and Neo RNA (data not shown). The level of Neo protein and Neo RNA synthesized by vector clones was higher in the presence than in the absence of co-transfected provirus. This was expected as the provirus in co-transfected cultures will transactivate vector expression. The level of Neo protein and Neo RNA synthesized by different vector clones did not differ from each other significantly.

Transiently Transfected Cells

To determine if vector RNA in co-transfected cultures was encapsidated, virus particles in supernatant were partially purified and particle-associated RNA slot-blot hybridized with neo probe. Human epitheloid 293T cells were co-transfected with the vector and the wild-type HIV-2 proviral clone. Culture supernatants were harvested three days later and virus particles were partially purified by glycerol gradient centrifugation. Particle-associated RNA was analyzed for Neo RNA and viral RNA by slot blot hybridization with specific probes and for the content of viral p27 antigen using an antigen capture (Neo protein) assay.

As shown in Table 3, only a small fraction (less than 1%) of the Neo RNA in the cell was apparently packaged, and this did not differ among different vector clones. Similarly, all cultures encapsidated roughly equivalent amounts of viral RNA. Similar results were obtained when SupT1 cells stably transfected with vector clones were infected with HIV-2 virus. While the abundance of intracellular Neo RNA was increased relative to the uninfected cultures, only a marginal amount of Neo RNA was packaged into particles (not shown).

Figure 12:
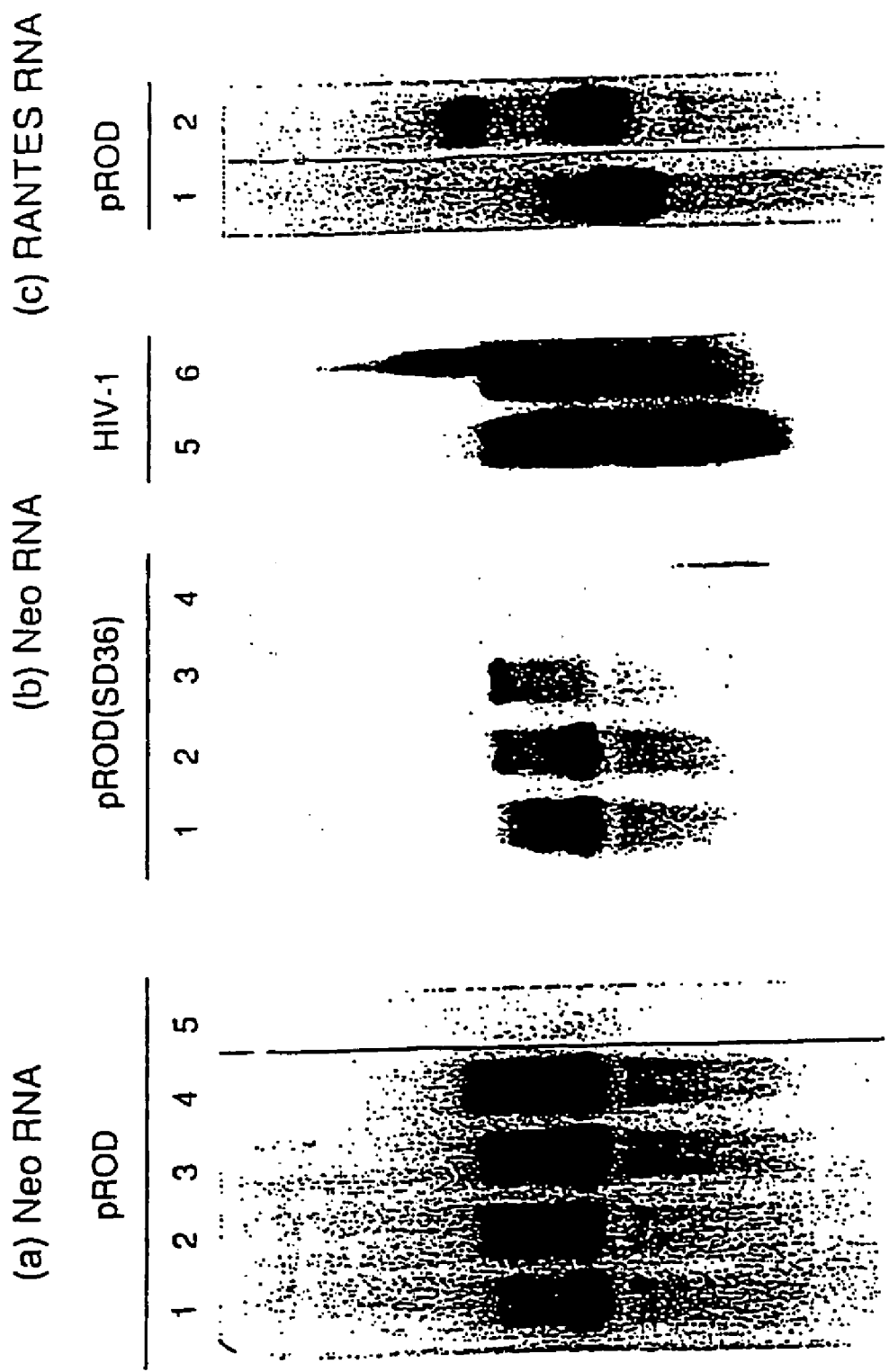
FIG. 12 shows a Northern assay illustrating processing of vector RNA in human epitheloid 293T cells. (a) Cotransfection with wild type HIV-2 proviral clone (pROD). RNA from cells transfected with: lane 1, pSGT-3(RN); lane 2, pSGT-5(RN); lane 3, pSGT-3(RRE); lane 4, pSGT-5(RRE), and lane 5, pSGT-3(SL). The size of the lower band in all lanes was about 2.0 Kb and that of the upper band was 2.9 Kb (lane 1), 3.2 Kb (lane 2), 3.2 Kb (lane 3), and 3.5 Kb (lane 4). (b) Co-transfection with mutant HIV-2 proviral clone pROD(SD36) (lanes 1–3) in which the splice donor site has been mutated, and HIV-1 (env) (lanes 5–6). RNA from cells transfected with lanes 1, pSGT-5(RN); lane 2, pSGT-5(RRE); lane 3, pSGT-5(SDM); lane 4, pSGT-5 (RRE); lane 5, pSGT(SDM); and lane 6. (c) Vector clone containing chemokine RANTES gene (lane 1) or IRES-neo (lane 2) co-transfected with wild type HIV-2 proviral clone pROD.

The neo specific RNA in transfected culture was further characterized by Northern blot hybridization (FIG. 12). Human 293T cells were co-transfected with the wild type HIV-2 provirus pROD as well as with the leader sequence mutant provirus pROD(SD36), which synthesizes viral proteins but produces RNA-deficient particles. Cellular RNA was subjected to denaturing gel electrophoresis, electroblotted and hybridized with neo or RANTES probe. Northern blot analysis of RNA from transfected cultures detected two predominant RNA species hybridizing with neo probe for all vector clones, except for clone pSGT-5(SDM) (see below). The RNA from cultures transfected with vector clone pSGT-3(RN) contained an RNA species of about 2.9 Kb and a second species of about 2.0 Kb. Similarly, RNA from cultures transfected with other clones, except clone pSGT-5(SDM), contained two RNA species. These were about 3.2 Kb and 2.0 Kb for pSGT-5(RN) and for pSGT-3(RRE), and about 3.5 Kb and 2.0 Kb for pSGT-5(RRE).

The size of the higher molecular weight RNA species for all vector clones was consistent with the size expected from the length of the transcriptional unit contained in them. The abundance of 2.0 Kb species was always higher (3–8 fold) than that of the higher molecular species. Sometimes a third species of intermediate size was also observed but its presence and abundance was not reproducible. When the blots were rehybridized with viral and β-actin probes, all lanes showed similar bands of equivalent intensities. The observation of two different size RNA species was not unique to vector containing neo transgene. Two species of RNA were also observed for vector carrying C—C chemokine RANTES gene (FIG. 12) or C13 X—C chemokine SDF-1 gene (not shown).

Splice Donor Mutant Vector

A second generation derivative of the vector clone pSGT-5(RRE1/RN) (SEQ ID NO 20 the neo gene inserted into the multiple coning site between nt 1835–1870) was created in which the splice donor site was mutated to render it non-functional, clone pSGT-5(SDM/RRE1/RN), (see FIGS. 6B and 7A and SEQ ID NO 14 with the neo gene inserted into the multiple coning site between nt 1835–1870). This clone was transfected into 293T cells in the presence of the wild type HIV-2 provirus clone pROD-3, the mutant provirus clone pROD(SD36) (SEQ ID NO 4) defective in RNA packaging and a combination of HIV-1(env⁻) and VSV-G clones. Cells were analyzed three days later for cellular neo and viral gene expression by slot-blot hybridization with a neo or virus-specific probe. As shown in Table 4, compared with the parental clone pSGT-5(RRE1/RN), mutation of the

TABLE 3

Encapsidation of vector RNA in Human 293T Cells

| | Constitutive Expression | | | Induced Expression and Encapsidation | | |
|---|---|---|---|---|---|---|
| | Neo Protein | | Neo RNA | Neo Protein | Neo RNA expression | Neo RNA encapsidation |
| | ng/ml | Relative* | Relative* | ng/ml | Relative* | Relative* | Relative* |
| pSGT-3 (RN) | 1.8 | 1.0 | 1.0 | 45.0 | 1.0 | 1.0 | 1.0 |
| pSGT-5 (RN) | 3.4 | 1.9 | 2.1 | 41.8 | 0.9 | 0.8 ± 0.2 | 0.5 ± 0.1 |
| pSGT-3 (RRE1) | 2.9 | 1.6 | 0.6 | 36.5 | 0.8 | 1.0 ± 0.2 | 1.0 ± 0.5 |
| pSGT-5 (RRE1) | 3.8 | 2.1 | 2.2 | 42.0 | 0.9 | 0.8 ± 0.4 | 0.9 ± 0.2 |
| pSGT-3 (SL) | 0.08 | <0.1 | <0.1 | 1.0 | <0.1 | <0.1 | <0.1 |

*Values are relative abundance levels.

splice donor, pSGT-5(SDM/RRE1/RN), did not significantly affect the ability of the vector to direct the synthesis of Neo protein or Neo RNA. However, the splice-donor mutant vector pSGT-5(SDM/RRE1/RN) enhanced encapsidation when transfected with pROD(SD36).

TABLE 4

Enhanced encapsidation using a splice donor mutant vector

|  | pROD | pROD (SD36) | HIV-2/VSV-G |
|---|---|---|---|
| Neo Protein expression |  |  |  |
| pSGT-5(RRE/RN) | 115 | 117 | 135 ± 48 |
| pSGT-5 (SDM/RRE1/RN) | 133 | 153 | 121 ± 28 |
| pSGT-5 (SL) | 1 | 12 | 0.1 |
| Neo RNA expression* |  |  |  |
| pSGT-5(RRE/RN) | 1.0 | 1.0 | 1.0 |
| pSGT-5 (SDM/RRE1/RN) | 0.8 ± 0.1 | 0.8 ± 0.4 | 0.6 ± 0 |
| pSGT-5 (SL) | <0.1 | <0.1 | <0.1 |
| Neo RNA encapsidation* |  |  |  |
| pSGT-5(RRE/RN) | 1.0 | 1.0 | 1.0 |
| pSGT-5 (SDM/RRE1/RN) | 1.9 ± 0.5 | 16.1 ± 4.3 | 2.3 ± 0.4 |
| pSGT-5 (SL) | <0.1 | <0.1 | <0.1 |

*Values shown are relative RNA abundance levels.

The nature of the RNA synthesized by the parental and mutant clones was also analyzed by Northern blot hybridization (see FIG. 11). In contrast to the parental clone which synthesized two species of Neo RNA (about 3.5 and 2.0 Kb), the mutant clone synthesized one predominant species of about 3.5 Kb. When the supernatant particles (partially purified by glycerol gradient centrifugation) produced by the transfected culture were examined, the phenotype of the parental and mutant clone was different (Table 5).

TABLE 5

|  | % Neo RNA Encapsidated | | |
|---|---|---|---|
|  | HIV-2 (ROD) | HIV-2 (ROD/SD36) | HIV-1/VSV-G |
| pSGT-5 (RRE/RN) | 1.7 ± 0.9 | 2.5 ± 1.6 | 14.6 ± 6.3 |
| pSGT-5 (SDM/RRE1/RN) | 4.3 ± 2.8 | 24.8 ± 11.6 | 30.7 ± 5.7 |
| pSGT-5 (SL) | <0.1 | <0.1 | <0.1 |

As shown in Table 5, in the presence of the wild type HIV-2 proviral clone HIV-2(ROD), about 2% the total transgene Neo RNA synthesized by the parental pSGT-5 (RRE1/RN) clone was associated with the particles, and was about 4% for the mutant vector pSGT-5(SDM/RRE1/RN) clone. In the presence of mutant HIV-2 provirus defective for viral RNA encapsidation (pROD/SD36), the fraction of total Neo RNA in particles for the parental clone pSGT-5RRE was about 2.5%, and this fraction for the mutant clone pSGT-5(SDM) rose to about 25%. With HIV-1/VSV-G packaging vector combination, about 15% and 30% of Neo RNA synthesized by the parental and mutant clones was associated with the virus particles. These differences between the two vector clones were not related to any obvious features of the experimental protocol. Reprobing of RNA blots with virus-specific probe showed that for a given provirus, there was an equivalent amount of viral RNA on the blots. As expected, particle-associated RNA from cultures cotransfected with the mutant provirus clone pROD (SD36) contained little, if any, viral RNA. These blots were not probed with an HIV-1 viral probe. Reprobing the blots with a β-actin probe showed the slots to contain similar amounts of cellular RNA.

It has previously been reported that a part of the gag sequence is thought to increase encapsidation efficiency and/or selectivity. However, this region of gag of HIV-1, and presumably of HIV-2, had been thought to contain intragenic INS/CRS sequence elements which cause nuclear retention of the transcripts, thus curtailing their availability in the cytoplasm for packaging as well as for the expression of the attached transgene. In the past, this block has been overcome by providing RRE in cis and Rev in trans. However, in the present invention, it has been discovered that the presence of gag sequence in HIV-2 did not have a notable effect on expression of the attached transgene. This was irrespective of whether or not the vector contained RRE in cis and had the Rev provided in trans. Furthermore, despite the presence of leader and gag sequences, RNA synthesized by several vector clones was minimally packaged.

HIV-2 vector RNA was also efficiently encapsidated by the HIV-1 packaging system using VSV-G pseudotyping. There was a 2-fold difference between the parental and the splice donor mutant vector in this case. The results also demonstrate that the splice donor sequence itself is not required for packaging or transgene expression. Notably, the ability to encapsidate HIV-2 vectors in HIV-1 packaging system provides an additional margin of safety. The sequence dissimilarity between HIV-1 and HIV-2 will curtail generation of helper virus by homologous recombination during vector production. There are additional advantages of HIV-2 vectors in comparison to HIV-1 vectors. The desirable karyophilic nuclear import function of HIV-2 is encoded by the single function Vpx. This function in HIV-1 is encoded by Vpr, which also has the undesirable cell cycle arrest function. In addition, animal models for testing HIV-2 vectors exist which may not be available for HIV-1 vectors. Also, HIV-2 is generally less pathogenic than HIV-1, thus providing better biosafety. For gene therapy of HIV-1 infection, HIV-2 vectors will be better as they are less likely to generate recombinants with the resident HIV-1 genome. Moreover, HIV-2 is believed to downregulate HIV-1.

EXAMPLE 6

Two-vector Packaging System

As described above in EXAMPLES 1 and 2, packaging vectors were generated by deleting sequences upstream and downstream of the SD site. To further minimize helper virus production, the pROD(SD36) (SEQ ID NO 4) packaging vector was split in a way that its functions were encoded by two different plasmids.

The first vector, pROD(SD36/EM) (FIG. 4A and SEQ ID NOS 7 and 21) provides all the functions except the envelope. This vector is identical to pROD(SD36) (SEQ ID NO 4), except that it contains an insertion mutation in the envelope region, rendering the envelope non-functional (see FIG. 4A). Functional equivalents can be generated by deletions, substitutions, frameshift or other mutations in this envelope region. In addition, the 5' LTR can be replaced with a foreign internal promotor (such as the CMV promotor) and 3' LTR with a heterologous polyadenylation signal (FIG. 4E and SEQ ID NO 22) to allow the vectors to be used in a wider variety of cell types.

The second vector, for example pCM-ENV(ROD) (FIG. 4B–4D and SEQ ID NO 23) or pCM-VSV-G (FIG. 4E, Naldini et al., *Science.* 272:263–267, 1996, GenBank Accession No. AF105229), compensates for the defect of pROD (SD36/EM) by providing the envelope in trans.

The ability of the three vector system to encapsidate viral RNA was compared to the two vector approach described in EXAMPLE 5. As described in EXAMPLE 5, 293T cells were transfected with the vectors as shown in Table 6. Cells were analyzed 3 days later for their ability to package viral RNA.

TABLE 6

HIV-2 Vector Packaging by Split-Genome Packaging Vectors

| | % Vector RNA Encapsidated | |
|---|---|---|
| | HIV-2 pROD (SD36) | HIV-2 pROD (SD36/EM) + pCM-ENV (ROD) |
| pSGT-5 (RRE1/RN) | 1.1 | 5.3 |
| pSGT-5 (SDM/RRE1/RN) | 9.4 | 29.7 |

As shown in Table 6, both the single packaging vector (SD36) and the two-vector packaging system [SD36/EM (SEQ ID NO 21)+pCM-ENV(ROD) (SEQ ID NO 23)] efficiently encapsidate viral RNA in the presence of the transfer vector pSGT-5 (SDM/RRE1/RN) (SEQ ID NO 14 with the neo gene inserted into the multiple coning site between nt 1835–1870). These results indicate that the safer-spit genome vector strategy can be used without decreasing packaging efficiency.

EXAMPLE 7

Effect of RRE Length on Transgene Expression

This example describes experiments conducted to further investigate the role of the SD site on expression of a transgene, and thus the titer attainable. In this example, the length of the RRE was varied in the transfer vector, containing the neo transgene (the nucleic acid sequence for neo is available from Genbank: nt 3596–4390 of Accession No AB003468). The identical packaging system containing pROD(SD36/EM) (SEQ ID NO 21) and the VSV-G envelope vector (pCM-VSV-G vector shown in FIG. 4E and described in EXAMPLE 6) was used to test each transfer vector.

The vector pSGT-5(RRE1/RN) (shown in FIG. 6B and SEQ ID NO 20 with the neo gene inserted into the multiple coning site between nt 1835–1870) which contains the neo gene (RN) and the wild-type splice donor (SD), was modified to contain one of two different lengths of RRE. The vector pSGT-5(RRE1/RN) (FIG. 6B) contains an RRE of 300 nucleotides (SEQ ID NO 19), while the vector pSGT-5(RRE2/RN) (SEQ ID NO 20 with the neo gene inserted into the multiple coning site between nt 1835–1870 and the RRE2 sequence shown in SEQ ID NO 24) contains an RRE of 530 nucleotides (SEQ ID NO 24). Using the methods described below, the level of neo gene expression for three different transduction vectors was measured, and the viral titer calculated for each.

Using the methods described in EXAMPLES 5 and 9, 293T cells were co-transfected with the pROD(SD36/EM) (SEQ ID NO 21) packaging vector, the VSV-G envelope vector, and serial dilutions of the lentiviral-neo vectors (see Table 7). At 48 hours post infection, cell lysates were prepared by freeze-thawing the cells in the presence of 1.0 mM PMSF (Sigma, St. Louis, Mo.). The protein levels were determined by assaying the crude cell lysates for Neomycin Phosphotransferase II (NPT II) using a sandwich ELISA assay. First, 96 plate microwells were coated with rabbit polyclonal antibody specific for NPT II (5Prime-3Prime, Inc., Boulder, Colo.) for two hours, followed by incubation with a blocking buffer (5Prime-3Prime, Inc., Boulder, Colo.) for 30 minutes. Dilutions of the cell lysates, standards, controls and a blank were added to individual wells and then incubated for two hours. The cells were subsequently washed and biotinylated anti-NPT II (5Prime-3Prime, Inc., Boulder, Colo.) was added and incubated with the cells for one hour. The wells were washed and a streptavidin alkaline phosphatase solution was added. This reaction was incubated for 30 minutes followed by a 20–30 minute room temperature incubation with AP-substrate p-nitrophenyl phosphate for color development. The wells were then read at 405 nm using a Bio-Rad System (Bio-Rad Laboratories, Hercules, Calif.) against the reagent blank. From this value the number of neo-resistance colonies was determined.

As shown in Table 7, the length of the RRE had no affect on the titer obtained, and thus no affect on neo gene expression. However, modification of the vector to functionally delete the SD (pSGT-5(SDM/RRE1/RN); see FIG. 6B and SEQ ID NO. 14 with the neo gene inserted into the multiple coning site between nt 1835–1870) as described in EXAMPLE 5, enhanced the titer by approximately 30-fold. The titer shown in Table 7 is that for unconcentrated virus.

These results demonstrate that the length of the RRE has less effect on expression of the transgene, such as neo, than does the functional deletion of the SD site. Functional deletion of the SD enhances expression of the transgene incorporated into the transducing vector.

TABLE 7

Lentivirus-Neo Vector Transduction of Human 293T Cells

| Transducing vector | Packaging vector (core) | Envelope | Titer (neo$^R$/ml) |
|---|---|---|---|
| pSGT-5 (RRE1/RN) | pROD(SD36/EM) | VSV-G | $1.4 \pm 0.7 \times 10^4$ |
| pSGT-5 (RRE2/RN) | pROD(SD36/EM) | VSV-G | $1.6 \pm 1.0 \times 10^4$ |
| pSGT-5 (SDM/RRE1/RN) | pROD(SD36/EM) | VSV-G | $4.7 \pm 2.6 \times 10^5$ |

EXAMPLE 8

Expression of GFP

This example describes experiments conducted to demonstrate that other transgenes can be inserted into the lentiviral transfer vector, and be expressed. Specifically, the ability of several different transducing vectors to drive the expression of green fluorescent protein (GFP) (SEQ ID NO 25) in the presence of the pCM-ROD (SD36/EM) packaging vector (see FIG. 4E and SEQ ID NO 22) and VSV-G envelope vector (see EXAMPLE 6) was investigated.

Figure 14:
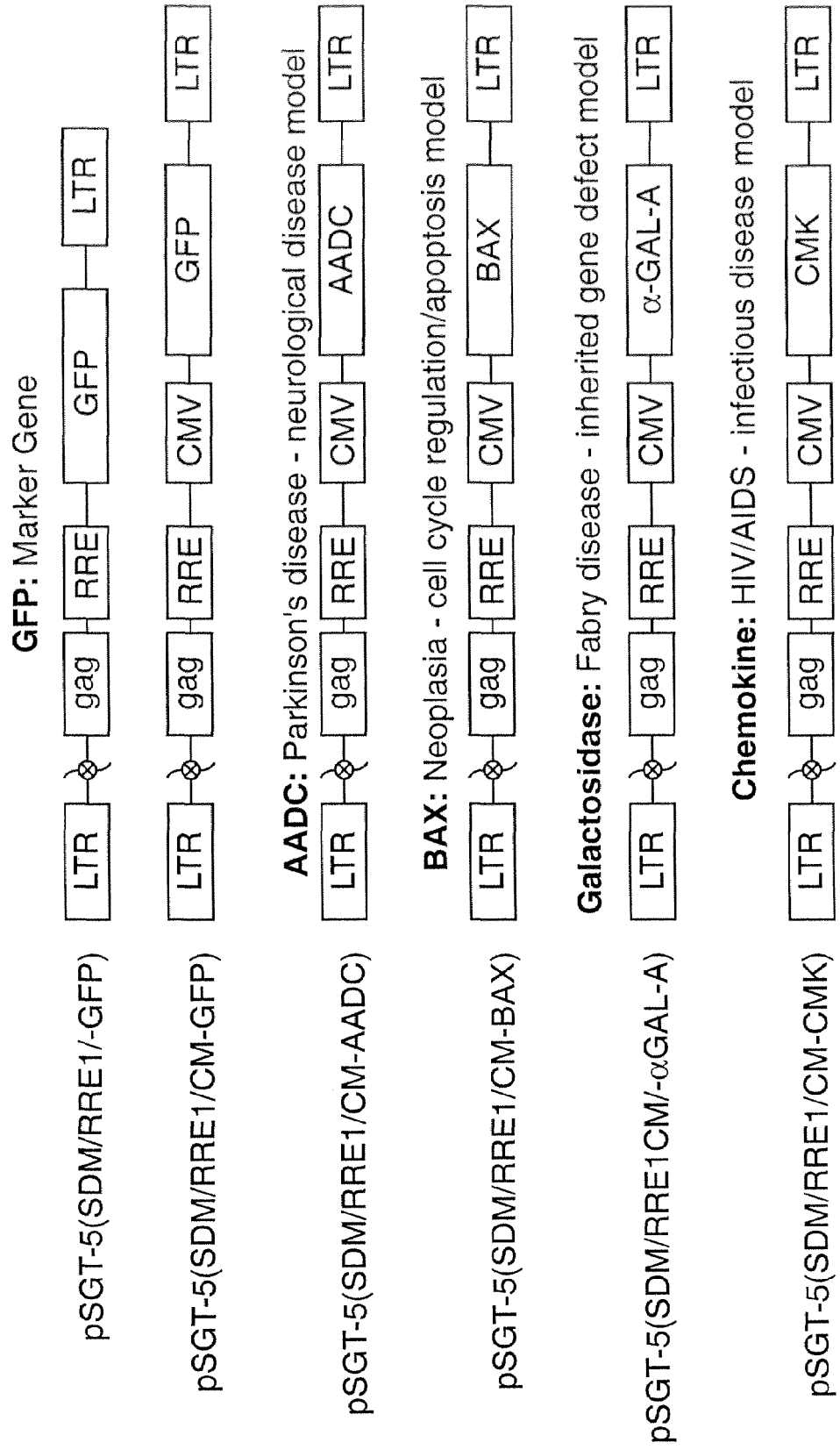
FIG. 14 shows the genetic structure of several HIV-2 transfer vectors, where the abbreviations represent the following: LTR, long terminal repeat; gag; RRE, Rev response element; CMV, Cytomegalovirus promoter; GFP, green fluorescent protein; AADC aromatic amino acid decarboxylase; BAX; α-GAL-A, α-galactosidase; CMK, chemokine. Clone pSGT(SDM) differs from clone pSGT-5(RRE) in having a modified splice donor site, denoted by a cross in the figure, which indicates a mutated or deleted SD that increases encapsidation of the vector RNA.

Several different transducing vectors were constructed containing the GFP transgene (see FIG. 14 and Table 8). The transducing vectors contained either no promotor (negative control; _GFP) or GFP protein expression was driven by the CMV promotor (CM-GFP). In addition, the length of the RRE was varied as described in EXAMPLE 7 (see Table 8; RRE1, 300 nt (SEQ ID NO 19); RRE2, 530 nt (SEQ ID NO 24); and RRE3, 792 nt (SEQ ID NO 26)). The splice donor was either functionally present (SD_) or functionally deleted (SDM). The backbone transfer vector, pSGT5(SDM/RRE1/CM), (SEQ ID NO 31) which contains no transgene, was used as a negative control.

The ability of the transduction vectors shown in Table 8 in the presence f the HIV-2 packaging vector pCM-ROD (SD36/EM) (SEQ ID NO 22) and the VSV-G envelope vector to drive GFP expression in 293T cells was measured. Serial dilutions from 1/10 to 1/100,000 of lentiviral-GFP vectors were prepared from a primary viral harvest (unconcentrated). The 293T cells were exposed to the GFP vectors for 14–16 hours vectors to transduce the cells as described in EXAMPLE 5.

The cells were subsequently analyzed for GFP expression 48 hours later by flow cytometry using the following method. Cells were gently washed once with PBS (phosphate buffered saline) and detached from the plate with 1 mM EDTA in PBS for 15 minutes at RT with slow shaking. The cells were resuspended by gentle pipetting then fixed in 2% para-formaldehyde for one hour on ice. After removing the para-formaldehyde, the cells were resuspended in PBS containing 2% FBS (fetal bovine serum) and GFP expression measured using cell sorting flow cytometry.

From this analysis, the viral titer was calculated in transduction units (MU) per ml (TU/ml). The viral titers shown in Table 8 are the lowest dilution of vector used to transduce the 293T cells in which GFP fluorescence is still observed. Titer values below those shown in Table 8 did not produce detectable GFP expression by the transduction vector.

As shown in Table 8, varying the length of the RRE in the leader sequence had little to no affect on viral titer, and thus on GFP transgene expression. However, the titer dropped by 10-fold in the presence of a functional SD [HIV-2(SD_/RRE1/CM-GFP)].

The results in Table 8 also demonstrate the effect of the presence or absence of a promotor to drive gene expression. The internal promoter CMV allowed expression of the GFP transgene (Table 8, all vectors containing "CM"). These results demonstrate that expression of a transgene can be achieved by using a foreign internal promotor, such as CMV, or by using a native promoter such as LTR (which was used above to drive neo expression; for example see Table 7 in EXAMPLE 7). However, a very low titer is observed if no promoter is present to drive expression of the transgene [HIV-2(SDM/RRE1/_GFP)]. The advantage of using internal promotors such as CMV is that CMV can function in many cells, while LTR requires viral TAT or a cellular homologue of TAT.

In conclusion, these results demonstrate that mutation of SD is important for transgene expression, irrespective of: the length of the RRE; the nature of the transgene (neo or GFP; expression of other transgenes are shown in EXAMPLES 11–14); whether the transgene is directed by the native LTR promoter or a foreign internal promoter; the presence or absence of IRES; and the presence or absence of introns.

TABLE 8

Lentivirus-GFP Vector Transduction of Human 293T Cells:

| Transducing vector | Packaging vector(core) | Envelope | Titer (TU/ml) |
|---|---|---|---|
| HIV-2* (SDM/RRE1/CM-GFP) | pCM-ROD (SD36/EM) | VSV-G | $3.2 \pm 1.3 \times 10^5$ |
| HIV-2 (SDM/RRE2/CM-GFP) | pCM-ROD (SD36/EM) | VSV-G | $4.3 \pm 1.7 \times 10^5$ |
| HIV-2 (SDM/RRE3ST/CM-GFP) | pCM-ROD (SD36/EM) | VSV-G | $3.4 \pm 2.0 \times 10^5$ |
| HIV-2 (SD_/RRE1/CM-GFP) | pCM-ROD (SD36/EM) | VSV-G | $4.2 \pm 2.0 \times 10^4$ |

TABLE 8-continued

Lentivirus-GFP Vector Transduction of Human 293T Cells:

| Transducing vector | Packaging vector(core) | Envelope | Titer (TU/ml) |
|---|---|---|---|
| HIV-2 (SDM/RRE/___GFP) | pCM-ROD (SD36/EM) | VSV-G | $\leq 10^4$ |
| pSGT-5 (SDM/RRE1/CM) | pCM-ROD (SD36/EM) | VSV-G | << |

*HIV-2 is pSGT-5

EXAMPLE 9

Concentration of Transfer Vectors

This example describes methods used to concentrate transfer lentivirus-GFP vectors. Similar methods can be used to concentrate any of the lentivirus vectors, for example a transfer lentiviral vector containing a therapeutic transgene. Concentration of the transfer vectors results in higher viral titers.

The viral vectors were concentrated as follows. One day before transfection, cells were plated at $0.5–1.5 \times 10^6$ cells per 75 cm T-flask in 12 ml of complete medium and incubated at 37° C., 5% $CO_2$. The following day, the medium was removed and eight ml of fresh medium was added and the cells incubated for 3–4 hours. Calcium-DNA precipitates were prepared as recommended by the manufacturer of the transfection kit (Life technologies, Gaithersburg, Md. or Promega, Madison, Wis.) with the following specifications: 8–12 μg vector DNA (usually 10 μg)+6–10 μg packaging DNA (usually 6 μg)+4–6 μg envelope DNA (usually 4 μg). The calcium-DNA mixtures were added to cultures dropwise with gentle mixing. The cells were subsequently incubated at 37° C., 5% $CO_2$ for 60–68 hours. Following the incubation, the culture medium (containing the viruses) was collected into a 15 ml sterile tube, which was centrifuged at 1200 rpm for five minutes. The clarified medium was filtered through a 0.45 μm syringe filter.

To further concentrate the virus, the following procedure was used. The filtered medium was centrifuged at ~50,000×g for 90 minutes at 4° C. using an appropriate ultracentrifuge rotor and speed. For example, the following can be used: Beckman Type 60Ti rotor at 30 –35,000 rpm or a Beckman Type 50Ti rotor at ~35,000 rpm. The resulting pellet was suspended in 1/200th of the starting volume (e.g., 0.8 ml for 120 ml starting volume) of cold TBS (50 mM Tris-HCl, pH 7.8; 130 mM NaCl; 10 mM KCl; 10 mM $MgCl_2$) containing 0.1 mM each of dNTP (dATP, dGTP, dTTP, dCTP), 3 mM spermine and 0.3 mM spermidine. This suspension was incubated at 37° C. for two hours. Following the incubation, the suspension was diluted with enough cold TBS containing 5 mM $MgCl_2$ to fill the centrifuge tube (for example to ~12 ml for Type 50Ti rotor) and centrifuged at 50,000×g for 90 minutes. The final pellet was suspended in 1/500th of the volume of the original culture medium in sterile, cold PBS (phosphate buffered saline), and aliquoted into 20 μl aliquots (e.g., 15×20 μl for 160 ml)

The 293T cells were transfected using serial dilutions of the concentrated vectors and the titer of the concentrated viruses calculated using the methods described in EXAMPLES 5 and 7. The transfer vector used was pSGT-5 (SDM/RRE1/CM-GFP). This vector was created by inserting the GFP sequence (SEQ ID NO 25) into the MCS (Xho1 cloning site at nt 2908 downstream of the CMV promoter) of pSGT-5(SDM/RRE1/CM) (SEQ ID NO 31). The packaging vectors used were pCM-ROD (SD36/EM) (SEQ ID NO 22) and pROD(SD36/EM) (SEQ ID NO 21) as shown in FIG. 4E. The envelope vector used was pCM-VSV-G (FIG. 4E, see EXAMPLE 6).

As a positive control, the ability to concentrate HIV-1 vector was also examined using the pHR-CM-GFP transducing vector (Salk Institute) and an HIV-1(CMV) packaging vector with the pCM-VSV-G envelope vector (FIG. 4E).

As shown in Table 9, the lentivirus vector can be concentrated using ultracentrifugation, to a level of at least $4 \times 10^7$ TU/ml. These results demonstrate that the HIV-2 lentiviral vectors can be concentrated several hundred-fold, similar to the results achieved with the HIV-1 lentiviral vectors. As shown in the examples below, the titers obtained by ultracentrifugation are sufficient to transduce a variety of cell types.

was calculated by flow cytometric cell sorting and dividing the number of fluorescent cells by the total number of cells in the sample.

As shown in Table 10, the HIV-2 GFP vector transduced cells of several different origins as well as observed by HIV-1 GFP. This transduction resulted in expression of the GFP transgene in all cell types tested. Table 11 shows the statistical analysis for experiments using primary fetal brain cells. The advantage of the HIV-2 vector system is that it is a safer vector than HIV-1, but is still able to transduce cells as well as HIV-1. In conclusion, these results demonstrate that the lentiviral system of the present invention has the ability to express the transgenes incorporated into the transfer vector in a wide variety of cells from different origins.

TABLE 9

Titer of Lentivirus-GFP Vectors on Human 293T Cells

| Transducing vector | Packaging vector (core) | Envelope | Unconcentrated | Centraprep-50 | Centriprep-50 + Ultracentrifuge | Ultracentrifuge |
|---|---|---|---|---|---|---|
| HIV-2 | pROD (SD36/EM) | VSV-G | $6 \times 10^4$ | — | — | $2 \times 10^6$ |
|  | pCM-ROD (SD36/EM) | VSV-G | $2 \times 10^5$ | $5 \times 10^6$ | $8 \times 10^7$ | $4 \times 10^7$ |
| HIV-1 | HIV-1 (CMV) | VSV-G | $1 \times 10^6$ | $3 \times 10^7$ | $6 \times 10^8$ | $2 \times 10^8$ |
| Untransduced | — | — |  | <0.1% |  |  |

EXAMPLE 10

Transduction of Several Human Cell Types

This example describes experiments in which the lentivirus-GFP vector HIV-2(SDM/RRE1/CM-GFP) (see EXAMPLE 9) was transduced into several different types of human cells, to demonstrate that transduction can occur in a wide variety of cell types. These methods can be used to determine the ability of other transduction vectors to transduce other cell types from different organisms. For example, the ability of a transfer lentiviral vector, such as a vector containing a transgene to be expressed in a cell in which that transgene is not endogenously expressed at normal levels, to transduce a cell of interest, can be determined using the methods described herein.

The following cell types were tested. Most cell lines were obtained from The American Type Culture Collection (ATCC, Manassas, Va.). The 293 (ATCC #CRL1573) and 293T cells were cultured in Dulbecco's Modified Eagle Medium (DMEM) with 10% Fetal Bovine Serum (FBS). HeLa cells (ATCC # CCL-2) were cultured under standard conditions. Fabry fibroblasts (OMN 94.3) and normal skin fibroblasts CD-27sk (ATCC #CRL-1475) were maintained in DMEM with 10% FBS. SVG (ATCC CRL-8621) and HFGC cells were grown in Minimal Essential Medium (MEM) with L-glutamine and 10% FBS. SVG-neural differentiated cells were cultured in Neurobasal Medium with L-glutamine, N2 supplement (neurotropic factors) and 1% FBS. SKN-MC (ATCC #HTB-10); SKN-SH; U281 and U373 (ATCC # HTB-17) cells were also tested.

Two different transfer vectors were tested: pGST-5 (SDM/RRE1/CM-GFP) (see EXAMPLE 9 and FIG. 14) and HIV-1(CMV) (Salk institute). Ultracentrifuged-concentrated transfer virus (EXAMPLE 9) was transduced into the cell lines listed in Table 10 at a multiplicity of infection (MOI) of 5.0, 1.0, 0.5, 0.1 or 0.01, using the methods described in EXAMPLES 5 and 7. The packaging vector for HIV-2 was pCM-ROD (SD36/EM) (SEQ ID NO 22) and for HIV-1 was HIV-1 (CMV). The envelope vector VSV-G was used for all experiments. The percent of cells transduced at each MOI

TABLE 10

Lentivirus-GFP Transduction of Human Cells

|  |  | HIV-2 GFP % Cells transduced at MOI of | | | HIV-1 GFP % Cells transduced at MOI of | | |
|---|---|---|---|---|---|---|---|
| Cells | Characteristic | 1.0 | 0.1 | 0.01 | 1.0 | 0.1 | 0.01 |
| 293 | Kidney epitheloid | 33 | 9 | — | 47 | 13 | — |
| HeLa | Ovarian epitheloid | 52 | 8 | — | 62 | 15 | — |
| CD27sk | Skin fibroblast | 62 | 15 | — | 81 | 26 | — |
| OMN 94.3 | Fabry fibroblast | 58 | 14 | — | 71 | 17 | — |
| SVG | Fetal brain/SV40 | 56 | 17 | 1 | 82 | 28 | 5 |
| SVG-differentiated | Fetal brain/SV40 | 50 | 11 | 2 | 70 | 29 | 5 |
| HFGC | Primary fetal brain | 55 | 20 | 2 | 69 | 27 | 4 |
|  |  | 5.0 | 1.0 | 0.5 | 0.1 | 5.0 | 1.0 | 0.1 |
| SKN-MC | Neuroepithelioma | 46 | — | 16 | — | 58 | — | — |
| SKN-SH | Neuroblastoma | 50 | 51 | — | 3 | 58 | 58 | 15 |
| U281 | Glioma | 68 | 63 | — | 17 | 92 | 91 | 40 |
| U373 | Glioma | 68 | 56 | — | 9 | 92 | 80 | 40 |

TABLE 11

Lentivirus-GFP Transduction of Primary Human Fetal Brain Cells in vitro

| Transducing vector | Packaging vector (core) | Envelope | % Cells Transduced | |
|---|---|---|---|---|
|  |  |  | MOI = 1 | MOI = 0.1 |
| HIV-2 | HIV-2 | VSV-G | 54 ± 8 | 9 ± 5 |
| — | HIV-2 | HIV-2 | 0.1 | 0.1 |

TABLE 11-continued

Lentivirus-GFP Transduction of Primary Human Fetal Brain Cells in vitro

| Transducing vector | Packaging vector (core) | Envelope | % Cells Transduced | |
|---|---|---|---|---|
| | | | MOI = 1 | MOI = 0.1 |
| HIV-1 | HIV-1 | VSV-G | 77 ± 9 | 26 ± 11 |
| Untransduced | | | <0.1 | <0.1 |

EXAMPLE 11

Fabry Disease Model

This example describes the generation and testing of therapeutic vectors that can be used to deliver genes to cells, such as cells of individuals suffering from a deficiency in α-galactosidase (α-GAL-A) expression. Cell delivery can be either in vitro or in vivo. For example, the lentiviral vectors described herein can be used for gene therapy to treat individuals suffering from Fabry disease, an inborn error of metabolism. Individuals suffering from Fabry disease are α-GAL-A deficient, and as a result, deposit large amounts of glycolipid in their cells. By providing the α-GAL-A gene in trans, for example by expressing α-GAL-A in the cells of a Fabry individual using the lentiviral transducing, packaging and envelope vectors of the present invention, the cells of a Fabry individual would be expected to clear the excess cellular glycolipid.

An HIV-2 transducing vector containing the α-gal gene, HIV-2(CM-α-GAL-A), was constructed as shown in FIG. 14. Briefly, the murine α-GAL-A gene sequence (SEQ ID NO 27) was cloned into the MCS of the transfer vector pGST-5 (SDM/RRE1/CM) (SEQ ID NO 31). Alternatively, the human (or any other species)α-GAL-A gene sequence can be used (Genbank Accession No X14448).

Fabry fibroblasts (OMN 94.3 and 98.5) were transduced in vitro with concentrated lentiviral-α-GAL-A vectors shown in Table 12, using the methods described in EXAMPLES 5 and 7. As a control, both an HIV-1 (HIV-1 (CMV)) and an HIV-2 [PCM-ROD (SD36/EM) (SEQ ID NO 22)] packaging vector along with the VSV-G envelope vector were tested. Following the transduction (48 hours later), cells were detached from the plates using trypsin and washed with PBS. The cells were resuspended in homogenization buffer (28 mM citric acid, 44 mM disodium phosphate, 3 mg/ml sodium taurocholate, pH 4.4) and sonicated 5×10 seconds on ice. To assay for the level of α-GAL-A protein expressed, 150 µl of the substrate 5 mM 4-methylumbelliferyl-α-D-galactopyranoside (4MU) was added to the cell extracts with and without the α-galactosidase B inhibitor, N-acetyl-galactosamine. The mixture was incubated at 37° C. for 30 minutes. The enzyme reaction was stopped by adding stop buffer (0.1 M glycine; 0.1 M NaOH). The fluorescent values at 336 nm were read against a water blank. A standard curve for 4MU was plotted and the specific enzyme activity was calculated as nmole/hr/mg protein. Normal individuals have an α-GAL-A activity of 130–370 nmoles/hr/mg while Fabry individuals have reduced α-GAL-A activity of 2–20 nmoles/hr/mg.

As shown in Table 12, untransduced Fabry cells have an α-GAL-A activity of between 50–118. However, upon expression of the α-gal gene using the lentivirus system of the present invention, levels of α-GAL-A in the Fabry fibroblasts increased dramatically. Therefore, high-levels of expression of α-GAL-A can be achieved using the lentiviral vectors of the present invention. Similar results were obtained with the HIV-1 and HIV-2 packaging vectors.

TABLE 12

Lentivirus-α-GAL-A Transduction of Human Fabry Fibroblasts in vitro

| Transducing vector | Packaging Vector (core) | Envelope | α-GAL-A activity (nmoles/hr/mg) | |
|---|---|---|---|---|
| | | | In 98.5 cells | In 94.3 cells |
| HIV-2 (CM-AGA) | HIV-2 | VSV-G | 2,730 ± 420 | 1,860 ± 1,700 |
| | HIV-1 | VSV-G | 2,680 ± 1,720 | 1,350 ± 750 |
| HIV-2(CM-AGA/Rpuro) | HIV-2 | VSV-G | 2,520 ± 1,990 | |
| | HIV-1 | VSV-G | 4,600 ± 1,550 | |
| Untransduced | — | — | 118 ± 114 | 50 ± 50 |

To determine if the increased expression of the α-gal gene in Fabry fibroblasts would result in the clearance of excess cellular glycolipids, the following assay was conducted. After determining that the cells were expressing near-normal levels or higher of the α-gal gene, (see Table 12), the cells were analyzed using a CTH clearance assay.

Fabry fibroblasts were transduced with lentiviral-α-GAL-A vectors for 14–16 hours and 48 hours were allowed for α-gal gene expression. The medium was removed and the cells were washed twice with PBS. The cells were incubated overnight with DMEM containing 3 nM nM/ml of lysamine-rhodamine conjugated cerebotrihexosamide (CTH) in the absence of serum. The next day, the CTH was removed and the cells washed twice with PBS. Subsequently, the cells were incubated in DMEM containing 10% FBS. The cells were observed periodically after 6 hours, 24 hours and 48 hours using a florescence microscope at 32×, 20× and under phase contrast. A decrease in cellular florescence indicated that glycolipid was being cleared from the Fabry cells.

The results of these experiments demonstrate that Fabry fibroblasts expressing the α-GAL-A transgene clear glycolipids better than Fabry fibroblasts that were not transduced with the α-GAL-A gene. Therefore, lentiviral vectors of the present invention which allow expression of a functional α-GAL-A gene can be used to deliver the α-GAL-A gene into the cells of Fabry patients suffering from decreased α-GAL-A expression and from accumulation of glycolipid in their cells.

One skilled in the art will recognize that the exact full-length α-GAL-A nucleic acid sequence shown in SEQ ID NO 27 will not be the only sequence that will allow expression of functional α-GAL-A. For example, the amino acids can be conservatively substituted (see Definitions section) or the nucleic acid sequence can altered to encode the identical amino acid by using a different triplet encoding that amino acid. In addition, alternative species of α-GAL-A can be used.

EXAMPLE 12

Parkinson's Disease Model

This example describes the generation and testing of therapeutic vectors that can be used to deliver genes to cells, such as cells of individuals suffering from a deficiency in aromatic amino acid decarboxylase (AADC) expression. Cell delivery can be either in vitro or in vivo. For example, the lentiviral vectors described herein can be used for gene therapy to treat individuals suffering from Parkinson's disease. Individuals suffering from Parkinson's disease suffer from the loss of substantia nigra neurons, which results in depletion of the neurotransmitter dopamine in the hypothalamus. As a result, Parkinson's patients suffer from a biochemical pathway defect in their neurons, specifically the inability to convert L-dopa into L-dopamine.

One approach to treating Parkinson's disease is to convert L-dopa into L-dopamine, by expressing the aromatic amino acid decarboxylase (AADC) gene in the region of the brain where dopamine is depleted. For example, the lentiviral transducing and packaging vectors of the present invention can be used to express AADC in neural cells for gene therapy to treat individuals suffering from Parkinson's disease. By providing the AADC gene in trans, for example by expressing AADC in the cells of a Parkinson's patient, the neurons of a Parkinson's individual would be expected to convert L-dopa in their cells to L-dopamine.

Two HIV transfer vectors containing the AADC gene were constructed: HIV-1 AADC and HIV-2 AADC (see FIG. 14). The sequence of HIV-2 AADC was obtained by inserting the human AADC gene sequence (SEQ ID NO 28) into the cloning site of the transfer vector pGST-5 (SDM/RRE1/CM) (SEQ ID NO 31).

Each of the HIV AADC transfer vectors were individually used to transform human fetal brain cells in vitro, using the methods described above. As a control, both an HIV-1 (HIV-1 (CMV)) and an HIV-2 [pCM-ROD (SD36/EM) (SEQ ID NO 22)] packaging vector were used with the VSV-G envelope vector (FIG. 4E). Subsequently, the conversion of L-dopa to L-dopamine was measured as described below. Similar methods can be used to test the ability of the HIV-2 AADC vector to convert L- dopa to L-dopamine.

Cells (SVG, HFGC, and SVG-differentiated) were transduced with HIV-1-AADC. Forty-eight hours post infection, the cells were washed once with HEPES buffered saline which was left on the cells for one minute. After removing the buffered saline, 4 µM L-dopa in HEPES buffered saline was added and the samples incubated for 30 or 60 minutes with L-dopa buffer. At the end of the specified time, a 150 µl aliquot of the buffer was added to a tube containing 15 µl of lysis solution (0.1 N perchloric acid, 1% ethanol, 0.02% EDTA) and the sample stored on dry ice. To the remainder of the buffer, 1 ml of the lysis solution was added to the cells and the sample placed on dry ice. The dopamine and other metabolite levels were measured by HPLC.

As shown in Table 13, uninfected SVG and HFGC cells are unable to convert L-dopa to L-dopamine even after 60 minutes. However, expression of AADC by the HIV-1 AADC transfer vector results in the ability of these same cells to convert L-dopa to L-dopamine. The described herein can be used to test the ability of HIV-2 AADC to express AADC and result in the ability of AADC deficient cells to convert L-dopa to L-dopamine.

One skilled in the art will recognize that the exact full-length AADC nucleic acid sequence shown in (SEQ ID NO 28) will not be the only sequence that will allow expression of functional AADC. For example, the amino acids can be conservatively substituted or the nucleic acid sequence can altered to encode the identical amino acid by using a different triplet encoding that amino acid.

TABLE 13

HIV-1 AADC Transduction of Human Fetal Brain Cells

| Cells | % Conversion from L-dopa to L-dopamine | |
|---|---|---|
| | 30 minutes | 60 minutes |
| (a) Secreted | | |
| SVG cells | 19.0 | (6.5) |
| SVG cells - differentiated | 39.2 | 46.0 |
| HFGC- primary, short term | 24.5 | 51.0 |
| Uninfected SVG/HFGC | 0 | 0 |
| (b) Intracellular | | |
| SVG cells | 72.4 | 59.2 |
| SVG cells - differentiated | 91.4 | 76.7 |
| HFGC - primary, short term | 86.5 | 95.0 |
| Uninfected SVG/HFGC | 0 | 0 |

EXAMPLE 13

Infectious Disease Model

This example describes the generation and testing of therapeutic lentiviral vectors that can be used to deliver genes to cells, such as cells of individuals suffering from an infectious disease. Cell delivery can be either in vitro or in vivo. For example, the lentiviral vectors described herein can be used for gene therapy to treat individuals suffering infectious diseases, such as AIDS resulting from HIV infection. Treatment of infectious diseases is be aided by achieving high local secretion of antiviral chemokines to block infection and inhibit the virus. In addition, virus inhibition can be achieved by intracellular expression of a mutant chemokine to block infection from within and achieve intracellular immunization.

Several HIV transfer vectors containing the RANTES gene were constructed (see FIG. 14 and Table 14). HIV-2 (CM-Rant-Rpuro), HIV-2(CM-RantKD-Rpuro), and HIV-2 (CM-Rant8A-Rpuro) (see Table 14) were constructed. Rant is the RANTES shown in SEQ ID NO 29. RantKD contains a SKDEL tag on the carboxy terminus and Rant 8A is a substitution mutant. These transfer vectors were generated by inserting the RANTES sequence (or variation thereof) into the cloning site of pSGT-5(SDM/RRE1/CM) (SEQ ID NO 31).

Each of the HIV-2 RANTES transfer vectors were individually used to transform human 293T cells in vitro, using the methods described above. The packaging vectors used were the HIV-1 and HIV-2 packaging vectors used in EXAMPLES 9–12, with the VSV-G envelope vector (FIG. 4E).

Supernatants and cell lysates from cells transduced with lentiviral-RANTES vectors were collected and assayed for RANTES protein concentration (the amount secreted into the media and the intracellular amount) was measured using a quantitative sandwich ELISA assay. Microwells of an ELISA plate were coated with a murine monoclonal antibody to RANTES (5Prime-3Prime, Inc., Boulder, Colo.). To each well, either standards, blanks, diluted supernatants or cell lysates were added and incubated for two hours. The cells were washed and horseradish peroxidase (HRP) conjugated polygonal antibody to RANTES was added and incubated for one hour. The wells were subsequently washed and to the wells, a color substrate (tetramethylbenzidine in hydrogen peroxide) was added and incubated for 20 minutes. Sulfuric acid (2N) was added to stop the reaction. The reaction in each well was read at 450 nm against the blank.

As shown in Table 14, RANTES protein is expressed in the cells transformed with the RANTES sequence (SEQ ID NO 29). However, no detectable RANTES protein was detected in the cells transformed with the substitution mutant (Rant 8A). Higher levels of expression were observed in the cells transfected with the RantKD sequence.

In addition to RANTES, other chemokines can be used in the present invention. Similar methods can be used to test the ability of any lentiviral vector to containing a chemokine gene to express that gene product.

TABLE 14

Lentivirus-RANTES Transduction of Human 293T Cells

| Transducing Vector | Packaging vector (core) | Envelope | RANTES Protein | |
|---|---|---|---|---|
| | | | Secreted (ng/ml) | Intracellular (mg/mg protein) |
| HIV-2(CM-Rant-Rpuro) | HIV-2 | VSV-G | 0.96 ± 0.16 | 0.25 ± 0.05 |
| HIV-2(CM-Rant-Rpuro) | HIV-1 | VSV-G | 3.8 ± 0.3 | 5.17 ± 4.0 |
| HIV-2(CM-RantKD-Rpuro) | HIV-2 | VSV-G | 2.4 ± 0.4 | 1.15 ± 0.45 |
| HIV-2(CM-RantKD-Rpuro) | HIV-1 | VSV-G | 2.5 ± 0.2 | 1.9 ± 0.4 |
| HIV-2(CM-Rant8A-Rpuro) | HIV-2 | VSV-G | << | << |
| HIV-2(CM-Rant8A-Rpuro) | HIV-1 | VSV-G | << | << |
| Uninfected 293 T | | VSV-G | 0.05 | 0.2 |

EXAMPLE 14

Apoptosis Model

This example describes the generation of therapeutic lentiviral vectors that can be used to deliver genes to cells, such as cells of individuals suffering from a defect in cell cycle regulation. Cell delivery can be either in vitro or in vivo. For example, the lentiviral vectors described herein can be used for gene therapy to treat individuals suffering from cancer, in which there is either an up or downregulation of apoptosis.

Genes which are known to regulate apoptosis can be inserted into the cloning site of the HIV-2 lentiviral backbone vector of the present invention (SEQ ID NO 31). Any of the genes known to regulate the cell cycle, such as BAX, can be cloned into the cloning site of SEQ ID NO 31. One such example is shown in FIG. 14.

BAX expression, or the expression of any other gene involved in regulating the cell cycle, can be monitored using standard methods, for example ELISA assays or flow cytometric methods such as those described in the above examples.

EXAMPLE 15

Testing Lentivirus Vectors in vivo

The lentiviral vectors described in the above examples can be tested for their ability to express a transgene in mouse models which have been generated for various diseases. Mice which are functionally deleted for a transgene, are infected with a transfer vector containing the transgene along with a packaging vector. Mice are then screened for their ability to express the transgene, and the ability of the transgene to correct the phenotypic affect of the transgene deletion.

EXAMPLE 16

Gene Therapy Using Lentivirus Vectors

A new gene therapy approach for patients using the lentiviral transfer and packaging vectors taught by the present invention, is now made possible by the present invention. Essentially, cells can be removed from a subject having deletions or mutations of a gene, and then transfected with the packaging and transfer vectors (which contains the therapeutic transgene). These transfected cells will thereby produce functional transgene protein and can be reintroduced into the patient. Methods described in U.S. Pat. No. 5,162,215 (Bosselman et al.) (herein incorporated by reference) demonstrate how to detect the presence and expression of a gene of interest in target cells. Methods described in U.S. Pat. No. 5,741,486 (Pathak et al.) (herein incorporated by reference) teach the use of retroviral vectors in gene therapy. Methods described in PCT WO 98/39463 (here in incorporated by reference) demonstrates other approach to construction and use of lentivrial vectors ass a gene transfer vector. Such methods can be applied to the lentiviral vectors of the present invention, for example in gene therapy.

The scientific and medical procedures required for human cell transfection are now routine procedures. The provision herein of lentivrial transfer and packaging vectors now allows the development of human and non-human gene therapy based upon these procedures.

In some embodiments, the present invention relates to a method of treating patients which underexpress a transgene, or in which greater expression of the transgene is desired. These methods can be accomplished by introducing a gene coding for the therapeutic transgene into a transfer vector, which is subsequently introduce into the patient along with a packaging vector.

In some of the foregoing examples, it may only be necessary to introduce the genetic or protein elements into certain cells or tissues. For example, in the case of benign nevi and psoriasis, introducing them into only the skin may be sufficient. However, in some instances (i.e. tumors and polycythemia inflammatory fibrosis), it may be more therapeutically effective and simple to treat all of the patients cells, or more broadly disseminate the vector, for example by intravascular administration.

The transfer and packaging vectors can be administered to the patient by any method which allows the vectors to reach the appropriate cells. These methods include injection, infusion, deposition, implantation, or topical administration. Injections can be intradermal or subcutaneous.

EXAMPLE 17

Specificity of HIV Packaging

Figure 13:
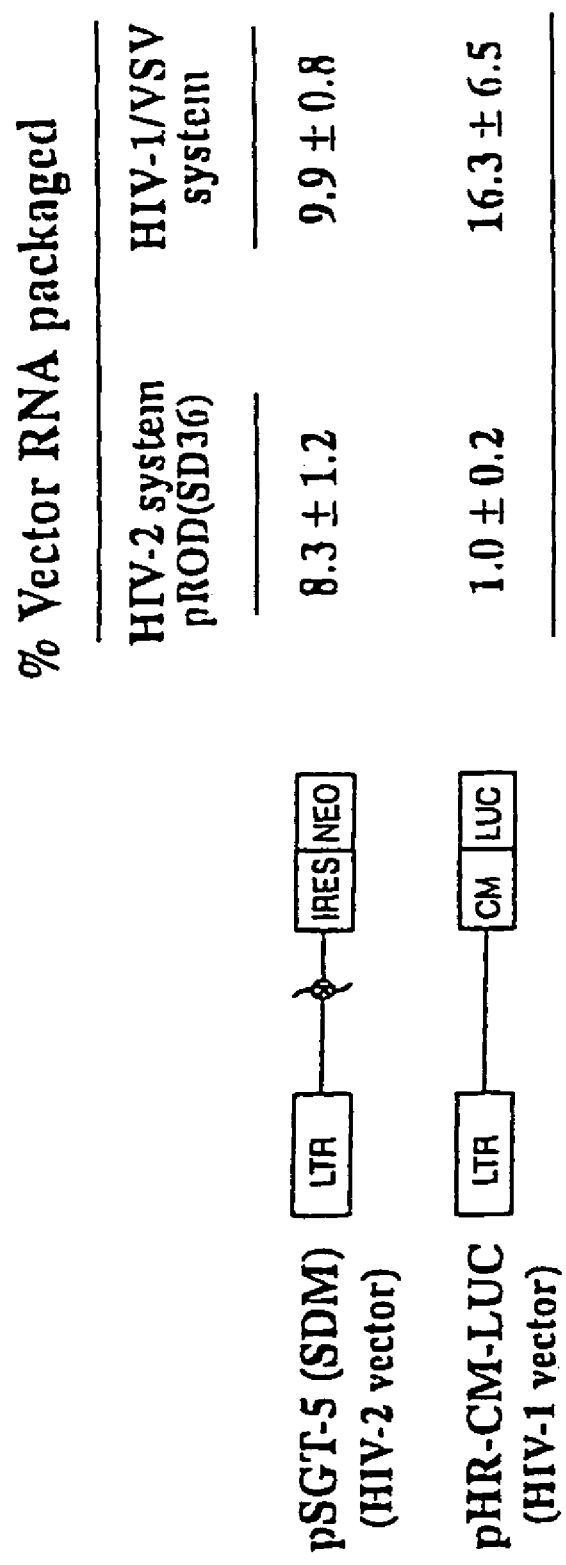
FIG. 13 shows the results of cross packaging experiments between HIV-1 and HIV-2 vectors.

The ability of HIV-1 and HIV-2 to "cross-package," that is package the other species RNA, was investigated. Human 293T cells were transfected with a transfer vector and a packaging vector as shown in FIG. 13. The ability of the vectors to package its own RNA was compared to its ability to package the other HIV species as described in EXAMPLE 5.

As shown in FIG. 13, there is a 4–5 fold increase in the specificity of HIV-2 packaging compared to HIV-1. HIV-2 packages 8% of vector RNA in the presence of an HIV-2 transfer vector [pSGT-5 (SDM); SEQ ID NO 14], but only 1% in the presence of an HIV-1 transfer vector (pHR-CM-LUC). This is an 8-fold difference. In contrast, HIV-1 packages 16% of the vector RNA in the presence of an HIV-1 transfer vector, and 10% in the presence of an HIV-2 transfer vector. This is only a 1.5–2 fold difference.

The titer of vector obtained was also investigated. Using the methods described above, 293T cells were transduced with an HIV-1 [HIV-1(CMV)], or an HIV-2 [pSGT-5(SDM/RRE1/CM-GFP)] transfer vector. As shown in Table 15, the HIV-1 packaging vector can package the transgene present in both the HIV-1 and HIV-2 vector RNA, whereas the HIV-2 packaging is more specific in preferentially encapsidating its own vector RNA than HIV-1 vector RNA.

TABLE 15

Lentivirus-GFP Vector Transduction of Human 293T Cells

| Transducing vector | Packaging vector (core) | Envelope | Titer (TU/ml) |
|---|---|---|---|
| HIV-2 | HIV-2 | VSV-G | $1.1 \pm 0.8 \times 10^5$ |
| HIV-2 | HIV-1 | VSV-G | $2.0 \pm 0.8 \times 10^5$ |
| HIV-2 | HIV-2/Env- | HIV-2 | $<4.0 \times 10^4$ |
| HIV-1 | HIV-2 | VSV-G | $2.2 \pm 0.6 \times 10^4$ |
| HIV-1 | HIV-1 | VSV-G | $1.6 \pm 0.6 \times 10^6$ |
| HIV-1 | HIV-2/Env- | HIV-2 | $<2.0 \times 10^4$ |
| Untransduced | — | — | — |

In summary, the HIV-2 packaging is more stringent while HIV-1 packaging more promiscuous. These results indicate that HIV-2 packaging yields better quality vector and as a result also a higher titer than HIV-1 packaging. This observation can be further exploited by designing a hybrid packaging system using split genome strategy (see EXAMPLE 6) where the envelope-defective HIV-2 packaging vector will be complemented with an HIV-1 envelope expression plasmid. The RNA encoded by HIV-1 plasmid will not be co-packaged by the HIV-2 packaging vector, thus achieving another built-in safety feature.

EXAMPLE 18

SIV Packaging and Transfer Vectors

The generation of packaging (EXAMPLES 1–4, 6) and transfer (EXAMPLES 5–14) lentiviral vectors was described above. Given the similarities in the genomic organization of HIV and SIV, one skilled in the art could apply what was learned from HIV-2 to SIV. For example, an SIV packaging vector can be generated by making upstream and downstream SD deletions as described above for HIV-2. Specifically, an SIV pROD(SD36) homologue, pSIV(SD36) (FIG. 5B; SEQ ID NO 11) can be generated using standard molecular biology methods. This SIV packaging vector could also be divided into two parts, as described in EXAMPLE 6. The envelope region of pSIV(SD36) can be mutated to render it non-functional, while another vector containing the functional envelope in trans would be provided to compensate for the envelope defect.

An SIV transfer vector can be generated by generating a functional mutation in the SD site. The SIV pSGT-5 (SDM) homologue, pSIV(SDM) (FIG. 5C; SEQ ID NO 12), can be generated using standard molecular biology methods.

The ability of these vectors to function as transfer and packaging vectors could be tested by the methods described in EXAMPLES 1–5, and for the ability to express specific transgenea as described in EXAMPLES 7–14.

EXAMPLE 19

Use of the Nucleic Acids of the Invention as Molecular Probes

In addition to their utility in making HIV packaging cell lines, the non-infective packaging vectors of the invention can be used to detect wild-type HIV in biological samples using Southern or northern blot assays. In brief, the packaging vector is labeled, typically using a radio or bioluminescent label, and used to probe a northern or Southern blot of a sample suspected of containing HIV virus. The use of the packaging vector as a probe is safer than the use of an infective virus as a probe. The packaging vector is also more likely to detect a wild type virus than a smaller probe because, unlike a small probe, the packaging vector probe has virtually the entire genome in common with a wild-type virus, making it improbable that the wild type virus could escape detection by mutation of the probe binding site.

Furthermore, the packaging vectors can be used as positive controls in essentially all known detection methods for the detection of HIV. In this embodiment, a packaging vector nucleic acid or encoded polypeptide is used as a positive control to establish that an HIV detection assay is functioning properly. For instance, oligonucleotides are used as primers in PCR reactions to detect HIV nucleic acids in biological samples such as human blood in clinical settings. The packaging vector, which comprises nucleic acid subsequences corresponding to the region to be amplified is used as an amplification templates in a separate reaction from a test sample such as human blood to determine that the PCR reagents and hybridization conditions are appropriate. Similarly, the polypeptides encoded by the packaging vector can be used to check ELISA reagents in assays for the detection of HIV expression products in biological samples.

EXAMPLE 20

Cellular Transformation and Gene Therapy

The present invention provides packageable nucleic acids for the transformation of cells in vitro and in vivo. These packageable nucleic acids are packaged in HIV-2 particles in the packaging cell lines described herein. The nucleic acids are transfected into cells through the interaction of the HIV particle surrounding the nucleic acid and the HIV cellular receptor.

Cells which can be transfected by HIV particles include, but are not limited to: CD4+ cells, including T-cells such as Molt4/8 cells, SupT1 cells, H9 cells, C8166 cells and myelomonocytic (U937) cells as well as primary human lymphocytes, and primary human monocyte-macrophage cultures, peripheral blood dendritic cells, follicular dendritic cells, epidermal Langerhans cells, megakaryocytes, microglia, astrocytes, oligodendroglia, CD8+ cells, retinal cells, renal epithelial cells, cervical cells, rectal mucosa, trophoblastic cells, and cardiac myocytes. Thus, the packageable nucleic acids of the invention are generally useful as cellular transformation vectors.

In one particular class of embodiments, the packageable nucleic acids of the invention are used in cell transformation procedures for gene therapy. Gene therapy provides methods for combating chronic infectious diseases such as HIV, as well as non-infectious diseases such as cancer and birth defects such as enzyme deficiencies. Yu et al. *Gene Therapy* 1:13–26, 1994, and the references therein provides a general guide to gene therapy strategies for HIV infection. See also, Sodoski et al. PCT/US91/04335. One general limitation of common gene therapy vectors such as murine retroviruses is that they only infect actively dividing cells, and they are generally non-specific. The present invention provides several features that allow one of skill to generate powerful retroviral gene therapy vectors which specifically target cells in vivo (for example CD4+ cells), and which transform many cell types in vitro. CD4+ cells, including non-dividing cells, are transduced by nucleic acids packaged in HIV particles. HIV particles also infect other cell-types in vitro which exhibit little or no CD4 expression, such as those listed in the preceding paragraph. Thus, these cells can be targeted by the HIV particle-packaged nucleic acids of the invention in ex vivo gene therapy procedures, or in drug discovery assays which require transformation of these cell types.

Pseudotyping the Packageable Vector

Hematopoietic stem cells are targets for cell transformation in general, and for gene therapy in particular. Packageable vectors are made competent to transform CD34+ cells by pseudotyping the vector. This is done by transducing the packaging cell line used to package the vector with a nucleic acid which encodes the vesicular stomatitis virus (VSV) envelope protein, which is expressed on the surface of the vector. VSV infects both dividing and non-dividing CD34 + cells, and pseudotype vectors expressing VSV envelope proteins are competent to transduce these cells.

Similarly, viral or cellular proteins in general can be co-expressed to increase the host range of an HIV-based vector. Typically, a nucleic acid encoding a selected protein is coexpressed in an HIV packaging cell of the invention. Protein encoded by the nucleic acid is incorporated into the particle which packages an HIV-packageable nucleic acid, which buds off from the packaging cell membrane. If the protein is recognized by a cellular receptor on a target cell, the particle is transduced into the cell by receptor mediated endocytosis. Examples of such proteins include viral (such as retroviral) envelope or coat proteins, cell receptor ligands, antibodies or antibody fragments which bind cell receptors on target cells, and the like.

Promoters

One embodiment of the invention can use an HIV LTR sequence as a promoter for the HIV packageable vector. These LTR sequences are trans-activated upon infection of a cell containing the LTR promoter by the infecting virus. LTR promoters, in addition to binding tat and rev are responsive to cellular cytokines (such as IL-2 and SP-1) which act to permit transcription of the HIV genome upon infection. Thus, in one example, a therapeutic nucleic acid is placed under the control of an LTR promoter, rendering the cells ordinarily most vulnerable to HIV infection resistant to infection. See, e.g., Poznansky et al., *J. Virol.* 65: 532–536, 1991, for a description of the region flanking the 5' LTR's ability to package vector nucleic acids.

Ex Vivo Transformation of Cells

Ex vivo methods for inhibiting viral replication in a cell in an organism involve transducing the cell ex vivo with a therapeutic nucleic acid of this invention, and introducing the cell into the organism. The cells are typically CD4 + cells, such as CD4 + T cells or macrophages isolated or cultured from a patient, or are stem cells. Alternatively, the cells can be those stored in a cell bank (e.g., a blood bank). In one embodiment, the packageable nucleic acid encodes an anti-viral therapeutic agent (e.g., suicide gene, trans-dominant gene, anti-HIV ribozyme, anti-sense gene, or decoy gene) which inhibits the growth or replication of an HIV virus, under the control of an activated or constitutive promoter. The cell transformation vector inhibits viral replication in any of those cells already infected with HIV virus, in addition to conferring a protective effect to cells which are not infected by HIV.

In some embodiments, the vector is replicated and packaged into HIV capsids using the HIV replication machinery, thereby causing the anti-HIV therapeutic gene to propagate in conjunction with the replication of an HIV virus. Thus, an organism infected with HIV can be treated for the infection by transducing a population of its cells with a vector of the invention and introducing the transduced cells back into the organism as described herein. Thus, the present invention provides a method of protecting cells in vitro, ex vivo or in vivo, even when the cells are already infected with the virus against which protection is sought.

Stem cells (which are typically not CD4+) can be used in ex-vivo procedures for cell transformation and gene therapy. The advantage of using stem cells is that they can be differentiated into other cell types in vitro, or can be introduced into a mammal (such as the donor of the cells) where they will engraft in the bone marrow. Methods for differentiating CD34+ cells in vitro into clinically important immune cell types using cytokines such a GM-CSF, IFN-γ and TNF-α are known (see, Inaba et al., *J. Exp. Med.* 176:1693–1702, 1992). Methods of pseudotyping HIV-based vectors so that they can transform stem cells are described above.

Stem cells are isolated for transduction and differentiation using known methods. For example, in mice, bone marrow cells are isolated by sacrificing the mouse and cutting the leg bones with a pair of scissors. Stem cells are isolated from bone marrow cells by panning the bone marrow cells with antibodies which bind unwanted cells, such as CD4+ and CD8+ (T cells), CD45+ (panB cells), GR-1 (granulocytes), and Ia$^d$ (differentiated antigen presenting cells). For an example of this protocol see, Inaba et al., *J. Exp. Med.* 176:1693–1702, 1992.

In humans, bone marrow aspirations from iliac crests are performed e.g., under general anesthesia in the operating room. The bone marrow aspirations are collected from the posterior iliac bones and crests. If the total number of cells collected is <2×10$^8$/kg, a second aspiration using the sternum and anterior iliac crests in addition to posterior crests is performed. During the operation, two units of irradiated packed red cells are administered to replace the volume of marrow taken by the aspiration. Human hematopoietic progenitor and stem cells are characterized by the presence of a CD34 surface membrane antigen. This antigen is used for purification, e.g., on affinity columns which bind CD34.

After the bone marrow is harvested, the mononuclear cells are separated from the other components by means of ficol gradient centrifugation. This is performed by a semi-automated method using a cell separator (e.g., a Baxter Fenwal CS3000+ or Terumo machine). The light density cells, composed mostly of mononuclear cells are collected and the cells are incubated in plastic flasks at 37° C. for 1.5 hours. The adherent cells (monocytes, macrophages and B-Cells) are discarded. The non-adherent cells are then collected and incubated with a monoclonal anti-CD34 antibody ( e.g., the murine antibody 9CS) at 4° C. for 30 minutes with gentle rotation. The final concentration for the anti-CD34 antibody is 10 µg/ml. After two washes, paramagnetic microspheres (Dyne Beads, supplied by Baxter Immunotherapy Group, Santa Ana, Calif.) coated with sheep antimouse IgG (Fc) antibody are added to the cell suspension at a ratio of 2 cells/bead. After a further incubation period of 30 minutes at 4° C., the rosetted cells with magnetic beads are collected with a magnet. Chymopapain (supplied by Baxter Immunotherapy Group, Santa Ana, Calif.) at a final 5 concentration of 200 U/ml is added to release the beads from the CD34+ cells. Alternatively, an affinity column isolation procedure can be used which binds to CD34, or to antibodies bound to CD34 (see, the examples below). See, Ho et al., *Stem Cells* 13 (suppl. 3): 100–105, 1995. See also, Brenner, *J. Hemalotherapy* 2: 7–17, 1993.

In another embodiment, hematopoetic stem cells are isolated from fetal cord blood. Yu et al., *PNAS USA* 92: 699–703, 1995, describes another method of transducing CD34+ cells from human fetal cord blood using retroviral vectors.

Ex Vivo Transformation of T Cells

Rather than using stem cells, T cells are also used in other examples of ex vivo procedures. Several techniques are known for isolating T cells. In one method, Ficoll-Hypaque density gradient centrifugation is used to separate PBMC from red blood cells and neutrophils according to established procedures. Cells are washed with modified AIM-V [which consists of AIM-V (GIBCO) with 2 mM glutamine, 10 µg/ml gentamicin sulfate, 50 µg/ml streptomycin) supplemented with 1% fetal bovine serum (FBS)]. Enrichment for T cells is performed by negative or positive selection with appropriate monoclonal antibodies coupled to columns or magnetic beads according to standard techniques. An aliquot of cells is analyzed for desired cell surface phenotype (e.g., CD4, CD8, CD3, CD14, etc.).

Cells are washed and resuspended at a concentration of 5×10$^5$ cells per ml of AIM-V modified as above and containing 5% FBS and 100 U/ml recombinant IL-2 (rIL-2) (supplemented AIM-V). Where the cells are isolated from an HIV$^+$ patient, 25 nM CD4-PE40 (a recombinant protein consisting of the HIV-1-binding CD4 domain linked to the translocation and ADP-ribosylation domains of Pseudomonas aeruginosa exotoxin A) is optionally added to the cell cultures for the remainder of the cell expansion to selectively remove HIV infected cells from the culture. CD4-PE40 has been shown to inhibit p24 production in HIV-1-infected cell cultures and to selectively kill HIV-1-infected cells.

To stimulate proliferation, OKT3 monoclonal antibody (Ortho Diagnostics) is added to a concentration of 10 ng/ml and the cells are plated in 24 well plates with 0.5 ml per well. The cells are cultured at 37° C. in a humidified incubator with 5% CO2 for 48 hours. Media is aspirated from the cells and 1 ml of vector-containing supernatant (described below) supplemented with 5 p1/ml of protanaine sulfate, 100 U/ml rIL-2, 100 U/ml penicillin, 0.25 µg/ml amphotericin B/ml, and an additional 100 µg/ml streptomycin (25 nM CD4-PE40 can be added as described above).

The expression of surface markers facilitates identification and purification of T cells. Methods of identification and isolation of T cells include fluorescence activated cell sorting (FACS), column chromatography, panning with magnetic beads, western blots, radiography, electrophoresis, capillary electrophoresis, high performance liquid chromatography (HPLC), thin layer chromatography (TLC), hyper-diffusion chromatography, and the like, and various immunological methods such as fluid or gel precipitin reactions, immnunodiffusion (single or double), immunonoelectrophoresis, radioimmunoassays (RIAs), enzyme-linked immunosorbent assays (ELISAs), immunofluorescent assays, and the like. For a review of immunological and immunoassay procedures in general, see Stites and Terr (eds.) 1991 Basic and Clinical Immunology (7th ed). For a discussion of how to make antibodies to selected antigens see, e.g. Coligan (1991) Current Protocols in Immunology Wiley/Greene, N.Y.; and Harlow and Lane (1989) Antibodies: A Laboratory Manual Cold Spring Harbor Press, New York; Stites et al. (eds.) Basic and Clinical Immunology (4th ea.)

In addition to the ex vivo uses described above, the packaging cell lines of the invention and the HIV packageable nucleic acids of the invention are useful generally in cloning methods. Packageable nucleic acids are packaged in an HIV particle and used to transform an HIV-infectible cell (e.g., a CD4+ cell) in vitro or in vivo. This provides one of skill with a technique for transforming cells with a nucleic acid of choice, e.g., in drug discovery assays, or as a tool in the study of gene regulation.

In Vivo Transformation

HIV particles containing therapeutic nucleic acids can be administered directly to the organism for transduction of cells in vivo. Administration is by any of the routes normally used for introducing a molecule into ultimate contact with blood or tissue cells. The packaged nucleic acids are administered in any suitable manner, preferably with pharmaceutically acceptable carriers. Suitable methods of administering such packaged nucleic acids in the context of the present invention to a patient are available, and although more than one route can be used to administer a particular composition, a particular route can often provide a more immediate and more effective reaction than another route.

Pharmaceutically acceptable carriers are determined in part by the particular composition being administered, as well as by the particular method used to administer the composition. Accordingly, there is a wide variety of suitable formulations of pharmaceutical compositions of the present invention, some of which are reviewed in PCT/US97/05272 (also see EXAMPLE 22).

The packaged nucleic acids are not freeze-dried (lyophilized) because HIV particles are destroyed by lyophilization. Injection solutions and suspensions can be prepared from sterile powders, granules, and tablets of the kind previously described. Cells transduced by the packaged nucleic acid as described above in the context of ex vivo therapy can also be administered intravenously or parenterally as described above. The dose administered to a subject, in the context of the present invention should be sufficient to effect a beneficial therapeutic response in the patient over time, or to inhibit infection by a pathogen. The dose will be determined by the efficacy of the particular vector employed and the condition of the patient, as well as the body weight or surface area of the subject to be treated. The size of the dose also will be determined by the existence, nature, and extent of any adverse side-effects that accompany the administration of a particular vector, or transduced cell type in a particular patient.

In determining the effective amount of the vector to be administered in the treatment of a disease, the physician or other clinician evaluates circulating plasma levels, vector toxicities, progression of the disease, and the production of anti-vector antibodies. In general, the dose equivalent of a naked nucleic; acid from a vector is from about 1 µg to 100 µg for a typical 70 kilogram patient, and doses of vectors which include a retroviral particle are calculated to yield an equivalent amount of inhibitor nucleic acid.

For administration, inhibitors and transduced cells of the present invention can be administered at a rate determined by the LD-50 of the inhibitor, vector, or transduced cell type, and the side-effects of the inhibitor, vector or cell type at various concentrations, as applied to the mass and overall health of the patient. Administration can be accomplished via single or divided doses.

Prior to infusion, blood samples are obtained and saved for analysis. Between $1 \times 10^8$ and $1 \times 10^{12}$ transduced cells are infused intravenously over 60–200 minutes. Leukopheresis, transduction and reinfusion are repeated every 2 to 3 months for a total of 4 to 6 treatments in a one year period.

Transduced cells are prepared for reinfusion according to established methods. See, Abrahamsen et al., *J. Clin. Apheresis* 6:48–53, 1991; Carter et al. *J. Clin. Arpheresis* 4:113–117, 1988; Aebersold et al., *J. Immunol. Methods* 112: 1–7, 1988; Muul et al., *J. Immunol. Methods* 101: 171–181, 1987; and Carter et al., *Transfusion* 27:362–365, 1987. After a period of about 24 weeks in culture, the cells should number between $1 \times 10^8$ and $1 \times 10^{12}$. In this regard, the growth characteristics of cells vary from patient to patient and from cell type to cell type. About 72 hours prior to reinfusion of the transduced cells, an aliquot is taken for analysis of phenotype, and percentage of cells expressing the therapeutic agent.

EXAMPLE 21

Sequence Variants

Having presented the nucleotide sequence of several lentiviral packaging and transfer vectors, as well as several therapeutic transgenes, this invention now also facilitates the creation and use of DNA molecules, and thereby proteins, which are derived from those disclosed but which vary in their precise nucleotide or amino acid sequence from those disclosed or those sequences which can be used as transgenes. Such variants can be obtained through a combination of standard molecular biology laboratory techniques and the nucleotide sequence information disclosed by this invention.

Variant DNA molecules include those created by standard DNA mutagenesis techniques, for example, M13 primer mutagenesis. Details of these techniques are provided in Sambrook et al. (In: *Molecular Cloning: A Laboratory Manual*, Cold Spring Harbor, N.Y., 1989, Ch. 15). By the use of such techniques, variants can be created which differ in minor ways from those disclosed. DNA molecules and nucleotide sequences which are derivatives of those specifically disclosed herein and which differ from those disclosed by the deletion, addition or substitution of nucleotides while still encoding a protein which possesses the functional characteristics of the lentiviral and/or transgene proteins are comprehended by this invention.

Also within the scope of this invention are small DNA molecules which are derived from the disclosed DNA molecules. Such small DNA molecules include oligonucleotides suitable for use as hybridization probes or PCR primers. As such, these small DNA molecules will comprise at least a segment of the lentiviral or transgene DNA molecules and for the purposes of PCR, will comprise at least a 20–50 nucleotide sequence of the lentiviral or transgene DNA or gene (i.e., at least 20–50 consecutive nucleotides of the lentiviral or transgene DNA or gene sequences). DNA molecules and nucleotide sequences which are derived from the disclosed DNA molecules as described above can also be defined as DNA sequences which hybridize under stringent conditions to the DNA sequences disclosed, or fragments thereof.

Hybridization conditions resulting in particular degrees of stringency will vary depending upon the nature of the hybridization method of choice and the composition and length of the hybridizing DNA used. Generally, the temperature of hybridization and the ionic strength (especially the $Na^+$ concentration) of the hybridization buffer will determine the stringency of hybridization. Calculations regarding hybridization conditions required for attaining particular degrees of stringency are discussed by Sambrook et al. (In: *Molecular Cloning: A Laboratory Manual*, Cold Spring Harbor, N.Y., 1989 ch. 9 and 11), herein incorporated by reference. By way of illustration only, a hybridization experiment can be performed by hybridization of a DNA molecule (for example, a deviation of the AADC cDNA) to a target DNA molecule (for example, the AADC cDNA) which has been electrophoresed in an agarose gel and transferred to a nitrocellulose membrane by Southern blotting (Southern, *J. Mol. Biol.* 98:503, 1975), a technique well known in the art and described in Sambrook et al. (*Molecular Cloning: A Laboratory Manual*, Cold Spring Harbor, N.Y., 1989).

Hybridization with a target probe labeled with $[^{32}P]$-dCTP is generally carried out in a solution of high ionic strength such as 6×SSC at a temperature that is 20–25° C. below the melting temperature, $T_m$, described below. For such Southern hybridization experiments where the target DNA molecule on the Southern blot contains 10 ng of DNA or more, hybridization is typically carried out for 6–8 hours using 1–2 ng/ml radiolabeled probe (of specific activity equal to $10^9$ CPM/µg or greater). Following hybridization, the nitrocellulose filter is washed to remove background hybridization. The washing conditions should be as stringent as possible to remove background hybridization but to retain a specific hybridization signal. The term $T_m$ represents the temperature above which, under the prevailing ionic conditions, the radiolabeled probe molecule will not hybridize to its target DNA molecule. The $T_m$ of such a hybrid molecule can be estimated from the following equation (Bolton and McCarthy, *Proc. Natl. Acad. Sci. USA* 48:1390, 1962): $T_m$=81.5° C.−16.6($\log_{10}$[Na$^+$])+0.41(%G+C)−0.63(% formamide)−(600/1); where 1=the length of the hybrid in base pairs.

This equation is valid for concentrations of Na$^+$ in the range of 0.01 M to 0.4 M, and it is less accurate for calculations of $T_m$ in solutions of higher [Na$^+$]. The equation is also primarily valid for DNAs whose G+C content is in the range of 30% to 75%, and it applies to hybrids greater than 100 nucleotides in length (the behavior of oligonucleotide probes is described in detail in Ch. 11 of Sambrook et al. (*Molecular Cloning: A Laboratory Manual*, Cold Spring Harbor, N.Y., 1989).

Thus, by way of example, for a 150 base pair DNA probe derived from the open reading frame of the AADC cDNA (with a hypothetical %GC=45%), a calculation of hybridization conditions required to give particular stringencies can be made as follows: For this example, it is assumed that the filter will be washed in 0.3×SSC solution following hybridization, thereby: [Na$^+$]=0.045 M; %GC=45%; Formamide concentration=0; 1=150 base pairs; $T_m$=81.5−16.6 ($\log_{10}$[Na$^+$])+(0.41×45)−(600/150); and so $T_m$=74.4° C.

The $T_m$ of double-stranded DNA decreases by 1–1.5° C. with every 1% decrease in homology (Bonner et al., *J. Mol. Biol.* 81:123, 1973). Therefore, for this given example, washing the filter in 0.3×SSC at 59.4–64.4° C. will produce a stringency of hybridization equivalent to 90%; that is, DNA molecules with more than 10% sequence variation relative to the target cDNA (for example AADC) will not hybridize. Alternatively, washing the hybridized filter in 0.3×SSC at a temperature of 65.4–68.40° C. will yield a hybridization stringency of 94%; that is, DNA molecules with more than 6% sequence variation relative to the target cDNA molecule (for example AADC) will not hybridize. The above example is given entirely by way of theoretical illustration. One skilled in the art will appreciate that other hybridization techniques can be utilized and that variations in experimental conditions will necessitate alternative calculations for stringency.

In particular embodiments of the present invention, stringent conditions can be defined as those under which DNA molecules with more than 25%, 15%, 10%, 6% or 2% sequence variation (also termed "mismatch") will not hybridize.

The degeneracy of the genetic code further widens the scope of the present invention as it enables major variations in the nucleotide sequence of a DNA molecule while maintaining the amino acid sequence of the encoded protein. For example, alanine is encoded in the cDNA by the nucleotide codon triplet GCA. However, because of the degeneracy of the genetic code, three other nucleotide codon triplets, GCT, GCG and GCC, also code for alanine. Thus, the nucleotide sequence of a cDNA could be changed at the alanine position to any of these three codons without affecting the amino acid composition of the encoded protein or the characteristics of the protein. Based upon the degeneracy of the genetic code, variant DNA molecules can be derived from the cDNA molecules disclosed herein using standard DNA mutagenesis techniques as described above, or by synthesis of DNA sequences. DNA sequences which do not hybridize under stringent conditions to the cDNA sequences disclosed by virtue of sequence variation based on the degeneracy of the genetic code are herein also comprehended by this invention.

The invention also includes DNA sequences that are substantially identical to any of the DNA sequences disclosed herein, where substantially identical means a sequence that has identical nucleotides in at least 75%, 80%, 85%, 90%, 95% or 98% of the aligned sequences.

One skilled in the art will recognize that the DNA mutagenesis techniques described above can be used not only to produce variant DNA molecules, but will also facilitate the production of proteins which differ in certain structural aspects from the lentiviral or transgene proteins, yet which proteins are clearly derivative of this protein and which maintain the essential characteristics of the lentiviral or transgene protein. Newly derived proteins can also be selected in order to obtain variations on the characteristic of the lentiviral or transgene protein, as will be more fully described below. Such derivatives include those with variations in amino acid sequence including minor deletions, additions and substitutions.

While the site for introducing an amino acid sequence variation is predetermined, the mutation per se need not be predetermined. For example, in order to optimize the performance of a mutation at a given site, random mutagenesis can be conducted at the target codon or region and the expressed protein variants screened for the optimal combination of desired activity. Techniques for making substitution mutations at predetermined sites in DNA having a known sequence as described above are well known.

Amino acid substitutions are typically of single residues; insertions usually will be on the order of about from 1 to 10 amino acid residues; and deletions will range about from 1 to 30 residues. Deletions or insertions can be made in adjacent pairs, i.e., a deletion of 2 residues or insertion of 2 residues. Substitutions, deletions, insertions or any combination thereof can be combined to arrive at a final construct. Obviously, the mutations that are made in the DNA encoding the protein must not place the sequence out of reading frame and ideally will not create complementary regions that could produce secondary mRNA structure.

Substitutional variants are those in which at least one residue in the amino acid sequence has been removed and a different residue inserted in its place. Such substitutions generally are made conservatively, as defined above.

Substantial changes in function or immunological identity are made by selecting substitutions that are less conservative than those defined above, i.e., selecting residues that differ more significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. The substitutions which in general are expected to produce the greatest changes in protein properties will be those in which (a) a hydrophilic residue, e.g., seryl or threonyl, is substituted for (or by) a hydrophobic residue, e.g., leucyl, isoleucyl, phenylalanyl, valyl or alanyl; (b) a cysteine or proline is substituted for (or by) any other residue; (c) a residue having an electropositive side chain, e.g., lysyl, arginyl, or histadyl, is substituted for (or by) an electronegative residue, e.g., glutamyl or aspartyl; or (d) a residue having a bulky side chain, e.g., phenylalanine, is substituted for (or by) one not having a side chain, e.g., glycine.

Substitutions of the lentiviral or transgene amino acid sequence can be made either in regions that are highly conserved between species, or regions that share less conservation between species.

The effects of these amino acid substitutions or deletions or additions can be assessed for derivatives of the lentiviral or transgene protein by assays in which DNA molecules encoding the derivative proteins are introduced into the packaging or transfer vector using routine procedures. These vectors would be used to transform cells as described in EXAMPLES 1–14, and analyzed for their ability to allow expression (for example by monitoring the viral titer) of the transgene within the transfer vector.

EXAMPLE 22

Pharmaceutical Compositions and Modes of Administration

Various delivery systems for administering the combined lentiviral therapy of the present invention are known, and include e.g., encapsulation in liposomes, microparticles, microcapsules, receptor-mediated endocytosis (see Wu and Wu, *J. Biol. Chem.* 1987, 262:4429–32). Methods of introduction include, but are not limited to, intradermal, intramuscular, intraperitoneal, intravenous, subcutaneous, intranasal, and oral routes. The compounds can be administered by any convenient route, for example by infusion or bolus injection, by absorption through epithelial or mucocutaneous linings (e.g., oral mucosa, rectal and intestinal mucosa, etc.) and can be administered together with other biologically active agents. Administration can be systemic or local. In addition, the pharmaceutical compositions can be introduced into the central nervous system by any suitable route, including intraventricular and intrathecal injection; intraventricular injection can be facilitated by an intraventricular catheter, for example, attached to a reservoir, such as an Ommaya reservoir.

In one embodiment, it may be desirable to administer the pharmaceutical compositions of the invention locally to the area in need of treatment, for example, by local infusion during surgery, topical application, e.g., in conjunction with a wound dressing after surgery, by injection, through a catheter, by a suppository or an implant, such as a porous, non-porous, or gelatinous material, including membranes, such as silastic membranes, or fibers. In one embodiment, administration can be by direct injection at the site (or former site) of a malignant tumor or neoplastic or pre-neoplastic tissue.

The use of liposomes as a delivery vehicle is one delivery method of interest. The liposomes fuse with the target site and deliver the contents of the lumen intracellularly. The liposomes are maintained in contact with the target cells for a sufficient time for fusion to occur, using various means to maintain contact, such as isolation and binding agents. Liposomes can be prepared with purified proteins or peptides that mediate fusion of membranes, such as Sendai virus or influenza virus. The lipids can be any useful combination of known liposome forming lipids, including cationic lipids, such as phosphatidylcholine. Other potential lipids include neutral lipids, such as cholesterol, phosphatidyl serine, phosphatidyl glycerol, and the like. For preparing the liposomes, the procedure described by Kato et al. (*J. Biol. Chem.* 1991, 266:3361) can be used.

The present invention also provides pharmaceutical compositions which include a therapeutically effective amount of the lentiviral vectors, alone or with a pharmaceutically acceptable carrier.

Delivery Systems

Such carriers include, but are not limited to, saline, buffered saline, dextrose, water, glycerol, ethanol, and combinations thereof. The carrier and composition can be sterile, and the formulation suits the mode of administration. The composition can also contain minor amounts of wetting or emulsifying agents, or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulations can include standard carriers such as pharmaceutical grades of mannitol, lactose, starch, magnesium stearate, sodium saccharine, cellulose, and magnesium carbonate.

The amount of the inducing agent and disrupting agent that will be effective in the treatment of a particular disorder or condition will depend on the nature of the disorder or condition, and can be determined by standard clinical techniques. In addition, in vitro assays can optionally be employed to help identify optimal dosage ranges. The precise dose to be employed in the formulation will also depend on the route of administration, and the seriousness of the disease or disorder, and should be decided according to the judgment of the practitioner and each subject's circumstances. Effective doses can be extrapolated from dose-response curves derived from in vitro or animal model test systems.

The invention also provides a pharmaceutical pack or kit comprising one or more containers filled with one or more of the ingredients of the pharmaceutical compositions. Optionally associated with such container(s) can be a notice in the form prescribed by a governmental agency regulating the manufacture, use or sale of pharmaceuticals or biological products, which notice reflects approval by the agency of manufacture, use or sale for human administration. Instructions for use of the composition can also be included.

The pharmaceutical compositions or methods of treatment can be administered in combination with other therapeutic treatments, such as other antineoplastic or antitumorigenic therapies.

Any of the common pharmaceutical carriers, such as sterile saline solution or sesame oil, can be used. The medium can also contain conventional pharmaceutical adjunct materials such as, for example, pharmaceutically acceptable salts to adjust the osmotic pressure, buffers, preservatives and the like. Other media that can be used in the present invention are normal saline and sesame oil.

Embodiments of the invention comprising medicaments can be prepared with conventional pharmaceutically acceptable carriers, adjuvants and counterions as would be known to those of skill in the art.

The lentiviral vectors of the present invention are administered in an amount effective to produce a therapeutic effect in a subject. The exact dosage of lentiviral particles to be administered is dependent upon a variety of factors, including the age, weight, and sex of the subject to be treated, and the nature and extent of the disease or disorder to be treated. The lentiviral particles can be administered as part of a preparation having a titer of lentiviral particles of at least $1 \times 10^{10}$ pfu/ml, and in general not exceeding $2 \times 10^{11}$ pfu/ml. The lentiviral particles can be administered in combination with a pharmaceutically acceptable carrier in a volume up to 10 ml. The pharmaceutically acceptable carrier can be, for example, a liquid carrier such as a saline solution, protamine sulfate (Elkins-Sinn, Inc., Cherry Hill, N.J.), or Polybrene (Sigma Chemical) as well as others described herein.

Having illustrated and described the principles of generating several different lentiviral transforming and packaging vectors for use in the delivery of therapeutic transgenes to a subject, the art of the invention can be modified in arrangement and detail without departing from such principles. In view of the many possible embodiments to which the principles of my invention can be applied, it should be recognized that the illustrated embodiments are only examples of the invention and should not be taken as a limitation on the scope of the invention. Rather, the scope of the invention is in accord with the following claims. I therefore claim as my invention all that comes within the scope and spirit of these claims.

I claim:

1. An HIV-2 packaging vector comprising a 5' splice donor site (SD) and an upstream and a downstream packaging signal sequence, wherein both the upstream and downstream packaging signal sequences are functionally deleted to reduce packaging of progeny viral RNA by more than 80%, but the SD is functionally intact, wherein functional deletion of the upstream and downstream packaging signal sequences comprises:

deletion of nucleotides 306–458 upstream of the SD, and deletion of nucleotides 486–538 downstream of the SD; or deletion of nucleotides 306–370 upstream of the SD, and deletion of nucleotides 486–538 downstream of the SD; or deletion of nucleotides 371–458 upstream of the SD, and deletion of nucleotides 486–538 downstream of the SD.

2. The packaging vector of claim 1, further comprising a 3' LTR, a 5' LTR, and a heterologous promotor CMV.

3. The packaging vector of claim 1, further comprising a functionally deleted 3' LTR.

4. The packaging vector of claim 3, wherein the 3' LTR is replaced with a heterologous transcriptional termination sequence.

5. An HIV-2 packaging vector, comprising a 5' splice donor site (SD) and an upstream and a downstream packaging signal sequence, wherein both the upstream and downstream packaging signal sequences are functionally deleted to reduce packaging of progeny viral RNA by more than 80%, but the SD is functionally intact, wherein the upstream packaging signal corresponds to nucleotides downstream from nucleotide 300 and upstream from the SD, and the downstream packaging signal corresponds to nucleotides downstream from the SD and upstream from nucleotide 539.

6. The packaging vector of claim 1, wherein the functional deletions in the packaging vector decreases syncytia induction relative to an HIV-2 vector having functional upstream and downstream packaging signal sequences.

7. An isolated cell that expresses or has been transfected with the packaging vector of claim 1.

8. An isolated cell that expresses or has been transfected with the packaging vector of claim 5.

9. The packaging vector of claim 1, wherein functional deletion of the upstream and downstream packaging signal sequences comprises deletion of nucleotides 306–458 upstream of the SD, and deletion of nucleotides 486–538 downstream of the SD.

10. The packaging vector of claim 1, wherein functional deletion of the upstream and downstream packaging signal sequences comprises deletion of nucleotides 306–370 upstream of the SD, and deletion of nucleotides 486–538 downstream of the SD.

11. The packaging vector of claim 1, wherein functional deletion of the upstream and downstream packaging signal sequences comprises deletion of nucleotides 371–458 upstream of the SD, and deletion of nucleotides 486–538 downstream of the SD.

12. The HIV-2 packaging vector of claim 1, further comprising a functionally deleted envelope, wherein the function of the envelope is provided in trans by a second vector.

13. The HIV-2 packaging vector of claim 1, wherein the HIV-2 packaging vector comprises SEQ ID NO: 7, 21 or 22 and the second vector comprises SEQ ID NO: 9 or 23.

14. The HIV-2 packaging vector of claim 1, wherein both the upstream and downstream packaging signal sequences are functionally deleted to eliminate packaging of progeny viral RNA.

15. The packaging vector of claim 5, further comprising a 3' LTR, a 5' LTR, and a heterologous promotor CMV.

16. The packaging vector of claim 5, further comprising a functionally deleted 3' LTR.

17. The packaging vector of claim 16 wherein the 3'LTR is replaced with a heterologous transcriptional termination sequence.

18. The packaging vector of claim 5, wherein the functional deletions in the packaging vector decreases syncytia induction relative to an HIV2 vector having functional upstream and downstream packaging signal sequences.

19. The HIV-2 packaging vector of claim 5, further comprising a functionally deleted envelope, wherein the function of the envelope is provided in trans by a second vector.

20. The HIV-2 packaging vector of claim 5, wherein both the upstream and downstream packaging signal sequences are functionally deleted to eliminate packaging of progeny viral RNA.

* * * * *

UNITED STATES PATENT AND TRADEMARK OFFICE
CERTIFICATE OF CORRECTION

PATENT NO. : 7,226,780 B2
APPLICATION NO. : 10/731988
DATED : June 5, 2007
INVENTOR(S) : Suresh K. Arya It is certified that error appears in the above-identified patent and that said Letters Patent is hereby corrected as shown below:

In the Specification:

Column 9, line 54, "Olig nucleotide" should be --Oligonucleotide--.

Column 30, Table 2, the second and third items under the column "Progeny p27", "0.04 0.2" and "0.2 0.1" should be --0.4 ± 0.2-- and --0.2 ± 0.1--, respectively, so that the Table reads as follows:

TABLE 2
Infectivity in CEM cells of progeny virus produced by Transfected CEM cells

| Clone | Syncytia Induction | Progeny p27 |
|---|---|---|
| pROD-3(WT) | +++ | 1.0 |
| (PK2) | +++ | 0.4 ± 0.2 |
| (PK36) | +++ | 0.2 ± 0.1 |
| (PK8) | (-) | 0.01 |
| (SD36) | (-) | 0.03 |
| pROD-3(PA) | (-) | 0.7 |
| (SD36/PA) | (-) | 0.01 |
| pROD-3(PUR) | ND | ND |
| pSP64/pPUR | (-) | (-) |

Column 34, line 31, "C13 X—C" should be --C-X-C--.

UNITED STATES PATENT AND TRADEMARK OFFICE
CERTIFICATE OF CORRECTION

PATENT NO. : 7,226,780 B2
APPLICATION NO. : 10/731988
DATED : June 5, 2007
INVENTOR(S) : Suresh K. Arya It is certified that error appears in the above-identified patent and that said Letters Patent is hereby corrected as shown below:

In the Claims:

Column 116, line 5, claim 13, "claim 1" should be --claim 12--.

Signed and Sealed this

Second Day of December, 2008

JON W. DUDAS
*Director of the United States Patent and Trademark Office*

SEQUENCE LISTING

<160> NUMBER OF SEQ ID NOS: 32

<210> SEQ ID NO 1
<211> LENGTH: 250
<212> TYPE: DNA
<213> ORGANISM: Human immunodeficiency virus type 2

<400> SEQUENCE: 1

```
gttggcgcct gaacagggac ttgaagaaga ctgagaagtc ttggaacacg gctgagtgaa      60
ggcagtaagg gcggcaggaa caaaccacga cggagtgctc ctagaaaggc gcgggccgag     120
gtaccaaagg cagcgtgtgg agcgggagga gaagaggcct ccgggtgaag gtaagtacct     180
acaccaaaaa ctgtagccga aagggcttgc tatcctacct ttagacaggt agaagattgt     240
gggagatggg                                                            250
```

<210> SEQ ID NO 2
<211> LENGTH: 196
<212> TYPE: DNA
<213> ORGANISM: Artificial Sequence
<220> FEATURE:
<223> OTHER INFORMATION: Description of Artificial Sequence: pROD(PK36)
      leader sequence

<400> SEQUENCE: 2

```
gttggcgcct gaacagggac ttgaagaaga ctgagaagtc ttggaacacg gctgagtgaa      60
ggcagtaagg gcggcaggaa caaaccacga cggagtgctc ctagaaaggc gcgggccgag     120
gtaccaaagg gagcgtgtgg agcgggagga gaaagaggct ccgggtgaag gtaagtacct     180
acacctggga gatggg                                                    196
```

<210> SEQ ID NO 3
<211> LENGTH: 97
<212> TYPE: DNA
<213> ORGANISM: Artificial Sequence
<220> FEATURE:
<223> OTHER INFORMATION: Description of Artificial Sequence: pROD(SK36)
      leader sequence

<400> SEQUENCE: 3

```
gttggctccg ggtgaaggta agtacctaca ccaaaaactg tagccgaaag ggcttgctat      60
cctacctttg acaggtagaa gattgtggga gatggg                                97
```

<210> SEQ ID NO 4
<211> LENGTH: 43
<212> TYPE: DNA
<213> ORGANISM: Artificial Sequence
<220> FEATURE:
<223> OTHER INFORMATION: Description of Artificial Sequence: pROD(SD36)
      Leader sequence

<400> SEQUENCE: 4

```
gttggctccg ggtgaaggta agtacctaca cgtgggagat ggg                         43
```

<210> SEQ ID NO 5
<211> LENGTH: 109
<212> TYPE: DNA
<213> ORGANISM: Artificial Sequence
<220> FEATURE:
<223> OTHER INFORMATION: Description of Artificial Sequence: pROD(CG36)
      Leader sequence -continued

```
<400> SEQUENCE: 5
gttggcgcct gaacagggac ttgaagaaga ctgagaagtc ttggaacacg gctgagtgaa    60
ggcagtaagg ctccgggtga aggtaagtac ctacaccgtg ggagatggg              109

<210> SEQ ID NO 6
<211> LENGTH: 132
<212> TYPE: DNA
<213> ORGANISM: Artificial Sequence
<220> FEATURE:
<223> OTHER INFORMATION: Description of Artificial Sequence: pROD(MR36)
      Leader sequence

<400> SEQUENCE: 6
gttgggcggc aggaacaaac cacgacggag tgctcctaga aaggcgcggg ccgaggtacc    60
aaagggagcg tgtggagcgg gaggagaaag aggctccggg tgaaggtaag tacctacacc   120
gtgggagatg gg                                                        132

<210> SEQ ID NO 7
<211> LENGTH: 82
<212> TYPE: DNA
<213> ORGANISM: Artificial Sequence
<220> FEATURE:
<223> OTHER INFORMATION: Description of Artificial Sequence: pROD
                        (SD36/EM) envelope region

<400> SEQUENCE: 7
acagaggctt ttgatgcata ggtagcgtga gatcttagtg cataggtagc gtgagatctt    60
agtgcaaaga tcgaataata ca                                              82

<210> SEQ ID NO 8
<211> LENGTH: 30
<212> TYPE: DNA
<213> ORGANISM: Human immunodeficiency virus type 2

<400> SEQUENCE: 8
acagaggctt ttgatgcatg gaataataca                                      30

<210> SEQ ID NO 9
<211> LENGTH: 4203
<212> TYPE: DNA
<213> ORGANISM: Artificial Sequence
<220> FEATURE:
<223> OTHER INFORMATION: Description of Artificial Sequence: pCM-ENV
                        (ROD) vector
<220> FEATURE:
<221> NAME/KEY: promoter
<222> LOCATION: (1)..(795)
<223> OTHER INFORMATION: CMV IE promotor

<400> SEQUENCE: 9
tcaatattgg ccattagcca tattattcat tggttatata gcataaatca atattggcta    60
ttggccattg catacgttgt atctatatca taatatgtac atttatattg gctcatgtcc   120
aatatgaccg ccatgttggc attgattatt gactagttat taatagtaat caattacggg   180
gtcattagtt catagcccat atatggagtt ccgcgttaca taacttacgg taaatggccc   240
gcctggctga ccgcccaacg accccgccc attgacgtca ataatgacgt atgttcccat    300
agtaacgcca atagggactt tccattgacg tcaatgggtg gagtatttac ggtaaactgc   360
ccacttggca gtacatcaag tgtatcatat gccaagtccg cccctattg acgtcaatga    420 cggtaaatgg cccgcctggc attatgccca gtacatgacc ttacgggact tcctacttg   480
```

| | | | | |
|---|---|---|---|---|
| gcagtacatc | tacgtattag | tcatcgctat | taccatggtg | atgcggtttt | ggcagtacac | 540 |
| caatgggcgt | ggatagcggt | ttgactcacg | gggatttcca | agtctccacc | ccattgacgt | 600 |
| caatgggagt | ttgttttggc | accaaaatca | acgggacttt | ccaaaatgtc | gtaataaccc | 660 |
| cgccccgttg | acgcaaatgg | gcggtaggcg | tgtacggtgg | gaggtctata | taagcagagc | 720 |
| tcgtttagtg | aaccgtcaga | tcactagaag | ctttattgcg | gtagtttatc | acagttaaat | 780 |
| tgctaacgca | gtcagtgctt | ctgacacaac | ggtctcgaac | ttaagctgca | gaagttggtc | 840 |
| gtgaggcact | gggcaggtaa | gtatcaaggt | tacaagacag | gtttaaggag | accaatagaa | 900 |
| actgggcttg | tcgagacaga | gaagactctt | gcgtttctga | taggcaccta | ttggtcttac | 960 |
| tgacatccac | tttgcctttc | tctccacagg | tgtccactcc | cagttcaatt | acagctctta | 1020 |
| aggctagagt | acttaatacg | actcactata | ggctagcctc | gataccaccag | acaagtgagt | 1080 |
| atgatgaatc | agctgcttat | tgccatttta | ttagctagtg | cttgcttagt | atattgcacc | 1140 |
| caatatgtaa | ctgttttcta | tggcgtaccc | acgtggaaaa | atgcaaccat | tcccctcttt | 1200 |
| tgtgcaacca | gaaatagggga | tacttgggga | accatacagt | gcttgcctga | caatgatgat | 1260 |
| tatcaggaaa | taactttgaa | tgtaacagag | gcttttgatg | catggaataa | tacagtaaca | 1320 |
| gaacaagcaa | tgaaagatgt | ctggcatcta | ttcgagacat | caataaaaacc | atgtgtcaaa | 1380 |
| ctaacacctt | tatgtgtagc | aatgaaatgc | agcagcacag | agagcagcat | agggaacaac | 1440 |
| acaacctcaa | agagcacaag | cacaaccaca | accacaccca | cagaccagga | gcaagagata | 1500 |
| agtgaggata | ctccatgcgc | acgcgcagac | aactgctcag | gattgggaga | ggaagaaacg | 1560 |
| atcaattgcc | agttcaatat | gacaggatta | gaaagagata | agaaaaaaca | gtataatgaa | 1620 |
| acatggtact | caaaagatgt | ggtttgtgag | acaaataata | gcacaaatca | gacccagtgt | 1680 |
| tacatgaacc | attgcaacac | atcagtcatc | acagaatcat | gtgacaagca | ctattgggat | 1740 |
| gctataaggt | ttagatactg | tgcaccaccg | ggttatgccc | tattaagatg | taatgatacc | 1800 |
| aattattcag | gctttgcacc | caactgttct | aaagtagtag | cttctacatg | caccaggatg | 1860 |
| atggaaacgc | aaacttccac | atggtttggc | tttaatggca | ctagagcaga | gaatagaaca | 1920 |
| tatatctatt | ggcatggcag | agataataga | actatcatca | gcttaaacaa | atattataat | 1980 |
| ctcagtttgc | attgtaagag | gccagggaat | aagatagtga | aacaaataat | gcttatgtca | 2040 |
| ggacatgtgt | ttcactccca | ctaccagccg | atcaataaaa | gacccagaca | agcatggtgc | 2100 |
| tggttcaaag | gcaaatggaa | agacgccatg | caggaggtga | aggaaaccct | tgcaaaacat | 2160 |
| cccaggtata | gaggaaccaa | tgcacaagg | aatattagct | ttgcagcgcc | aggaaaaggc | 2220 |
| tcagacccag | aagtagcata | catgtggact | aactgcagag | gagagtttct | ctactgcaac | 2280 |
| atgacttggt | tcctcaattg | gatagagaat | aagacacacc | gcaattatgc | accgtgccat | 2340 |
| ataaagcaaa | taattaacac | atggcataag | gtagggagaa | atgtatattt | gcctcccagg | 2400 |
| gaaggggagc | tgtcctgcaa | ctcaacagta | accagcataa | ttgctaacat | tgactggcaa | 2460 |
| aacaataatc | agacaaacat | tacctttagt | gcagaggtgg | cagaactata | cagattggag | 2520 |
| ttgggagatt | ataaattggt | agaaataaca | ccaattggct | tcgcacctac | aaaagaaaaa | 2580 |
| agatactcct | ctgctcacgg | gagacataca | agaggtgtgt | tcgtgctagg | gttcttgggt | 2640 |
| tttctcgcaa | cagcaggttc | tgcaatgggc | gcggcgtccc | tgaccgtgtc | ggctcagtcc | 2700 |
| cggactttac | tggccgggat | agtgcagcaa | cagcaacagc | tgttggacgt | ggtcaagaga | 2760 |
| caacaagaac | tgttgcgact | gaccgtctgg | ggaacgaaaa | acctccaggc | aagagtcact | 2820 |
| gctatagaga | agtacctaca | ggaccaggcg | cggctaaatt | catgggatg | tgcgtttaga | 2880 |

-continued

```
caagtctgcc acactactgt accatgggtt aatgattcct tagcacctga ctgggacaat    2940
atgacgtggc aggaatggga aaaacaagtc cgctacctgg aggcaaatat cagtaaaagt    3000
ttagaacagg cacaaattca gcaagagaaa aatatgtatg aactacaaaa attaaatagc    3060
tgggatattt ttggcaattg gtttgactta acctcctggg tcaagtatat tcaatatgga    3120
gtgcttataa tagtagcagt aatagcttta agaatagtga tatatgtagt acaaatgtta    3180
agtaggctta gaaagggcta taggcctgtt ttctcttccc ccccggttat atccaacaga    3240
tccatatcca caaggaccgg ggacagccag ccaacgaaga aacagaagaa gacggtggaa    3300
gcaacggtgg agacagatac tggccctggc cgatagcata tatacatttc ctgatccgcc    3360
agctgattcg cctcttgacc agactataca gcatctgcag ggacttacta tccaggagct    3420
tcctgaccct ccaactcatc taccagaatc tcagagactg gctgagactt agaacagcct    3480
tcttgcaata tgggtgcgag tggatccaag aagcattcca ggccgccgcg agggctacaa    3540
gagagactct tgcgggcgcg tgcagggggct tgtggagggt attggaacga atcgggaggg    3600
gaatactcgc ggttccaaga aggatcagac agggagcaga aatcgcctcc tgtgagggac    3660
ggcagtatag ccagggagac tttatgaata ctccatgggg cggccgcttc gagcagacat    3720
gataagatac attgatgagt ttggacaaac cacaactaga atgcagtgaa aaaaatgctt    3780
tatttgtgaa atttgtgatg ctattgcttt atttgtaacc attataagct gcaataaaca    3840
agttaacaac aacaattgca ttcattttat gtttcaggtt caggggggaga tgtgggaggt    3900 tttttaaagc aagtaaaacc tctacaaatg tggtaaaatc gataaggatc cgggctggcg    3960
taatagcgaa gaggcccgca ccgatcgccc ttcccaacag ttgcgcagcc tgaatggcga    4020
atggacgcgc cctgtagcgg cgcattaagc gcggcgggtg tggtggttac gcgcagcgtg    4080
accgctacac ttgccagcgc cctagcgccc gctcctttcg ctttcttccc ttcctttctc    4140
gccacgttcg ccggctttcc ccgtcaagct ctaaatcggg ggctcccttt agggttccga    4200
ttt                                                                   4203
```

<210> SEQ ID NO 10
<211> LENGTH: 560
<212> TYPE: DNA
<213> ORGANISM: Simian immunodeficiency virus

<400> SEQUENCE: 10

```
gctctgtatt cagtcgctct gcggagaggc tggcagattg agccctggga ggttctctcc     60
agcactagca ggtagagcct gggtgttccc tgctagactc tcaccagcac ttggccggtg    120
ctgggcagag tgactccacg cttgcttgct taaagccctc ttcaataaag ctgccatttt    180
agaagtaagc tagtgtgtgt tcccatctct cctagccgcc gcctggtcaa ctcggtactc    240
aataataaga agaccctggt ctgttaggac cctttctgct ttgggaaacc gaagcaggaa    300
aatccctagc agattggcgc ctgaacaggg acttgaagga gagtgagaga ctcctgagta    360
cggctgagtg aaggcagtaa gggcggcagg aaccaaccac gacggagtgc tcctataaag    420
gcgcgggtcg gtaccagacg gcgtgaggag cgggagagga agaggcctcc ggttgcaggt    480
aagtgcaaca caaaaaagaa atagctgtct tttatccagg aagggggtaat aagatagagt    540 gggagatggg cgtgagaaac                                                 560
```

<210> SEQ ID NO 11
<211> LENGTH: 54
<212> TYPE: DNA
<213> ORGANISM: Artificial Sequence

```
<220> FEATURE:
<223> OTHER INFORMATION: Description of Artificial Sequence: pSIV(SD36)
      Leader sequence

<400> SEQUENCE: 11
gattggctcc ggttgcaggt aagtgcaaca cagtgggaga tgggcgtgag aaac            54

<210> SEQ ID NO 12
<211> LENGTH: 249
<212> TYPE: DNA
<213> ORGANISM: Artificial Sequence
<220> FEATURE:
<223> OTHER INFORMATION: Description of Artificial Sequence: pSIV(SDM)
      Leader sequence

<400> SEQUENCE: 12
gattggcgcc tgaacaggga cttgaaggag agtgagagac tcctgagtac ggctgagtga     60
aggcagtaag ggcggcagga accaaccacg acggagtgct cctataaagg cgcgggtcgg    120
taccagacgg cgtgaggagc gggagaggaa gaggcctccg gttgatatcg agtgcaacac    180
aaaaaagaaa tagctgtctt ttatccagga agggtaata agatagagtg ggagatgggc     240
gtgagaaac                                                            249

<210> SEQ ID NO 13
<211> LENGTH: 550
<212> TYPE: DNA
<213> ORGANISM: Human immunodeficiency virus type 2

<400> SEQUENCE: 13
gttcgctctg cggagaggct ggcagattga gccctgggag gttctctcca gcactagcag     60
tggtcacctg ggtgttccct gctagactct caccagtgct tggccggcac tgggcagacg    120
gctccacgct tgcttgctta aaagacctct taataaagct gccagttaga agcaagttaa    180
gtgtgtgctc ccatctctcc tagtcgccgc ctggtcattc ggtgttcatc taaagtaaca    240
agaccctggt ctgttaggac cctttctgct ttgggaaacc aaggcaggaa atccctagc     300 aggttggcgc ccgaacaggg acttgaagaa gactgagaag ccttggaaca cggctgagtg    360
aaggcagtaa gggcggcagg aacaaaccac gacggagtgc tcctagaaaa gcgcaggccg    420
aggtaccaag gcggcgtgt ggagcgggag tgaaagaggc ctccgggtga aggtaagtgc    480
ctacaccaaa tacagtagcc agaagggctt gttatcctac ctttagacgg gtagaagatt    540
gtgggagatg                                                           550

<210> SEQ ID NO 14
<211> LENGTH: 2769
<212> TYPE: DNA
<213> ORGANISM: Artificial Sequence
<220> FEATURE:
<223> OTHER INFORMATION: Description of Artificial Sequence:
      pSGT-5(SDM/RRE1)
<220> FEATURE:
<221> NAME/KEY: misc_feature
<222> LOCATION: (1536)..(1835)
<223> OTHER INFORMATION: RRE sequence
<220> FEATURE:
<221> NAME/KEY: misc_feature
<222> LOCATION: (1)..(555)
<223> OTHER INFORMATION: U3 sequence
<220> FEATURE:
<221> NAME/KEY: misc_feature
<222> LOCATION: (729)..(856)
<223> OTHER INFORMATION: U5 sequence
```

```
<220> FEATURE:
<221> NAME/KEY: misc_feature
<222> LOCATION: (1101)..(1508)
<223> OTHER INFORMATION: gag sequence
<220> FEATURE:
<221> NAME/KEY: misc_feature
<222> LOCATION: (1836)..(1863)
<223> OTHER INFORMATION: multiple cloning site
<220> FEATURE:
<221> NAME/KEY: misc_feature
<222> LOCATION: (2042)..(2595)
<223> OTHER INFORMATION: U3 sequence
<220> FEATURE:
<221> NAME/KEY: misc_feature
<222> LOCATION: (2596)..(2769)
<223> OTHER INFORMATION: R sequence
<220> FEATURE:
<221> NAME/KEY: misc_feature
<222> LOCATION: (556)..(728)
<223> OTHER INFORMATION: R sequence

<400> SEQUENCE: 14
ggaagggctg tattacagtg ataggagacg tagagtccta gacatatact tagaaaagga    60
agagggaata attggagact ggcagaacta tactcatgga ccaggagtaa ggtatccaaa   120
gttctttggg tggttatgga agctagtacc agtagatgtc ccacaagagg gagatgacag   180
tgagactcac tgcttagtgc atccagcaca acaagcagg tttgatgacc cgcatggaga    240
aacattagtt tggaggtttg accccacgct agcttttagc tacgaggcct ttattcgata   300
cccagaggag tttgggtaca agtcaggcct gccagaggat gaatggaagg caagactgaa   360
agcaagaggg ataccgttta gctaaaaaca ggaacagcta tacttggtca gggcaggaag   420
taactaacag aaaacagctg agactgcagg gactttccag aaggggctgt taccagggga   480
gggacatggg aggagccggt ggggaacgcc ctcatacttt ctgtataaat gtacccgcta   540
ctcgcattgt attcagtcgc tctgcggaga ggctggcaga ttgagccctg ggaggttctc   600
tccagcacta gcaggtagag cctgggtgtt ccctgctaga ctctcaccag tgcttggccg   660
gcactgggca gacggctcca cgcttgcttg cttaaaagac ctcttaataa agctgccagt   720
tagaagcaag ttaagtgtgt gctcccatct ctcctagtcg ccgcctggtc attcggtgtt   780
catctaaagt aacaagaccc tggtctgtta ggacccttc tgctttggga aaccaaggca    840
ggaaaatccc tagcaggttg cgcccgaac agggacttga agaagactga gaagccttgg    900
aacacggctg agtgaaggca gtaagggcgg caggaacaaa ccacgacgga gtgctcctag   960
aaaagcgcag gccgaggtac caagggcggc gtgtggagcg ggagtgaaag aggcctccgg  1020
gtgatatcag tgcctacacc aaatacagta gccagaaggg cttgttatcc tacctttaga  1080
cgggtagaag attgtgggag atgccatggt agggcgcgag aaactccgtc ttgagaggga  1140
aaaaagcaga cgaattagaa aagattaggt tacggcccgg cggaaagaaa aaatataggc  1200
taaaacatat tgtgtgggca gcgaatgaat tggacagatt cggattggca gagagcctgt  1260
tggagtcaaa agagggttgc caaaaaattc ttacagtttt agatccatta gtaccgacag  1320
ggtcagaaaa tttaaaaagc cttttaata ctgtctgcgt catttggtgt atacacgcag   1380
aagagaaagc gaaagatact gaagaagcaa acaaaaggt acagagacat ctagtggcag   1440
aaacaaaaac tacagaaaaa atgccaagta caagtagacc aacagcacca cctagcggga  1500
acggaggact cgaatgcatg gtgaccgcgg ccgcaagagg tgtattcgtg ctagggttct  1560
taggttttct cacgacagca ggagctgcaa tgggcgcggc gtccttgacg ctgtcggctc  1620
agtctcggac tttattggcc gggatagtgc agcaacagca acagctgttg gacgtggtca  1680
```

```
agagacaaca agaaatgttg cgactgaccg tctggggaac aaaaaatctc caggcaagag   1740
tcactgctat cgagaaatac ttaaaggacc aggcgcaact aaattcatgg ggatgtgcgt   1800
ctagacaagt ctgccacact actgtaccat gggtagcggc cgctcgcgag cgactcgagt   1860
atccatggag agccccagca aaggggagaa aaggctcgta caagcaacaa aatatggatg   1920
atgtagattc agatgatgat gacctagtag gggtccctgt cacaccaaga gtaccattaa   1980
gagaaatgac atataggttg gcaagagata tgtcacattt gataaaagaa aaggggggac   2040
tggaagggct gtattacagt gataggagac gtagagtcct agacatatac ttagaaaagg   2100
aagagggaat aattggagac tggcagaact atactcatgg accaggagta aggtatccaa   2160
agttctttgg gtggttatgg aagctagtac cagtagatgt cccacaagag ggagatgaca   2220
gtgagactca ctgcttagtg catccagcac aaacaagcag gtttgatgac cgcatggag   2280 aaacattagt ttggaggttt gaccccacgc tagcttttag ctacgaggcc tttattcgat   2340
acccagagga gtttgggtac aagtcaggcc tgccagagga tgaatggaag caagactga   2400 aagcaagagg gataccgttt agctaaaaac aggaacagct atacttggtc agggcaggaa   2460
gtaactaaca gaaaacagct gagactgcag ggactttcca gaaggggctg ttaccagggg   2520
agggacatgg gaggagccgg tggggaacgc cctcatactt tctgtataaa tgtacccgct   2580
actcgcattg tattcagtcg ctctgcggag aggctggcag attgagccct gggaggttct   2640
ctccagcact agcaggtaga gcctgggtgt tccctgctag actctcacca gtgcttggcc   2700
ggcactgggc agacggctcc acgcttgctt gcttaaaaga cctcttaata aagctgccag   2760
ttagaagca                                                           2769

<210> SEQ ID NO 15
<211> LENGTH: 1411
<212> TYPE: DNA
<213> ORGANISM: Artificial Sequence
<220> FEATURE:
<223> OTHER INFORMATION: Description of Artificial Sequence: IRES and
      neomycin sequences

<400> SEQUENCE: 15
tctagaggaa ttccgcccct ctccctcccc cccccctaac gttactggcc gaagccgctt     60
ggaataaggc cggtgtgcgt ttgtctatat gttattttcc accatattgc cgtcttttgg    120
caatgtgagg gcccggaaac ctggccctgt cttcttgacg agcattccta ggggtctttc    180
ccctctcgcc aaaggaatgc aaggtctgtt gaatgtcgtg aaggaagcag ttcctctgga    240
agcttcttga agacaaacaa cgtctgtagc gaccctttgc aggcagcgga acccccacc    300 tggcgacagg tgcctctgcg gccaaaagcc acgtgtataa gatacacctg caaaggcggc    360
acaaccccag tgccacgttg tgagttggat agttgtggaa agagtcaaat ggctctcctc    420
aagcgtattc aacaagggc tgaaggatgc ccagaaggta cccccattgta tgggatctga    480 tctgggccct cggtgcacat gctttacatg tgtttagtcg aggttaaaaa acgtctaggc    540
cccccgaacc acgggacgt ggttttcctt tgaaaaacac gatgataagc ttgccacaac    600
catggctgaa caagatggat tgcacgcagg ttctccggcc gcttgggtgg agaggctatt    660
cggctatgac tgggcacaac agacaatcgg ctgctctgat gccgccgtgt tccggctgtc    720
agcgcagggg cgcccggttc ttttttgtcaa gaccgacctg tccggtgccc tgaatgaact    780
gcaggacgag gcagcgcggc tatcgtggct ggccacgacg ggcgttcctt gcgcagctgt    840
gctcgacgtt gtcactgaag cgggaaggga ctggctgcta ttgggcgaag tgccggggca    900
```

-continued

```
ggatctcctg tcatctcacc ttgctcctgc cgagaaagta tccatcatgg ctgatgcaat      960
gcggcggctg catacgcttg atccggctac ctgcccattc gaccaccaag cgaaacatcg     1020
catcgagcga gcacgtactc ggatggaagc cggtcttgtc gatcaggatg atctggacga     1080
agagcatcag gggctcgcgc cagccgaact gttcgccagg ctcaaggcgc gcatgcccga     1140
cggcgaggat ctcgtcgtga cccatgcgca tgcctgcttg ccgaatatca tggtggaaaa     1200
tggccgcttt tctggattca tcgactgtgg ccggctgggt gtggcggacc gctatcagga     1260
catagcgttg gctacccgtg atattgctga agagcttggc ggcgaatggg ctgaccgctt     1320
cctcgtgctt tacggtatcg ccgctcccga ttcgcagcgc atcgccttct atcgccttct     1380
tgacgagttc ttctgagcgg gatcggctag c                                    1411
```

<210> SEQ ID NO 16
<211> LENGTH: 548
<212> TYPE: DNA
<213> ORGANISM: Artificial Sequence
<220> FEATURE:
<223> OTHER INFORMATION: Description of Artificial Sequence:
      pSGT-5(SDM/RRE1) 5' LTR

<400> SEQUENCE: 16

```
gttcgctctg cggagaggct ggcagattga gccctgggag gttctctcca gcactagcag       60
tggtcacctg ggtgttccct gctagactct caccagtgct gggcggcac tgggcagacg      120 gctccacgct tgcttgctta aaagacctct aataaagct gccagttaga agcaagttaa       180
gtgtgtgctc ccatctctcc tagtcgccgc ctggtcattc ggtgttcatc taaagtaaca      240
agaccctggt ctgttaggac cctttctgct ttgggaaacc aaggcaggaa aatccctagc      300
aggttggcgc ccgaacaggg acttgaagaa gactgagaag ccttggaaca cggctgagtg      360
aaggcagtaa gggcggcagg aacaaaccac gacggagtgc tcctagaaaa gcgcaggccg      420
aggtaccaag ggcggcgtgt ggagcgggag tgaaagaggc ctccgggtga tatcagtgcc      480
tacaccaaat acagtagcca gaagggcttg ttatcctacc tttagacggg tagaagattg      540
tggagatg                                                               548
```

<210> SEQ ID NO 17
<211> LENGTH: 248
<212> TYPE: DNA
<213> ORGANISM: Artificial Sequence
<220> FEATURE:
<223> OTHER INFORMATION: Description of Artificial Sequence:
      pSGT-5(SDM/RRE1) region containing the
      substitution mutation of the SD

<400> SEQUENCE: 17

```
aggttggcgc ccgaacaggg acttgaagaa gactgagaag ccttggaaca cggctgagtg       60
aaggcagtaa gggcggcagg aacaaaccac gacggagtgc tcctagaaaa gcgcaggccg      120
aggtaccaag ggcggcgtgt ggagcgggag tgaaagaggc ctccgggtga tatcagtgcc      180
tacaccaaat acagtagcca gaagggcttg ttatcctacc tttagacggg tagaagattg      240
tggagatg                                                               248
```

<210> SEQ ID NO 18
<211> LENGTH: 237
<212> TYPE: DNA
<213> ORGANISM: Artificial Sequence
<220> FEATURE:
<223> OTHER INFORMATION: Description of Artificial Sequence:
      pSGT-5(SDX/RRE1) leader region

<400> SEQUENCE: 18

| | | | | | |
|---|---|---|---|---|---|
| aggttggcgc | ccgaacaggg | acttgaagaa | gactgagaag | ccttggaaca | cggctgagtg | 60 |
| aaggcagtaa | gggcggcagg | aacaaaccac | gacggagtgc | tcctagaaaa | gcgcaggccg | 120 |
| aggtaccaag | ggcggcgtgt | ggagcgggag | tgaaagaggc | ctccgggcct | acaccaaata | 180 |
| cagtagccag | aagggcttgt | tatcctacct | ttagacgggt | agaagattgt | ggagatg | 237 |

<210> SEQ ID NO 19
<211> LENGTH: 300
<212> TYPE: DNA
<213> ORGANISM: Human immunodeficiency virus type 2

<400> SEQUENCE: 19

| | | | | | |
|---|---|---|---|---|---|
| agaggtgtat | tcgtgctagg | gttcttaggt | tttctcacga | cagcaggagc | tgcaatgggc | 60 |
| gcggcgtcct | tgacgctgtc | ggctcagtct | cggactttat | tggccgggat | agtgcagcaa | 120 |
| cagcaacagc | tgttggacgt | ggtcaagaga | caacaagaaa | tgttgcgact | gaccgtctgg | 180 |
| ggaacaaaaa | atctccaggc | aagagtcact | gctatcgaga | aatacttaaa | ggaccaggcg | 240 |
| caactaaatt | catggggatg | tgcgtttaga | caagtctgcc | acactactgt | accatgggta | 300 |

<210> SEQ ID NO 20
<211> LENGTH: 2769
<212> TYPE: DNA
<213> ORGANISM: Artificial Sequence
<220> FEATURE:
<223> OTHER INFORMATION: Description of Artificial Sequence: pSGT-5
(RRE1)

<400> SEQUENCE: 20

| | | | | | |
|---|---|---|---|---|---|
| ggaagggctg | tattacagtg | ataggagacg | tagagtccta | gacatatact | tagaaaagga | 60 |
| agagggaata | attggagact | ggcagaacta | tactcatgga | ccaggagtaa | ggtatccaaa | 120 |
| gttctttggg | tggttatgga | agctagtacc | agtagatgtc | ccacaagagg | gagatgacag | 180 |
| tgagactcac | tgcttagtgc | atccagcaca | acaagcagg | tttgatgacc | cgcatggaga | 240 |
| aacattagtt | tggaggtttg | accccacgct | agcttttagc | tacgaggcct | ttattcgata | 300 |
| cccagaggag | tttgggtaca | agtcaggcct | gccagaggat | gaatggaagg | caagactgaa | 360 |
| agcaagaggg | ataccgttta | gctaaaaaca | ggaacagcta | tacttggtca | gggcaggaag | 420 |
| taactaacag | aaaacagctg | agactgcagg | gactttccag | aagggctgt | taccagggga | 480 |
| gggacatggg | aggagccggt | ggggaacgcc | tcatactttt | ctgtataaat | gtacccgcta | 540 |
| ctcgcattgt | attcagtcgc | tctgcggaga | ggctggcaga | ttgagccctg | ggaggttctc | 600 |
| tccagcacta | gcaggtagag | cctgggtgtt | ccctgctaga | ctctcaccag | tgcttggccg | 660 |
| gcactgggca | gacggctcca | cgcttgcttg | cttaaaagac | ctcttaataa | agctgccagt | 720 |
| tagaagcaag | ttaagtgtgt | gctcccatct | ctcctagtcg | ccgcctggtc | attcggtgtt | 780 |
| catctaaagt | aacaagaccc | tggtctgtta | ggacccttc | tgctttggga | accaaggca | 840 |
| ggaaaatccc | tagcaggttg | gcgcccgaac | agggacttga | agaagactga | gaagccttgg | 900 |
| aacacggctg | agtgaaggca | gtaagggcgg | caggaacaaa | ccacgacgga | gtgctcctag | 960 |
| aaaagcgcag | gccgaggtac | aagggcggc | gtgtggagcg | ggagtgaaag | aggcctccgg | 1020 |
| gtgaagtaag | tgcctacacc | aaatacagta | gccagaaggg | cttgttatcc | tacctttaga | 1080 |
| cgggtagaag | attgtgggag | atgccatggt | agggcgcgca | aaactccgtc | ttgagaggga | 1140 |
| aaaagcaga | cgaattagaa | aagattaggt | tacggcccgg | cggaaagaaa | aaatataggc | 1200 |

-continued

```
taaaacatat tgtgtgggca gcgaatgaat tggacagatt cggattggca gagagcctgt      1260
tggagtcaaa agagggttgc caaaaaattc ttacagtttt agatccatta gtaccgacag      1320
ggtcagaaaa tttaaaaagc ctttttaata ctgtctgcgt catttggtgt atacacgcag      1380
aagagaaagc gaaagatact gaagaagcaa acaaaaggt acagagacat ctagtggcag       1440
aaacaaaaac tacagaaaaa atgccaagta caagtagacc aacagcacca cctagcggga      1500
acggaggact cgaatgcatg gtgaccgcgg ccgcaagagg tgtattcgtg ctagggttct      1560
taggttttct cacgacagca ggagctgcaa tgggcgcggc gtccttgacg ctgtcggctc      1620
agtctcggac tttattggcc gggatagtgc agcaacagca acagctgttg gacgtggtca      1680
agagacaaca agaaatgttg cgactgaccg tctgggggaac aaaaaatctc caggcaagag     1740
tcactgctat cgagaaatac ttaaaggacc aggcgcaact aaattcatgg ggatgtgcgt      1800
ctagacaagt ctgccacact actgtaccat gggtagcggc cgctcgcgag cgactcgagt      1860
atccatggag agcccagca gaaggggaga aaggctcgta caagcaacaa aatatggatg       1920
atgtagattc agatgatgat gacctagtag gggtccctgt cacaccaaga gtaccattaa      1980
gagaaatgac atataggttg gcaagagata tgtcacattt gataaaagaa aagggggac      2040 tggaagggct gtattacagt gataggagac gtagagtcct agacatatac ttagaaaagg     2100
aagagggaat aattgagac tggcagaact atactcatgg accaggagta aggtatccaa       2160
agttctttgg gtggttatgg aagctagtac cagtagatgt cccacaagag ggagatgaca     2220
gtgagactca ctgcttagtg catccagcac aaacaagcag gtttgatgac ccgcatggag     2280
aaacattagt ttggaggttt gaccccacgc tagcttttag ctacgaggcc tttattcgat     2340
acccagagga gtttgggtac aagtcaggcc tgccagagga tgaatggaag caagactga      2400 aagcaagagg gataccgttt agctaaaaac aggaacagct atacttggtc agggcaggaa     2460
gtaactaaca gaaacagct gagactgcag ggactttcca gaaggggctg ttaccagggg     2520
agggacatgg gaggagccgg tggggaacgc cctcatactt tctgtataaa tgtacccgct     2580
actcgcattg tattcagtcg ctctgcggag aggctggcag attgagccct ggaggttct     2640 ctccagcact agcaggtaga gcctgggtgt tccctgctag actctcacca gtgcttggcc     2700
ggcactgggc agacggctcc acgcttgctt gcttaaaaga cctcttaata aagctgccag     2760
ttagaagca                                                              2769
```

<210> SEQ ID NO 21
<211> LENGTH: 9726
<212> TYPE: DNA
<213> ORGANISM: Artificial Sequence
<220> FEATURE:
<223> OTHER INFORMATION: Description of Artificial Sequence: pROD
      (SD36/EM)
<220> FEATURE:
<221> NAME/KEY: misc_feature
<222> LOCATION: (1)..(9726)
<223> OTHER INFORMATION: n represents a, c, t, or g.

<400> SEQUENCE: 21

```
ggtcgctctg cggagaggct ggcagattga gccctgggag gttctctcca gcactagcag       60
gtagagcctg ggtgttccct gctagactct caccagcact tggccggtgc tgggcagacg      120
gccccacgct tgcttgctta aaaacctctt aataaagctg ccagttagaa gcaagttaag      180
tgtgtgctcc catctctcct agtcgccgcc tggtcattcg gtgttcacct gagtaacaag      240
accctggtct gttaggaccc ttcttgcttt gggaaaccga ggcaggaaaa tccctagcag      300
```

```
gttggcgnnn nnnnnnnnnn nnnnnnnnnn nnnnnnnnnn nnnnnnnnnn nnnnnnnnnn    360
nnnnnnnnnn nnnnnnnnnn nnnnnnnnnn nnnnnnnnnn nnnnnnnnnn nnnnnnnnnn    420
nnnnnnnnnn nnnnnnnnnn nnnnnnnnnn nnnnnnnnnn nnnggtgaag gtaagtacct    480
agggtaaccc gcgcnnnnnn nnnnnnnnnn nnnnnnnnnn nnnnnnnnnn nnnnnnnngt    540
gggagatggg cgcgagaaac tccgtcttga gagggaaaaa agcagatgaa ttagaaagaa    600
tcaggttacg gcccggcgga agaaaaagt acaggctaaa acatattgtg tgggcagcga    660
ataaattgga cagattcgga ttagcagaga gcctgttgga gtcaaaagag ggttgtcaaa    720
aaattcttac agttttagat ccaatggtac cgacaggttc agaaaattta aaaagtcttt    780
ttaatactgt ctgcgtcatt tggtgcatac acgcagaaga gaaagtgaaa gatactgaag    840
gagcaaaaca aatagtgcgg agacatctag tggcagaaac aggaactgca gagaaaatgc    900
caagcacaag tagaccaaca gcaccatcta gcgagaaggg aggaaattac ccagtgcaac    960
atgtaggcgg caactacacc catataccgc tgagtcccg aaccctaaat gcctgggtaa   1020
aattagtaga ggaaaaaaag ttcggggcag aagtagtgcc aggatttcag gcactctcag   1080
aaggctgcac gccctatgat atcaaccaaa tgcttaattg tgtgggcgac catcaagcag   1140
ccatgcagat aatcagggag attatcaatg aggaagcagc agaatgggat gtgcaacatc   1200
caataccagg cccccttacca gcggggcagc ttagagagcc aaggggatct gacatagcag   1260
ggacaacaag cacagtagaa gaacagatcc agtggatgtt taggccacaa aatcctgtac   1320
cagtaggaaa catctataga agatggatcc agataggatt gcagaagtgt gtcaggatgt   1380
acaacccgac caacatccta gacataaaac agggaccaaa ggagccgttc caaagctatg   1440
tagatagatt ctacaaaagc ttgagggcag aacaaacaga tccagcagtg aagaattgga   1500
tgacccaaac actgctagta caaaatgcca acccagactg taaattagtg ctaaaaggac   1560
tagggatgaa ccctacctta gaagagatgc tgaccgcctg tcaggggta ggtgggccag   1620 gccagaaagc tagattaatg gcagaggccc tgaaagaggt cataggacct gcccctatcc   1680
cattcgcagc agcccagcag agaaaggcat ttaaatgctg gaactgtgga aggaagggc   1740 actcggcaag acaatgccga gcacctagaa ggcagggctg ctggaagtgt ggtaagccag   1800
gacacatcat gacaaactgc ccagatagac aggcaggttt tttaggactg gcccttgggg   1860
gaaagaagcc ccgcaacttc cccgtggccc aagttccgca ggggctgaca ccaacagcac   1920
ccccagtgga tccagcagtg gatctactgg agaaatatat gcagcaaggg aaaagacaga   1980
gagagcagag agagagacca tacaaggaag tgacagagga cttactgcac ctcgagcagg   2040
gggagacacc atacagggag ccaccaacag aggacttgct gcacctcaat tctctctttg   2100
gaaaagacca gtagtcacag catacattga gggtcagcca gtagaagtct tgttagacac   2160
aggggctgac gactcaatag tagcaggaat agagttaggg aacaattata gcccaaaaat   2220
agtaggggga atagggggat tcataaatac caaggaatat aaaaatgtag aaatagaagt   2280
tctaaataaa aaggtacggg ccaccataat gacaggcgac accccaatca acattttttgg   2340 cagaaatatt ctgacagcct taggcatgtc attaaatcta ccagtcgcca agtagagcc   2400 aataaaaata atgctaaagc cagggaaaga tggaccaaaa ctgagacaat ggcccttaac   2460
aaaagaaaaa atagaagcac taaaagaaat ctgtgaaaaa atggaaaag aaggccagct   2520 agaggaagca cctccaacta atccttataa taccccaca tttgcaatca agaaaaagga   2580 caaaacaaa tggaggatgc taatagattt cagagaacta acaaggtaa ctcaagattt   2640 cacagaaatt cagttaggaa ttccacaccc agcagggttg gccaagaaga gaagaattac   2700
```

```
tgtactagat gtaggggatg cttacttttc cataccacta catgaggact ttagaccata    2760
tactgcattt actctaccat cagtgaacaa tgcagaacca ggaaaaagat acatatataa    2820
agtcttgcca cagggatgga agggatcacc agcaattttt caacacacaa tgagacaggt    2880
attagaacca ttcagaaaag caaacaagga tgtcattatc attcagtaca tggatgatat    2940
cttaatagct agtgacagga cagatttaga acatgatagg gtagtcctgc agctcaagga    3000
acttctaaat ggcctaggat tttctacccc agatgagaag ttccaaaaag accctccata    3060
ccactggatg ggctatgaac tatggccaac taaatggaag ttgcagaaaa tacagttgcc    3120
ccaaaaagaa atatggacag tcaatgacat ccagaagcta gtgggtgtcc taaattgggc    3180
agcacaactc tacccaggga taaagaccaa acacttatgt aggttaatca gaggaaaaat    3240
gacactcaca gaagaagtac agtggacaga attagcagaa gcagagctag aagaaaacag    3300
aattatccta agccaggaac aagagggaca ctattaccaa gaagaaaaag agctagaagc    3360
aacagtccaa aaggatcaag agaatcagtg gacatataaa atacaccagg aagaaaaaat    3420
tctaaaagta ggaaaatatg caaaggtgaa aaacacccat accaatggaa tcagattgtt    3480
agcacaggta gttcagaaaa taggaaaaga agcactagtc atttggggac gaataccaaa    3540
atttcaccta ccagtagaga gagaaatctg ggagcagtgg tgggataact actggcaagt    3600
gacatggatc ccagactggg acttcgtgtc taccccacca ctggtcaggt tagcgtttaa    3660
cctggtaggg gatcctatac caggtgcaga gaccttctac acagatggat cctgcaatag    3720
gcaatcaaaa gaaggaaaag caggatatgt aacagataga gggaaagaca aggtaaagaa    3780
actagagcaa actaccaatc agcaagcaga actagaagcc tttgcgatgg cactaacaga    3840
ctcgggtcca aaagttaata ttatagtaga ctcacagtat gtaatgggga tcagtgcaag    3900
ccaaccaaca gagtcagaaa gtaaaatagt gaaccagatc ataagagaaa tgataaaaaa    3960
ggaagcaatc tatgttgcat gggtcccagc ccacaaaggc ataggggaa ccaggaagt     4020 agatcattta gtgagtcagg gtatcagaca agtgttgttc ctggaaaaaa tagagcccgc    4080
tcaggaagaa catgaaaaat atcatagcaa tgtaaaagaa ctgtctcata aatttggaat    4140
acccaattta gtggcaaggc aaatagtaaa ctcatgtgcc caatgtcaac agaaagggga    4200
agctatacat gggcaagtaa atgcagaact aggcacttgg caaatggact gcacacattt    4260
agaaggaaag atcattatag tagcagtaca tgttgcaagt ggatttatag aagcagaagt    4320
catcccacag gaatcaggaa gacaaacagc actcttccta ttgaaactgg caagtaggtg    4380
gccaataaca cacttgcata cagataatgg tgccaacttc acttcacagg aggtgaagat    4440
ggtagcatgg tggataggta tagaacaatc ctttggagta ccttacaatc cacagagcca    4500
aggagtagta gaagcaatga atcaccatct aaaaaaccaa ataagtagaa tcagagaaca    4560
ggcaaataca atagaaacaa tagtactaat ggcaattcat tgcatgaatt ttaaaagaag    4620
ggggggaata gggatatga ctccatcaga aagattaatc aatatgatca ccacagaaca    4680
agagatacaa ttcctccaag ccaaaaattc aaaattaaaa gattttcggg tctatttcag    4740
agaaggcaga gatcagttgt ggaaaggacc tggggaacta ctgtggaaag gagaaggagc    4800
agtcctagtc aagtaggaa cagacataaa aataatacca agaaggaaag ccaagatcat    4860
cagagactat ggaggaagac aagagatgga tagtggttcc cacctggagg gtgccaggga    4920
ggatggagaa atggcatagc cttgtcaagt atctaaaata caaaacaaag gatctagaaa    4980
aggtgtgcta tgttccccac cataaggtgg gatgggcatg gtggacttgc agcagggtaa    5040 tattccccatt aaaaggaaac agtcatctag agatacaggc atattggaac ttaacaccag    5100
```

```
aaaaaggatg gctctcctct tattcagtaa gaataacttg gtacacagaa aagttctgga    5160
cagatgttac cccagactgt gcagatgtcc taatacatag cacttatttc ccttgcttta    5220
cagcaggtga agtaagaaga gccatcagag gggaaaagtt attgtcctgc tgcaattatc    5280
cccgagctca tagagcccag gtaccgtcac ttcaatttct ggccttagtg gtagtgcaac    5340
aaaatgacag accccagaga gacagtacca ccaggaaaca gcggcgaaga gactatcgga    5400
gaggccttcg cctggctaaa caggacagta gaagccataa acagagaagc agtgaatcac    5460
ctaccccgag aacttatttt ccaggtgtgg cagaggtcct ggagatactg gcatgatgaa    5520
caagggatgt cagaaagtta cacaaagtat agatatttgt gcataataca gaaagcagtg    5580
tacatgcatg ttaggaaagg gtgtacttgc ctggggaggg gacatgggcc aggagggtgg    5640
agaccagggc ctcctcctcc tcccctccca ggtctggtct aatggctgaa gcaccaacag    5700
agctcccccc ggtggatggg accccactga gggagccagg ggatgagtgg ataatagaaa    5760
tcttgagaga aataaaagaa gaagctttaa agcattttga ccctcgcttg ctaattgctc    5820
ttggcaaata tatctatact agacatggag acacccttga aggcgccaga gagctcatta    5880
aagtcctgca acgagccctt ttcacgcact tcagagcagg atgtggccac tcaagaattg    5940
gccagacaag gggaggaaat cctctctcag ctataccgac ccctagaaac atgcaataac    6000
tcatgctatt gtaagcgatg ctgctaccat tgtcagatgt gttttctaaa caggggctc    6060 gggatatgtt atgaacgaaa gggcagacga agaaggactc caaagaaaac taagactcat    6120
ccgtctccta caccagacaa gtgagtatga tgaatcagct gcttattgcc attttattag    6180
ctagtgcttg cttagtatat tgcacccaat atgtaactgt tttctatggc gtacccacgt    6240
ggaaaaatgc aaccattccc ctcttttgtg caaccagaaa tagggatact tggggaacca    6300
tacagtgctt gcctgacaat gatgattatc aggaaataac tttgaatgta acagaggctt    6360
ttgatgcatg gnntagcgtg agatcttagt gcataggtag cgtgagatgt tagtgactaa    6420
gatcggaata atacagtaac agaacaagca atagaagatg tctggcatct attcgagaca    6480
tcaataaaac catgtgtcaa actaacacct ttatgtgtag caatgaaatg cagcagcaca    6540
gagagcagca cagggaacaa cacaacctca aagagcacaa gcacaaccac aaccacaccc    6600
acagaccagg agcaagagat aagtgaggat actccatgcg cacgcgcaga caactgctca    6660
ggattgggag aggaagaaac gatcaattgc cagttcaata tgacaggatt agaaagagat    6720
aagaaaaaac agtataatga acatggtac tcaaaagatg tggtttgtga gacaaataat    6780
agcacaaatc agacccagtg ttacatgaac cattgcaaca catcagtcat cacagaatca    6840
tgtgacaagc actattggga tgctataagg tttagatact gtgcaccacc gggttatgcc    6900
ctattaagat gtaatgatac caattattca ggctttgcac ccaactgttc taagtagta    6960 gcttctacat gcaccaggat gatggaaacg caaacttcca catggtttgg ctttaatggc    7020
actagagcag agaatagaac atatatctat tggcatggca gagataatag aactatcatc    7080
agcttaaaca aatattataa tctcagtttg cattgtaaga ggccagggaa taagatagtg    7140
aaacaaataa tgcttatgtc aggacatgtg tttcactccc actaccagcc gatcaataaa    7200
agacccagac aagcatggtg ctggttcaaa ggcaaatgga aagacgccat gcaggaggtg    7260
aaggaaaccc ttgcaaaaca tcccaggtat agaggaacca atgacacaag gaatattagc    7320
tttgcagcgc caggaaaagg ctcagaccca gaagtagcat acatgtggac taactgcaga    7380
ggagagtttc tctactgcaa catgacttgg ttcctcaatt ggatagagaa taagacacac    7440
cgcaattatg caccgtgcca tataaagcaa ataattaaca catggcataa ggtagggaga    7500
```

```
aatgtatatt tgcctcccag ggaaggggag ctgtcctgca actcaacagt aaccagcata    7560
attgctaaca ttgactggca aaacaataat cagacaaaca ttacctttag tgcagaggtg    7620
gcagaactat acagattgga gttgggagat tataaattgg tagaaataac accaattggc    7680
ttcgcaccta caaaagaaaa aagatactcc tctgctcacg ggagacatac aagaggtgtg    7740
ttcgtgctag ggttcttggg ttttctcgca acagcaggtt ctgcaatggg cgcggcgtcc    7800
ctgaccgtgt cggctcagtc ccggacttta ctggccggga tagtgcagca acagcaacag    7860
ctgttggacg tggtcaagag acaacaagaa ctgttgcgac tgaccgtctg gggaacgaaa    7920
aacctccagg caagagtcac tgctatagag aagtacctac aggaccaggc gcggctaaat    7980
tcatggggat gtgcgtttag acaagtctgc cacactactg taccatgggt taatgattcc    8040
ttagcacctg actgggacaa tatgacgtgg caggaatggg aaaaacaagt ccgctacctg    8100
gaggcaaata tcagtaaaag tttagaacag gcacaaattc agcaagagaa aaatatgtat    8160
gaactacaaa aattaaatag ctgggatatt tttggcaatt ggtttgactt aacctcctgg    8220
gtcaagtata ttcaatatgg agtgcttata atagtagcag taatagcttt aagaatagtg    8280
atatatgtag tacaaatgtt aagtaggctt agaaagggct ataggcctgt tttctcttcc    8340
ccccccggtt atatccaaca gatccatatc cacaaggacc ggggacagcc agccaacgaa    8400
gaaacagaag aagacggtgg aagcaacggt ggagacagat actggccctg ccgatagca    8460 tatatacatt tcctgatccg ccagctgatt cgcctcttga ccagactata cagcatctgc    8520
agggacttac tatccaggag cttcctgacc ctccaactca tctaccagac agtcagagac    8580
tggctgagac ttagaacagc cttcttgcaa tatgggtgcg agtggatcca agaagcattc    8640
caggccgccg cgagggctac aagagagact cttgcgggcg cgtgcagggg cttgtggagg    8700
gtattggaac gaatcgggag ggaatactc gcggttccaa gaaggatcag acagggagca    8760
gaaatcgccc tcctgtgagg gacggcagta tcagcaggga gactttatga atactccatg    8820
gaaggaccca gcagcagaaa gggagaaaaa tttgtacagg caacaaaata tggatgatgt    8880
agattcagat gatgatgacc aagtaagagt ttctgtcaca ccaaaagtac cactaagacc    8940
aatgacacat agattggcaa tagatatgtc acatttaata aaaacaaggg ggggactgga    9000
agggatgttt tacagtgaaa gaagacataa atcttaaat atatacttag aaaaggaaga    9060
agggataatt gcagattggc agaactacac tcatgggcca ggagtaagat acccaatgtt    9120
ctttgggtgg ctatggaagc tagtaccagt agatgtccca caagaagggg aggacactga    9180
gactcactgc ttagtacatc cagcacaaac aagcaagttt gatgacccgc atggggagac    9240
actagtctgg gagtttgatc ccttgctggc ttatagttac gaggcttta ttcggtaccc    9300 agaggaattt gggcacaagt caggcctgcc agaggaagag tggaaggcga gactgaaagc    9360
aagaggaata ccatttagtt aaagacagga acagctatac ttggtcaggg caggaagtaa    9420
ctaacagaaa cagctgagac tgcagggact ttccagaagg ggctgtaacc aagggaggga    9480
catgggagga gctggtgggg aacgccctca tattctctgt ataaatatac ccgctagctt    9540
gcattgtact tcggtcgctc tgcggagagg ctggcagatt gagccctggg aggttctctc    9600
cagcagtagc aggtagagcc tgggtgttcc ctgctagact ctcaccagca cttggccggt    9660
gctgggcaga cggccccacg cttgcttgct taaaaacctc cttaataaag ctgccagtta    9720
gaagca                                                              9726
```

-continued

```
<210> SEQ ID NO 22
<211> LENGTH: 9663
<212> TYPE: DNA
<213> ORGANISM: Artificial Sequence
<220> FEATURE:
<223> OTHER INFORMATION: Description of Artificial Sequence:
      pCM-ROD(SD36/EM)
<220> FEATURE:
<221> NAME/KEY: misc_feature
<222> LOCATION: (1)..(9663)
<223> OTHER INFORMATION: n represents a, c, g or t.

<400> SEQUENCE: 22
tcaatattgg ccattagcca tattattcat tggttatata gcataaatca atattggcta      60
ttggccattg catacgttgt atctatatca taatatgtac atttatattg gctcatgtcc     120
aatatgaccg ccatgttggc attgattatt gactagttat taatagtaat caattacggg     180
gtcattagtt catagcccat atatggagtt ccgcgttaca taacttacgg taaatggccc     240
gcctggctga ccgcccaacg accccgccc attgacgtca ataatgacgt atgttcccat      300
agtaacgcca atagggactt tccattgacg tcaatgggtg gagtatttac ggtaaactgc     360
ccacttggca gtacatcaag tgtatcatat gccaagtccg cccctattg acgtcaatga      420 cggtaaatgg cccgcctggc attatgccca gtacatgacc ttacgggact tcctacttg      480 gcagtacatc tacgtattag tcatcgctat taccatggtg atgcggtttt ggcagtacac     540
caatgggcgt ggatagcggt ttgactcacg gggatttcca gtctccacc ccattgacgt      600 caatgggagt ttgttttggc accaaaatca acgggacttt ccaaaatgtc gtaataaccc     660
cgccccgttg acgcaaatgg gcggtaggcg tgtacggtgg gaggtctata taagcagagc     720
tcgtttagtg aaccgtcaga tcactagaag ctttattgcg gtagtttatc acagttaaat     780
tgctaacgca gtcagtgctt ctgacacaac agtctcgaac ttaagctgca gaagttggtc     840
gtgaggcact gggcaggtaa gtatcaaggt tacaagacag gtttaaggag accaatagaa     900
actgggcttg tcgagacaga agactctt gcgtttctga taggcaccta ttggtcttac       960
tgacatccac tttgccttc tctccacagg tgtccactcc cagttcaatt acagctctta      1020
aggctagagt acttaatacg actcactata ggctagcctc gaggccgggt gaaggtaagt     1080
acctagggta acccgcgcnn nnnnnnnnnn nnnnnnnnnn nnnnnnnnnn nnnnnnnnnn     1140
nngtgggaga tgggcgcgag aaactccgtc ttgagaggga aaaagcaga tgaattagaa      1200 agaatcaggt tacggcccgg cggaaagaaa aagtacaggc taaaacatat tgtgtgggca     1260
gcgaataaat tggacagatt cggattagca gagagcctgt tggagtcaaa agagggttgt     1320
caaaaaattc ttacagtttt agatccaatg gtaccgacag gttcagaaaa tttaaaaagt     1380 cttttttaata ctgtctgcgt catttggtgc atacacgcag aagagaaagt gaaagatact    1440
gaaggagcaa acaaatagt gcggagacat ctagtggcag aaacaggaac tgcagagaaa     1500
atgccaagca caagtagacc aacagcacca tctagcgaga agggaggaaa ttacccagtg     1560
caacatgtag gcggcaacta cacccatata ccgctgagtc cccgaaccct aaatgcctgg     1620
gtaaaattag tagaggaaaa aaagttcggg gcagaagtag tgccaggatt tcaggcactc     1680
tcagaaggct gcacgcccta tgatatcaac caaatgctta ttgtgtggg cgaccatcaa      1740 gcagccatgc agataatcag ggagattatc aatgaggaag cagcagaatg ggatgtgcaa     1800
catccaatac caggcccctt accagcgggg cagcttagag agccaagggg atctgacata     1860
gcagggacaa caagcacagt agaagaacag atccagtgga tgtttaggcc acaaaatcct     1920
gtaccagtag gaaacatcta tagaagatgg atccagtag gattgcagaa gtgtgtcagg     1980
```

```
atgtacaacc cgaccaacat cctagacata aaacagggac caaaggagcc gttccaaagc    2040
tatgtagata gattctacaa aagcttgagg gcagaacaaa cagatccagc agtgaagaat    2100
tggatgaccc aaacactgct agtacaaaat gccaacccag actgtaaatt agtgctaaaa    2160
ggactaggga tgaaccctac cttagaagag atgctgaccg cctgtcaggg ggtaggtggg    2220
ccaggccaga aagctagatt aatggcagag gccctgaaag aggtcatagg acctgcccct    2280
atcccattcg cagcagccca gcagagaaag gcatttaaat gctggaactg tggaaaggaa    2340
gggcactcgg caagacaatg ccgagcacct agaaggcagg gctgctggaa gtgtggtaag    2400
ccaggacaca tcatgacaaa ctgcccagat agacaggcag gttttttagg actgggccct    2460
tggggaaaga agccccgcaa cttccccgtg gcccaagttc cgcagggggct gacaccaaca    2520 gcacccccag tggatccagc agtggatcta ctggagaaat atatgcagca agggaaaaga    2580
cagagagagc agagagagag accatacaag gaagtgacag aggacttact gcacctcgag    2640 caggggggaga caccatacag ggagccacca acagaggact tgctgcacct caattctctc    2700
tttggaaaag accagtagtc acagcataca ttgagggtca gccagtagaa gtcttgttag    2760 acacagggggc tgacgactca atagtagcag gaatagagtt agggaacaat tatagcccaa    2820
aaatagtagg gggaataggg ggattcataa ataccaagga atataaaaat gtagaaatag    2880
aagttctaaa taaaaggta cgggccacca taatgacagg cgacacccca atcaacattt    2940
ttggcagaaa tattctgaca gccttaggca tgtcattaaa tctaccagtc gccaaagtag    3000
agccaataaa ataatgcta aagccaggga aagatggacc aaaactgaga caatggccct    3060
taacaaaaga aaaaatagaa gcactaaaag aaatctgtga aaaaatggaa aaagaaggcc    3120
agctagagga agcacctcca actaatcctt ataatacccc cacatttgca atcaagaaaa    3180
aggacaaaaa caaatggagg atgctaatag atttcagaga actaaacaag gtaactcaag    3240
atttcacaga aattcagtta ggaattccac acccagcagg gttggccaag aagagaagaa    3300
ttactgtact agatgtaggg gatgcttact tttccatacc actacatgag gactttagac    3360
catatactgc atttactcta ccatcagtga acaatgcaga accaggaaaa agatacatat    3420
ataaagtctt gccacaggga tggaagggat caccagcaat ttttcaacac acaatgagac    3480
aggtattaga accattcaga aaagcaaaca aggatgtcat tatcattcag tacatggatg    3540
atatcttaat agctagtgac aggacagatt tagaacatga tagggtagtc ctgcagctca    3600
aggaacttct aaatggccta ggattttcta ccccagatga gaagttccaa aaagaccctc    3660
cataccactg gatgggctat gaactatggc caactaaatg gaagttgcag aaaatacagt    3720
tgccccaaaa agaaatatgg acagtcaatg acatccagaa gctagtgggt gtcctaaatt    3780
gggcagcaca actctaccca gggataaaga ccaaacactt atgtaggtta atcagaggaa    3840
aaatgacact cacagaagaa gtacagtgga cagaattagc agaagcagag ctagaagaaa    3900
acagaattat cctaagccag gaacaagagg gacactatta ccaagaagaa aaagagctag    3960
aagcaacagt ccaaaaggat caagagaatc agtggacata taaaatacac caggaagaaa    4020
aaattctaaa agtaggaaaa tatgcaaagg tgaaaaacac ccataccaat ggaatcagat    4080
tgttagcaca ggtagttcag aaaataggaa aagaagcact agtcatttgg ggacgaatac    4140
caaaatttca cctaccagta gagagagaaa tctgggagca gtggtgggat aactactggc    4200
aagtgacatg gatcccagac tgggacttcg tgtctacccc accactggtc aggttagcgt    4260
ttaacctggt agggggatcct ataccaggtg cagagacctt ctacacagat ggatcctgca    4320
ataggcaatc aaaagaagga aaagcaggat atgtaacaga tagagggaaa gacaaggtaa    4380
```

```
agaaactaga gcaaactacc aatcagcaag cagaactaga agcctttgcg atggcactaa    4440
cagactcggg tccaaaagtt aatattatag tagactcaca gtatgtaatg gggatcagtg    4500
caagccaacc aacagagtca gaaagtaaaa tagtgaacca gatcatagaa gaaatgataa    4560
aaaaggaagc aatctatgtt gcatgggtcc cagcccacaa aggcataggg ggaaaccagg    4620
aagtagatca tttagtgagt cagggtatca gacaagtgtt gttcctggaa aaaatagagc    4680
ccgctcagga agaacatgaa aaatatcata gcaatgtaaa agaactgtct cataaatttg    4740
gaatacccaa tttagtggca aggcaaatag taaactcatg tgcccaatgt aacagaaag    4800 gggaagctat acatgggcaa gtaaatgcag aactaggcac ttggcaaatg gactgcacac    4860
atttagaagg aaagatcatt atagtagcag tacatgttgc aagtggattt atagaagcag    4920
aagtcatccc acaggaatca ggaagacaaa cagcactctt cctattgaaa ctggcaagta    4980
ggtggccaat aacacacttg catacagata atggtgccaa cttcacttca caggaggtga    5040
agatggtagc atggtggata ggtatagaac aatcctttgg agtaccttac aatccacaga    5100
gccaaggagt agtagaagca atgaatcacc atctaaaaaa ccaaataagt agaatcagag    5160
aacaggcaaa tacaatagaa acaatagtac taatggcaat tcattgcatg aattttaaaa    5220
gaaggggggg aatagggat atgactccat cagaaagatt aatcaatatg atcaccacag    5280
aacaagagat acaattcctc caagccaaaa attcaaaatt aaaagatttt cgggtctatt    5340
tcagagaagg cagagatcag ttgtggaaag gacctgggga actactgtgg aaaggagaag    5400
gagcagtcct agtcaaggta ggaacagaca taaaaataat accaagaagg aaagccaaga    5460
tcatcagaga ctatggagga agacaagaga tggatagtgg ttcccacctg gagggtgcca    5520
gggaggatgg agaaatggca tagccttgtc aagtatctaa aatacaaaac aaaggatcta    5580
gaaaaggtgt gctatgttcc ccaccataag gtgggatggg catggtggac ttgcagcagg    5640
gtaatattcc cattaaaagg aaacagtcat ctagagatac aggcatattg gaacttaaca    5700
ccagaaaaag gatggctctc ctcttattca gtaagaataa cttggtacac agaaaagttc    5760
tggacagatg ttaccccaga ctgtgcagat gtcctaatac atagcactta tttcccttgc    5820
tttacagcag gtgaagtaag aagagccatc agagggggaaa agttattgtc ctgctgcaat    5880
tatccccgag ctcatagagc ccaggtaccg tcacttcaat ttctggcctt agtggtagtg    5940
caacaaaatg acagaccccca gagagacagt accaccagga aacagcggcg aagagactat    6000
cggagaggcc ttcgcctggc taaacaggac agtagaagcc ataaacagag aagcagtgaa    6060
tcacctaccc cgagaactta ttttccaggt gtggcagagg tcctggagat actggcatga    6120
tgaacaaggg atgtcagaaa gttacacaaa gtatagatat ttgtgcataa tacagaaagc    6180
agtgtacatg catgttagga aagggtgtac ttgcctgggg aggggacatg ggccaggagg    6240
gtggagacca gggcctcctc ctcctccccc tccaggtctg gtctaatggc tgaagcacca    6300
acagagctcc ccccggtgga tgggacccca ctgagggagc caggggatga gtggataata    6360
gaaatcttga gagaaataaa agaagaagct ttaaagcatt ttgaccctcg cttgctaatt    6420
gctcttggca aatatatcta tactagacat ggagacaccc ttgaaggcgc cagagagctc    6480
attaaagtcc tgcaacgagc ccttttcacg cacttcagag caggatgtgg ccactcaaga    6540
attggccaga caagggagg aaatcctctc tcagctatac cgaccccctag aaacatgcaa    6600 taactcatgc tattgtaagc gatgctgcta ccattgtcag atgtgttttc taaacaaggg    6660
gctcgggata tgttatgaac gaaagggcag acgaagaagg actccaaaga aaactaagac    6720
tcatccgtct cctacaccag acaagtgagt atgatgaatc agctgcttat tgccatttta    6780
```

```
ttagctagtg cttgcttagt atattgcacc caatatgtaa ctgttttcta tggcgtaccc    6840
acgtggaaaa atgcaaccat tcccctcttt tgtgcaacca gaaataggga tacttgggga    6900
accatacagt gcttgcctga caatgatgat tatcaggaaa taactttgaa tgtaacagag    6960
gcttttgatg catggnntag cgtgagatct tagtgcatag gtagcgtgag atgttagtga    7020
ctaagatcgg aataatacag taacagaaca agcaatagaa gatgtctggc atctattcga    7080
gacatcaata aaaccatgtg tcaaactaac acctttatgt gtagcaatga aatgcagcag    7140
cacagagagc agcacaggga acaacacaac ctcaaagagc acaagcacaa ccacaaccac    7200
acccacagac caggagcaag agataagtga ggatactcca tgcgcacgcg cagacaactg    7260
ctcaggattg ggagaggaag aaacgatcaa ttgccagttc aatatgacag gattagaaag    7320
agataagaaa aaacagtata atgaaacatg gtactcaaaa gatgtggttt gtgagacaaa    7380
taatagcaca aatcagaccc agtgttacat gaaccattgc aacacatcag tcatcacaga    7440
atcatgtgac aagcactatt gggatgctat aaggtttaga tactgtgcac caccgggtta    7500
tgccctatta agatgtaatg ataccaatta ttcaggcttt gcacccaact gttctaaagt    7560
agtagcttct acatgcacca ggatgatgga aacgcaaact tccacatggt ttggctttaa    7620
tggcactaga gcagagaata gaacatatat ctattggcat ggcagagata atagaactat    7680
catcagctta aacaaatatt ataatctcag tttgcattgt aagaggccag ggaataagat    7740
agtgaaacaa ataatgctta tgtcaggaca tgtgtttcac tcccactacc agccgatcaa    7800
taaaagaccc agacaagcat ggtgctggtt caaaggcaaa tggaaagacg ccatgcagga    7860
ggtgaaggaa acccttgcaa aacatcccag gtatagagga accaatgaca caaggaatat    7920
tagctttgca gcgccaggaa aaggctcaga cccagaagta gcatacatgt ggactaactg    7980
cagaggagag tttctctact gcaacatgac ttggttcctc aattggatag agaataagac    8040
acaccgcaat tatgcaccgt gccatataaa gcaaataatt aacacatggc ataaggtagg    8100
gagaaatgta tatttgcctc ccagggaagg ggagctgtcc tgcaactcaa cagtaaccag    8160
cataattgct aacattgact ggcaaaaaca taatcagaca acattacctt tagtgcaga    8220
ggtggcagaa ctatacagat ggagttggg agattataaa ttggtagaaa taacaccaat    8280
tggcttcgca cctacaaaag aaaaaagata ctcctctgct cacggagac atacaagagg    8340
tgtgttcgtg ctagggttct tgggtttct cgcaacagca ggttctgcaa tgggcgcggc    8400
gtccctgacc gtgtcggctc agtcccggac tttactggcc gggatagtgc agcaacagca    8460
acagctgttg gacgtggtca agagacaaca agaactgttg cgactgaccg tctggggaac    8520
gaaaaacctc caggcaagag tcactgctat agagaagtac ctacaggacc aggcgcggct    8580
aaattcatgg ggatgtgcgt ttagacaagt ctgccacact actgtaccat gggttaatga    8640
ttccttagca cctgactggg acaatatgac gtggcaggaa tgggaaaaac aagtccgcta    8700
cctggaggca aatatcagta aaagtttaga acaggcacaa attcagcaag agaaaaatat    8760
gtatgaacta caaaaattaa atagctggga tatttttggc aattggtttg acttaacctc    8820
ctgggtcaag tatattcaat atggagtgct tataatagta gcagtaatag ctttaagaat    8880
agtgatatat gtagtacaaa tgttaagtag gcttagaaag gctataggc ctgttttctc    8940
ttcccccccc ggttatatcc aacagatcca tatccacaag gaccgggac agccagccaa    9000
cgaagaaaca gaagaagacg gtggaagcaa cggtggagac agatactggc cctggccgat    9060
agcatatata catttcctga tccgccagct gattcgcctc ttgaccagac tatacagcat    9120
ctgcagggac ttactatcca ggagcttcct gaccctccaa ctcatctacc agacagtcag    9180
```

-continued

| | |
|---|---|
| agactggctg agacttagaa cagccttctt gcaatatggg tgcgagtgga tccaagaagc | 9240 |
| attccaggcc gccgcgaggg ctacaagaga gactcttgcg ggcgcgtgca ggggcttgtg | 9300 |
| gagggtattg aacgaatcg ggaggggaat actcgcggtt ccaagaagga tcagacaggg | 9360 |
| agcagaaatc gccctcctgt gagggacggc agtatcagca gggagacttt atgaatactc | 9420 |
| catgggggcg gccgcttcga gcagacatga taagatacat tgatgagttt ggacaaacca | 9480 |
| caactagaat gcagtgaaaa aaatgcttta tttgtgaaat ttgtgatgct attgctttat | 9540 |
| ttgtaaccat tataagctgc aataaacaag ttaacaacaa caattgcatt cattttatgt | 9600 |
| ttcaggttca gggggagatg tgggaggttt tttaaagcaa gtaaacctc tacaaatgtg | 9660 |
| gta | 9663 |

<210> SEQ ID NO 23
<211> LENGTH: 4203
<212> TYPE: DNA
<213> ORGANISM: Artificial Sequence
<220> FEATURE:
<223> OTHER INFORMATION: Description of Artificial Sequence: pCM-ENV
(ROD)

<400> SEQUENCE: 23

| | |
|---|---|
| tcaatattgg ccattagcca tattattcat tggttatata gcataaatca atattggcta | 60 |
| ttggccattg catacgttgt atctatatca taatatgtac atttatattg gctcatgtcc | 120 |
| aatatgaccg ccatgttggc attgattatt gactagttat taatagtaat caattacggg | 180 |
| gtcattagtt catagcccat atatggagtt ccgcgttaca taacttacgg taaatggccc | 240 |
| gcctggctga ccgcccaacg acccccgccc attgacgtca ataatgacgt atgttcccat | 300 |
| agtaacgcca atagggactt tccattgacg tcaatgggtg gagtatttac ggtaaactgc | 360 |
| ccacttggca gtacatcaag tgtatcatat gccaagtccg cccctattg acgtcaatga | 420 |
| cggtaaatgg cccgcctggc attatgccca gtacatgacc ttacgggact ttcctacttg | 480 |
| gcagtacatc tacgtattag tcatcgctat taccatggtg atgcggtttt ggcagtacac | 540 |
| caatgggcgt ggatagcggt ttgactcacg gggatttcca agtctccacc ccattgacgt | 600 |
| caatgggagt ttgttttggc accaaaatca acgggacttt ccaaaatgtc gtaataaccc | 660 |
| cgccccgttg acgcaaatgg gcggtaggcg tgtacggtgg gaggtctata taagcagagc | 720 |
| tcgtttagtg aaccgtcaga tcactagaag ctttattgcg gtagtttatc acagttaaat | 780 |
| tgctaacgca gtcagtgctt ctgacacaac ggtctcgaac ttaagctgca gaagttggtc | 840 |
| gtgaggcact gggcaggtaa gtatcaaggt tacaagacag gtttaaggag accaatagaa | 900 |
| actgggcttg tcgagacaga gaagactctt gcgtttctga taggcaccta ttggtcttac | 960 |
| tgacatccac tttgcctttc tctccacagg tgtccactcc cagttcaatt acagctctta | 1020 |
| aggctagagt acttaatacg actcactata ggctagcctc gatacaccag acaagtgagt | 1080 |
| atgatgaatc agctgcttat tgccatttta ttagctagtg cttgcttagt atattgcacc | 1140 |
| caatatgtaa ctgttttcta tggcgtaccc acgtggaaaa atgcaaccat tccctctttt | 1200 |
| tgtgcaacca gaaatagggga tacttgggga accatacagt gcttgcctga caatgatgat | 1260 |
| tatcaggaaa taactttgaa tgtaacagag cttttgatg catggaataa tacagtaaca | 1320 |
| gaacaagcaa tgaaagatgt ctggcatcta ttcgagacat caataaaacc atgtgtcaaa | 1380 |
| ctaacaccttt tatgtgtagc aatgaaatgc agcagcacag agagcagcat agggaacaac | 1440 |
| acaacctcaa agagcacaag cacaaccaca accacaccca cagaccagga gcaagagata | 1500 |

```
agtgaggata ctccatgcgc acgcgcagac aactgctcag gattgggaga ggaagaaacg    1560
atcaattgcc agttcaatat gacaggatta gaaagagata agaaaaaaca gtataatgaa    1620
acatggtact caaaagatgt ggtttgtgag acaaataata gcacaaatca gacccagtgt    1680
tacatgaacc attgcaacac atcagtcatc acagaatcat gtgacaagca ctattgggat    1740
gctataaggt ttagatactg tgcaccaccg ggttatgccc tattaagatg taatgatacc    1800
aattattcag gctttgcacc caactgttct aaagtagtag cttctacatg caccaggatg    1860
atggaaacgc aaacttccac atggtttggc tttaatggca ctagagcaga aatagaaca    1920 tatatctatt ggcatggcag agataataga actatcatca gcttaaacaa atattataat    1980
ctcagtttgc attgtaagag gccagggaat aagatagtga acaaataat gcttatgtca     2040 ggacatgtgt ttcactccca ctaccagccg atcaataaaa gacccagaca agcatggtgc    2100
tggttcaaag gcaaatggaa agacgccatg caggaggtga aggaaaccct tgcaaaacat    2160
cccaggtata gaggaaccaa tgacacaagg aatattagct ttgcagcgcc aggaaaaggc    2220
tcagacccag aagtagcata catgtggact aactgcagag gagagtttct ctactgcaac    2280
atgacttggt tcctcaattg gatagagaat aagacacacc gcaattatgc accgtgccat    2340
ataaagcaaa taattaacac atggcataag gtagggagaa atgtatattt gcctcccagg    2400
gaaggggagc tgtcctgcaa ctcaacagta accagcataa ttgctaacat tgactggcaa    2460
aacaataatc agacaaacat tacctttagt gcagaggtgg cagaactata cagattggag    2520
ttgggagatt ataaattggt agaaataaca ccaattggct tcgcacctac aaaagaaaaa    2580
agatactcct ctgctcacgg gagacataca agaggtgtgt tcgtgctagg gttcttgggt    2640
tttctcgcaa cagcaggttc tgcaatgggc gcggcgtccc tgaccgtgtc ggctcagtcc    2700
cggactttac tggccgggat agtgcagcaa cagcaacagc tgttggacgt ggtcaagaga    2760
caacaagaac tgttgcgact gaccgtctgg ggaacgaaaa acctccaggc aagagtcact    2820
gctatagaga agtacctaca ggaccaggcg cggctaaatt catggggatg tgcgtttaga    2880
caagtctgcc acactactgt accatggggtt aatgattcct tagcacctga ctgggacaat    2940
atgacgtggc aggaatggga aaaacaagtc cgctacctgg aggcaaatat cagtaaaagt    3000
ttagaacagg cacaaattca gcaagagaaa aatatgtatg aactacaaaa attaaatagc    3060
tgggatattt ttggcaattg gtttgactta acctcctggg tcaagtatat tcaatatgga    3120
gtgcttataa tagtagcagt aatagcttta agaatagtga tatgtgtagt acaaatgtta    3180
agtaggctta gaaagggcta taggcctgtt ttctcttccc ccccggttat atccaacaga    3240
tccatatcca caaggaccgg ggacagccag ccaacgaaga aacagaagaa gacggtggaa    3300
gcaacggtgg agacagatac tggccctggc cgatagcata tatacatttc ctgatccgcc    3360
agctgattcg cctcttgacc agactataca gcatctgcag ggacttacta tccaggagct    3420
tcctgaccct ccaactcatc taccagaatc tcagagactg gctgagactt agaacagcct    3480
tcttgcaata tgggtgcgag tggatccaag aagcattcca ggccgccgcg agggctacaa    3540
gagagactct tgcgggcgcg tgcagggggct tgtggagggt attggaacga atcgggaggg    3600
gaatactcgc ggttccaaga aggatcagac agggagcaga aatcgcctcc tgtgagggac    3660
ggcagtatag ccagggagac tttatgaata ctccatgggg cggccgcttc gagcagacat    3720
gataagatac attgatgagt ttggacaaac cacaactaga atgcagtgaa aaaaatgctt    3780
tatttgtgaa atttgtgatg ctattgcttt atttgtaacc attataagct gcaataaaca    3840
agttaacaac aacaattgca ttcattttat gtttcaggtt cagggggaga tgtgggaggt    3900
```

```
tttttaaagc aagtaaaacc tctacaaatg tggtaaaatc gataaggatc cgggctggcg    3960
taatagcgaa gaggcccgca ccgatcgccc ttcccaacag ttgcgcagcc tgaatggcga    4020
atggacgcgc cctgtagcgg cgcattaagc gcggcgggtg tggtggttac gcgcagcgtg    4080
accgctacac ttgccagcgc cctagcgccc gctcctttcg ctttcttccc ttcctttctc    4140
gccacgttcg ccggctttcc ccgtcaagct ctaaatcggg gctcccttt agggttccga     4200 ttt                                                                  4203

<210> SEQ ID NO 24
<211> LENGTH: 530
<212> TYPE: DNA
<213> ORGANISM: Human immunodeficiency virus type 2

<400> SEQUENCE: 24
ccaattggct tcgcacctac aaaagaaaaa agatactcct ctgctcacgg gagacataca     60
agaggtgtgt tcgtgctagg gttcttgggt tttctcgcaa cagcaggttc tgcaatgggc    120
gcggcgtccc tgaccgtgtc ggctcagtcc cggactttac tggccgggat agtgcagcaa    180
cagcaacagc tgttggacgt ggtcaagaga caacaagaac tgttgcgact gaccgtctgg    240
ggaacgaaaa acctccaggc aagagtcact gctatagaga gtacctaca ggaccaggcg     300 cggctaaatt catggggatg tgcgtttaga caagtctgcc acactactgt accatgggtt    360
aatgattcct tagcacctga ctgggacaat atgacgtggc aggaatggga aaaacaagtc    420
cgctacctgg aggcaaatat cagtaaaagt ttagaacagg cacaaattca gcaagagaaa    480
aatatgtatg aactacaaaa attaaatagc tgggatattt ttggcaattg                530

<210> SEQ ID NO 25
<211> LENGTH: 761
<212> TYPE: DNA
<213> ORGANISM: Artificial Sequence
<220> FEATURE:
<223> OTHER INFORMATION: Description of Artificial Sequence: mutant
                        green fluorescent protein

<400> SEQUENCE: 25
ggatccaccg gtcgccacca tggtgagcaa gggcgaggag ctgttcaccg gggtggtgcc     60
catcctggtc gagctggacg gcgacgtaaa cggccacaag ttcagcgtgt ccggcgaggg    120
cgagggcgat gccacctacg gcaagctgac cctgaagttc atctgcacca ccggcaagct    180
gcccgtgccc tggcccaccc tcgtgaccac cctgacctac ggcgtgcagt gcttcagccg    240
ctaccccgac cacatgaagc agcacgactt cttcaagtcc gccatgcccg aaggctacgt    300
ccaggagcgc accatcttct tcaaggacga cggcaactac aagacccgcg ccgaggtgaa    360
gttcgagggc gacaccctgg tgaaccgcat cgagctgaag ggcatcgact tcaaggagga    420
cggcaacatc ctggggcaca gctggagta caactacaac agccacaacg tctatatcat    480
ggccgacaag cagaagaacg gcatcaaggt gaacttcaag atccgccaca acatcgagga    540
cggcagcgtg cagctcgccg accactacca gcagaacacc cccatcggcg acggccccgt    600
gctgctgccc gacaaccact acctgagcac ccagtccgcc ctgagcaaag accccaacga    660
gaagcgcgat cacatggtcc tgctggagtt cgtgaccgcc gccgggatca ctctcggcat    720
ggacgagctg tacaagtaaa gcggccgcga ctctagatca t                        761
```

<210> SEQ ID NO 26
<211> LENGTH: 792
<212> TYPE: DNA
<213> ORGANISM: Human immunodeficiency virus type 2

<400> SEQUENCE: 26

```
ttaacctgca actctacagt gaccagcata attgctaaca ttgacggagg agagaaccag      60
acaaatatta cctttagtgc agaggtggca gaactatacc gattagaatt ggggattat     120
aaattgatag aagtaacacc aattggcttt gcacctacac cagtaaaaag atactcctct    180
gctccagtga ggaataaaag aggtgtattc gtgctagggt tcttaggttt tctcacgaca    240
gcaggagctg caatgggcgc ggcgtccttg acgctgtcgg ctcagtctcg gactttattg    300
gccgggatag tgcagcaaca gcaacagctg ttggacgtgg tcaagagaca caagaaatg    360
ttgcgactga ccgtctgggg aacaaaaaat ctccaggcaa gagtcactgc tatcgagaaa    420
tacttaaagg accaggcgca actaaattca tggggatgtg cgtctagaca agtctgccac    480
actactgtac catgggtaaa tgacaccta acgcctgatt ggaacaacat gacatggcag    540
gaatgggagc aacgaatccg caacctagag gcaaatatca gtgaaagttt agaacaggca    600
caaatccagc aagaaaagaa catgtatgaa ctacaaaaat taaatagctg ggatgttttt    660
ggcaactggt ttgatttaac ctcctggatc aaatatattc agtatggagt ttatatagta    720
gtaggaataa tagttttaag aatagtaata tatgtagtac aaatgttaag tagacttaga    780
aagggctata gg                                                          792
```

<210> SEQ ID NO 27
<211> LENGTH: 2801
<212> TYPE: DNA
<213> ORGANISM: Mus musculus

<400> SEQUENCE: 27

```
ctgaaccaaa ggatttctat ggccatgaag ctttgagca gagatacgcg gctggtctgt      60
gagcttgcgc tttgtcccct ggctttagtt ttctggagca ttcttggggt cagagcattg    120
gacaatggct ggcgcggac tcctactatg gctggctgc attgggaacg tttcatgtgc     180
aaccttgact gccaagaaga gcctgatgcc tgcataagtg agcaactgtt catgcagatg    240
gcagagctca tggtctctga tggctggcgg atgcaggtt atgactatct ctgcatagat    300
gactgttgga tggctcccga gagggattca aagggcaggc ttcaggcaga tccccaacgc    360
tttcctagtg ggatcaaaca cctcgcaaat tacgtccaca gcaaaggatt gaagctaggg    420
atttatgcag atgttggaa taaaacctgt gcaggttttcc ccgggagttt tggatcctat    480
gacattgatg cgcagacatt tgctgactgg gcgtagatc tgctaaaatt tgatggttgt    540
cactgtgaca gtgtagtatc cttggagaat ggttataagt acatggcctt ggccttgaac    600
aggacaggcc gaagcattgt atactcctgt gagtggccac tttatttgag acccttttcat   660
aagcccaatt atacagatat ccaatattac tgcaatcatt ggagaaattt tgatgatgtt    720
tatgattcct gggaaagcat aaagaatatc ttgtcttgga cagtggttta ccagaaggag    780
attgttgaag tcgctggacc aggcagctgg aatgacccag acatgttagt gatcggcaac    840
tttggcctca gttgggacca gcaggtgaca cagatggccc tctgggctat catggccgct    900
cccctactca tgtccaacga tctgcgacaa atcagctctc aagccaaagc tctgcttcag    960
aataaggatg taattgccat caaccaagac cccttgggca gcagggcta ctgttcaga    1020
aaggaaaacc acattgaggt ttgggaacgg ccactctcca acctagcctg gctgtggct    1080
```

-continued

| | | | | |
|---|---|---|---|---|
| gtgagaaacc | tgcaggagat | tggtggacct | tgtccttata | ccatccagat ttcttccctg | 1140 |
| ggtagaggac | tagcctgcaa | tcctggctgc | atcattactc | agcttctccc cgagaaagta | 1200 |
| cacctaggct | tctatgaatg | gactttgacc | ttaaaaactc | gagtaaaccc ctcaggcact | 1260 |
| gttttgtttc | ggttagaaag | ataaactact | atataggcag | agttctatgt cccgttttac | 1320 |
| taccaaacca | aactatttcc | tgcccctccc | tctaaaaata | aagtatccca aaggcattgc | 1380 |
| ccttaaaagc | tgcttttcaa | cataggcttt | tgaaattaag | tgggtactcc tgtgcaatat | 1440 |
| tccgaggtgg | actgggagga | gggtaaaagt | gtggaatgta | ttgaaaacag atttcaaaaa | 1500 |
| aaaagtctct | acttcgggtt | ttcttataac | ttgtaaccgg | taggctgtag cagatgcttc | 1560 |
| cgtacactgg | ttgattttaa | ccttcacaac | cctgaagcag | ctgtttatcc actataatct | 1620 |
| ttacagccaa | gtcaaaagca | acaaaaaacc | ctttagatgt | atgtggttca agagttttgc | 1680 |
| ctgtatgtat | gaggtccaca | tacataccgg | gtgcccagga | agccagaaga acaagtgctt | 1740 |
| ttttttcccc | aagacagggt | ttctccatat | agccctggct | gtcctggaac tcactctgta | 1800 |
| gaccaggatg | gccttgaatt | tagaaatccg | cctgcctcag | cctccaaagt gctgggatta | 1860 |
| aaggcctgcg | ccaccaccgc | ccagccttt | ttgttgtttt | gacaagtgcc cttaatcact | 1920 |
| gagccagcaa | gctctagcac | ccagaaccag | gatttaaagc | taaaccagcc agacacaaat | 1980 |
| aactatatgg | aggcactgct | tagtctagtg | caaaggaaaa | aatgaaaatc tgcttcctcc | 2040 |
| aggtgacaga | ctggatgtgg | tagcatgtcc | ttaatcccag | tactagggag gcaatggcaa | 2100 |
| tgcaagtat | aattcaaggc | cagcctggac | tacaaagtgc | aagcctggct ggaaacaaac | 2160 |
| tcatatgccc | aggttatccc | ctagagctaa | gaaatgcaga | taggattacc tgtatttacc | 2220 |
| aatggtgatt | ggctacatga | tgtcctaaga | gcaattgatg | aactgtcctg gtgacaaact | 2280 |
| gggggattcg | ggaggaaaaa | ggtttggaag | gatgctcagg | tgttattta cacaaagcca | 2340 |
| gtatgatggt | gttccatgcc | tccaaccagc | acttggtgag | gataaggcca gagaaaccca | 2400 |
| ggggaggaac | tagggacact | tcaattcaat | ctaaaacaag | ggatgtatat tgaagcatgc | 2460 |
| tccccagact | cccttaatgc | ctgaagtgcc | cagcagtggt | agcacacgcc tttaaccccta | 2520 |
| gcacttagga | ggcagaggca | gccggatgag | ttctgaattc | gaggccagcc tggtctacag | 2580 |
| agttccagga | cagccagggc | tatacagaga | aaccctgtct | cagggaaaaa aaatgagggc | 2640 |
| ctggagaaat | gattcagcgg | ttaagaggat | tgactgctct | tccaaaggtc atgagttcaa | 2700 |
| atcccagcaa | ccacatggtg | gctcacaata | atctgcaatg | agatctgatg ccctcttctg | 2760 |
| gttctctaga | cagcaacatt | atacttgcat | aataatcttt | t | 2801 |

<210> SEQ ID NO 28
<211> LENGTH: 1610
<212> TYPE: DNA
<213> ORGANISM: Bos taurus

<400> SEQUENCE: 28

| | | | | |
|---|---|---|---|---|
| cgaggaaggc | cagttaccat | gaatgcaagc | gagttccgca | ggcgggggaa ggagatggtg | 60 |
| gattacgtgg | ctgactactt | ggagggcatt | gaagggcgcc | agtgttccc tgacgtggat | 120 |
| ccaggctacc | tgcgcccct | gatccccacc | accgccccgc | aggagccaga gacatttgag | 180 |
| gccatcatcg | aggacatcga | gaagatcatc | atgccggggg | tgacccactg gcacagtccc | 240 |
| tacttcttcg | cctacttccc | cacggccagt | tcgtacccgg | ccatgctcgc ggacatgctg | 300 |
| tgtgggccca | tcggctgcat | cggcttctcc | tgggctgcca | gccggcgtg cacagagctc | 360 |
| gagacggtga | tgatggactg | gctggggaag | atgctgcagc | tgccagaggc gtttctggct | 420 |

```
ggagaagctg gagaaggcgg cggggtgatc cagggaactg ccagtgaagc tacccttgtg      480
gccctgctgg ccgctcggac caaagtgacc cgacacctgc aggctcgtgc cccagagctg      540
acgcaggctg ccatcatgga gaagttggtg gcctacgcat ctgaccaggc acactcctcc      600
gtggaaaaag ccggcttaat tggcggagtg agattaaaag ccatcccttc cgatggcaag      660
tttgccatgc gagcttcgcg ctgcaggagg ctggagagag acaaggcagc cggcctgatt      720
ccttcttgct tcgtggtggc tacactgggg accacgtcct gctgctcctt tgacaacctc      780
ttagaagtgg ggcccatttg tcacaaggag gcttgtggc tgcacgtgga cgccgcctac       840
gcaggcagtg ccttcatctg ccctgagttc ggcatcttc tgaatggcgt ggagtttgca       900
gattcattta actttaatcc ccacaaatgg ctcttggtga attttgactg ctctgccatg      960
tgggtgaaaa agaggacaga cctgaccgga gccttcaggc tggacccagt ctatctgagg     1020
cacagccacc aggactcagg gcttatcact gactacaggc actggcagct gccactgggc     1080
cggaggttcc gctcttttgaa gatgtggttt gttttttagga tgtacggagt caagggactg     1140
caggcctata tccgcaagca tgtccagctg tcccatgcat tcgaggcatt ggtgcgccag     1200
gacacccgct ttgaaatctg tgcagaagtc attctgggac tggtctgttt ccggctaaag     1260
ggttccaaca aactgaacga agctcttctg gaaagcataa acagtgccaa aaaaatccac     1320
ttggtccctt gttccctgag agaccggttc gtgctgcgct tcgccatctg ctcacgcaca     1380
gtggagctgg cccacgtaca gctggcctgg gagcacatcc aggagatggc ggccacagtg     1440
ttaagagcac aggggagga aaaggcagag atcaaaaatt gaaattatct gaagactggg      1500
atgagaggaa actgtatcag cccagctcct tggaacccag cctgtatgtg gcacatgctt     1560
ctccagttca gttcagtggc tcagtcgtat ctgactcttt gtgaccccat               1610
```

<210> SEQ ID NO 29
<211> LENGTH: 466
<212> TYPE: DNA
<213> ORGANISM: Homo sapiens

<400> SEQUENCE: 29

```
cctccgacag cctctccaca ggtaccatga aggtctccgc ggcacgcctc gctgtcatcc       60
tcattgctac tgccctctgc gctcctgcat ctgcctcccc atattcctcg gacaccacac      120
cctgctgctt tgcctacatt gcccgcccac tgccccgtgc ccacatcaag gagtatttct      180
acaccagtgg caagtgctcc aacccagcag tcgtctttgt cacccgaaag aaccgccaag      240
tgtgtgccaa cccagagaag aaatgggttc gggagtacat caactctttg gagatgagct      300
aggatggaga gtccttgaac ctgaacttac acaaatttgc ctgtttctgc ttgctcttgt      360
cctagcttgg gaggcttccc ctcactatcc taccccaccc gctccttgaa gggcccagat      420
tctgaccacg acgagcagca gttacaaaaa ccttccccag gctgga                    466
```

<210> SEQ ID NO 30
<211> LENGTH: 657
<212> TYPE: DNA
<213> ORGANISM: Homo sapiens

<400> SEQUENCE: 30

```
atggacgggt ccggggagca gcccagaggc gggggcccca ccagctctga gcagatcatg       60
aagacagggg ccctttttgct tcagggtttc atccaggatc gagcagggcg aatggggggg      120
gaggcacccg agctggccct ggacccggtg cctcaggatg cgtccaccaa gaagctgagc      180
```

-continued

```
gagtgtctca agcgcatcgg ggacgaactg gacagtaaca tggagctgca gaggatgatt      240
gccgccgtgg acacagactc ccccgagag gtctttttcc gagtggcagc tgacatgttt      300
tctgacggca acttcaactg gggccgggtt gtcgcccttt tctactttgc cagcaaactg      360
gtgctcaagg ccctgtgcac caaggtgccg gaactgatca gaaccatcat gggctggaca      420
ttggacttcc tccgggagcg gctgttgggc tggatccaag accagggtgg ttgggtgaga      480
ctcctcaagc ctcctcaccc ccaccaccgc gccctcacca ccgcccctgc cccaccgtcc      540
ctgccccccg ccactcctct gggaccctgg gccttctgga gcaggtcaca gtggtgccct      600
ctccccatct tcagatcatc agatgtggtc tataatgcgt tttccttacg tgtctga        657
```

<210> SEQ ID NO 31
<211> LENGTH: 3873
<212> TYPE: DNA
<213> ORGANISM: Artificial Sequence
<220> FEATURE:
<223> OTHER INFORMATION: Description of Artificial Sequence:
      pSGT-5(SDM/RRE1/CM)

<400> SEQUENCE: 31

```
ggaagggctg tattacagtg ataggagacg tagagtccta gacatatact tagaaaagga       60
agagggaata attggagact ggcagaacta tactcatgga ccaggagtaa ggtatccaaa      120
gttctttggg tggttatgga agctagtacc agtagatgtc ccacaagagg agatgcacag      180
tgagactcac tgcttagtgc atccagcaca aacaagcagg tttgatgacc cgcatggaga      240
aacattagtt tggaggtttg accccacgct agcttttagc tacgaggcct ttattcgata      300
cccagaggag tttgggtaca gtcaggcct gccagaggat gaatggaagg caagactgaa      360
agcaagaggg ataccgttta gctaaaaaca ggaacagcta tacttggtca gggcaggaag      420
taactaacag aaaacagctg agactgcagg gactttccag aaggggctgt taccagggga      480
gggacatggg aggagccggt ggggaacgcc ctcatacttt ctgtataaat gtacccgcta      540
ctcgcattgt attcagtcgc tctgcggaga ggctggcaga ttgagccctg ggaggttctc      600
tccagcacta gcaggtagag cctgggtgtt ccctgctaga ctctcaccag tgcttggccg      660
gcactgggca gacggctcca cgcttgcttg cttaaaagac ctcttaataa agctgccagt      720
tagaagcaag ttagtgtgt gctcccatct tcctagtcg ccgcctggtc attcggtgtt      780
catctaaagt aacaagaccc tggtctgtta ggacccttc tgctttggga aaccaaggca      840
ggaaaatccc tagcaggttg gcgcccgaac agggacttga agaagactga gaagccttgg      900
aacacggctg agtgaaggca gtaagggcgg caggaacaaa ccacgacgga gtgctcctag      960
aaaagcgcag gccgaggtac caagggcggc gtgtggagcg ggagtgaaag aggcctccgg     1020
gtgatatcag tgcctacacc aaatacagta gccagaaggg cttgttatcc tacctttaga     1080
cgggtagaag attgtgggag atgccatggt agggcgcgag aaactccgtc ttgagaggga     1140 aaaagcaga cgaattagaa aagattaggt tacggcccgg cggaaagaaa aaatataggc      1200
taaaacatat tgtgtgggca gcgaatgaat tggacagatt cggattggca gagagcctgt     1260
tggagtcaaa agagggttgc caaaaaattc ttacagtttt agatccatta gtaccgacag     1320
ggtcagaaaa tttaaaaagc ctttttaata ctgtctgcgt catttggtgt atacacgcag     1380
aagagaaagc gaaagatact gaagaagcaa aacaaaaggt acagagacat ctagtggcag     1440
aaacaaaaac tacagaaaaa atgccaagta caagtagacc aacagcacca cctagcggga     1500
acggaggact cgaatgcatg gtgaccgcgg ccgcaagagg tgtattcgtg ctagggttct     1560
```

-continued

```
taggttttct cacgacagca ggagctgcaa tgggcgcggc gtccttgacg ctgtcggctc    1620
agtctcggac tttattggcc gggatagtgc agcaacagca acagctgttg gacgtggtca    1680
agagacaaca agaaatgttg cgactgaccg tctggggaac aaaaaatctc caggcaagag    1740
tcactgctat cgagaaatac ttaaaggacc aggcgcaact aaattcatgg ggatgtgcgt    1800
ctagacaagt ctgccacact actgtaccat gggtagcggc cgctcgcgag tcaatattgg    1860
ccattagcca tattattcat tggttatata gcataaatca atattggcta ttggccattg    1920
catacgttgt atctatatca taatatgtac atttatattg gctcatgtcc aatatgaccg    1980
ccatgttggc attgattatt gactagttat taatagtaat caattacggg gtcattagtt    2040
catagcccat atatggagtt ccgcgttaca taacttacgg taaatggccc gcctggctga    2100
ccgcccaacg accccgccca ttgacgtcaa taatgacgat atgttcccat agtaacgcca    2160
atagggactt tccattgacg tcaatgggtg gagtatttac ggtaaactgc ccacttggca    2220
gtacatcaag tgtatcatat gccaagtccg cccctattg acgtcaatga cggtaaatgg    2280
cccgcctggc attatgccca gtacatgacc ttacgggact ttcctacttg gcagtacatc    2340
tacgtattag tcatcgctat taccatggtg atgcggtttt ggcagtacac caatgggcgt    2400
ggatagcggt ttgactcacg gggatttcca agtctccacc ccattgacgt caatgggagt    2460
ttgttttggc accaaaatca acgggacttt ccaaaatgtc gtaataaccc cgccccgttg    2520
acgcaaatgg gcggtaggcg tgtacggtgg gaggtctata taagcagagc tcgtttagtg    2580
aaccgtcaga tcactagaag ctttattgcg gtagtttatc acagttaaat tgctaacgca    2640
gtcagtgctt ctgacacaac agtctcgaac ttaagctgca gaagttggtc gtgaggcact    2700
gggcaggtaa gtatcaaggt tacaagacag gtttaaggag accaatagaa actgggcttg    2760
tcgagacaga gaagactctt gcgtttctga taggcaccta ttggtcttac tgacatccac    2820
tttgcctttc tctccacagg tgtccactcc cagttcaatt acagctctta aggctagagt    2880
acttaatacg actcactata ggctagcctc gagaattcac gcgtggtacc tctagagtcg    2940
acccgggcgg ccgccgactc gagtatccat ggagagcccc agcagaaggg gagaaaggct    3000
cgtacaagca acaaaatatg gatgatgtag attcagatga tgatgaccta gtaggggtcc    3060
ctgtcacacc aagagtacca ttaagagaaa tgacatatag gttggcaaga gatatgtcac    3120
atttgataaa agaaaggggg ggactggaag ggctgtatta cagtgatagg agacgtagag    3180
tcctagacat atacttagaa aaggaagagg gaataattgg agactggcag aactatactc    3240
atggaccagg agtaaggtat ccaaagttct ttgggtggtt atggaagcta gtaccagtag    3300
atgtcccaca agagggagat gacagtgaga ctcactgctt agtgcatcca gcacaaacaa    3360
gcaggtttga tgacccgcat ggagaaacat tagtttggag gtttgacccc acgctagctt    3420
ttagctacga ggcctttatt cgatacccag aggagtttgg gtacaagtca ggcctgccag    3480
aggatgaatg gaaggcaaga ctgaaagcaa gagggatacc gtttagctaa aaacaggaac    3540
agctatactt ggtcagggca ggaagtaact aacagaaaac agctgagact gcaggacttt    3600
tccagaaggg gctgttacca ggggagggac atggaggag ccgtggggga acgccctcat    3660
actttctgta taaatgtacc cgctactcgc attgtattca gtcgctctgc ggagaggctg    3720
gcagattgag ccctggggagg ttctctccag cactagcagg tagagcctgg gtgttccctg    3780
ctagactctc accagtgctt ggccggcact gggcagacgg ctccacgctt gcttgcttaa    3840
aagacctctt aataaagctg ccagttagaa gca                                  3873
```

-continued

```
<210> SEQ ID NO 32
<211> LENGTH: 1616
<212> TYPE: DNA
<213> ORGANISM: Artificial Sequence
<220> FEATURE:
<223> OTHER INFORMATION: Description of Artificial Sequence: IRES and
      Puromycin sequences

<400> SEQUENCE: 32
gaattcagtg gatccactag taacggccgc cagtgtgctg gaattaattc gctgtctgcg      60
agggccagct gttggggtga gtactccctc tcaaaagcgg gcatgacttc tgcgctaaga    120
ttgtcagttt ccaaaaacga ggaggatttg atattcacct ggcccgcggt gatgcctttg    180
agggtggccg cgtccatctg gtcagaaaag acaatctttt tgttgtcaag cttgaggtgt    240
ggcaggcttg agatctggcc atacacttga gtgacaatga catccacttt gcctttctct    300
ccacaggtgt ccactcccag gtccaactgc aggtcgagca tgcatctagg gcggccaatt    360
ccgcccctct ccctccccccc ccctaacgt tactggccga agccgcttgg aataaggccg    420
gtgtgcgttt gtctatatgt gattttccac catattgccg tcttttggca atgtgagggc    480
ccggaaacct ggccctgtct tcttgacgag cattcctagg ggtctttccc ctctcgccaa    540
aggaatgcaa ggtctgttga atgtcgtgaa ggaagcagtt cctctggaag cttcttgaag    600
acaaacaacg tctgtagcga ccccttttgcag gcagcggaac cccccacctg gcgacaggtg    660
cctctgcggc caaaagccac gtgtataaga tacacctgca aaggcggcac aaccccagtg    720
ccacgttgtg agttggatag ttgtggaaag agtcaaatgg ctctcctcaa gcgtattcaa    780 caagggggctg aaggatgccc agaaggtacc ccattgtatg ggatctgatc tggggcctcg    840
gtgcacatgc tttacatgtg tttagtcgag gttaaaaaaa cgtctaggcc cccgaacca    900 cggggacgtg gttttccttt gaaaaacacg atgataagct tgccacaacc cacaaggaga    960
cgaccttcca tgaccgagta caagcccacg gtgcgcctcg ccaccgcga cgacgtcccc   1020 cgggccgtac gcaccctcgc cgccgcgttc gccgactacc ccgccacgcg ccacaccgtc   1080
gacccggacc gccacatcga gcgggtcacc gagctgcaag aactcttcct cacgcgcgtc   1140
gggctcgaca tcggcaaggt gtgggtcgcg gacgacggcg ccgcggtggc ggtctggacc   1200
acgccggaga gcgtcgaagc gggggcggtg ttcgccgaga tcggcccgcg catgccgag   1260 ttgagcggtt cccggctggc cgcgcagcaa cagatggaag gcctcctggc gccgcaccgg   1320
cccaaggagc ccgcgtggtt cctggccacc gtcggcgtct cgcccgacca ccagggcaag   1380
ggtctgggca gcgccgtcgt gctccccgga gtggaggcgg ccgagcgcgc cggggtgccc   1440
gccttcctgg agacctccgc gccccgcaac ctcccccttct acgagcggct cggcttcacc   1500
gtcaccgccg acgtcgagtg cccgaaggac cgcgcgacct ggtgcatgac ccgcaacccg   1560
gtgcctgacg cccgccccac gacccgcagc gcccgaccga aggagcgca cgaccc       1616
```